United States Patent
Shelton, IV et al.

(10) Patent No.: US 12,357,302 B2
(45) Date of Patent: Jul. 15, 2025

(54) INTEGRAL CARTRIDGE STIFFENING FEATURES TO REDUCE CARTRIDGE DEFLECTION

(71) Applicant: Cilag GmbH International, Zug (CH)

(72) Inventors: Frederick E. Shelton, IV, Hillsboro, OH (US); Seth D. Holdmeyer, Cincinnati, OH (US); Adam D. Hensel, Gahanna, OH (US); Nicholas Fanelli, Morrow, OH (US); Kevin M. Fiebig, Cincinnati, OH (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/379,796

(22) Filed: Oct. 13, 2023

(65) Prior Publication Data
US 2025/0120701 A1    Apr. 17, 2025

(51) Int. Cl.
*A61B 17/072* (2006.01)

(52) U.S. Cl.
CPC .. *A61B 17/072* (2013.01); *A61B 2017/07264* (2013.01); *A61B 2017/07271* (2013.01); *A61B 2017/07278* (2013.01); *A61B 2017/07285* (2013.01)

(58) Field of Classification Search
CPC ................ A61B 17/068; A61B 17/072; A61B 2017/07271
See application file for complete search history.

(56) References Cited

U.S. PATENT DOCUMENTS

| | | | |
|---|---|---|---|
| 5,403,312 | A | 4/1995 | Yates et al. |
| 5,485,947 | A | 1/1996 | Olson et al. |
| 6,978,921 | B2 | 12/2005 | Shelton, IV et al. |
| 7,000,818 | B2 | 2/2006 | Shelton, IV et al. |
| 7,401,721 | B2 | 7/2008 | Holsten et al. |
| 7,407,075 | B2 | 8/2008 | Holsten et al. |

(Continued)

FOREIGN PATENT DOCUMENTS

| | | |
|---|---|---|
| CN | 105919642 A | 9/2016 |
| CN | 105997172 A | 10/2016 |

(Continued)

OTHER PUBLICATIONS

U.S. Appl. No. 12/031,573, filed Feb. 14, 2008.

(Continued)

*Primary Examiner* — Gloria R Weeks

(57) ABSTRACT

A surgical stapling assembly comprising a first jaw, a second jaw, and a staple cartridge assembly positioned in the first jaw is disclosed. The staple cartridge assembly comprises a plurality of staples, a plurality of staple drivers, and a cartridge body. The cartridge body comprises a deck surface configured to support patient tissue, a longitudinal slot defined in the cartridge body, a plurality of staple cavities, and a longitudinal wall extending vertically below the deck surface. The longitudinal wall comprises a first zone comprising a first wall height and a second zone comprising a second wall height. The staple cartridge assembly further comprises a sled movable longitudinally through the cartridge body, wherein the sled is sized and configured resist deflection of the cartridge body during the firing stroke within the second zone.

15 Claims, 21 Drawing Sheets

(56) References Cited

U.S. PATENT DOCUMENTS

| | | | |
|---|---|---|---|
| 7,422,139 B2 | 9/2008 | Shelton, IV et al. | |
| 7,464,849 B2 | 12/2008 | Shelton, IV et al. | |
| 7,669,746 B2 | 3/2010 | Shelton, IV | |
| 7,670,334 B2 | 3/2010 | Hueil et al. | |
| 7,735,703 B2 | 6/2010 | Morgan et al. | |
| 7,753,245 B2 | 7/2010 | Boudreaux et al. | |
| 7,845,537 B2 | 12/2010 | Shelton, IV et al. | |
| 7,980,443 B2 | 7/2011 | Scheib et al. | |
| 8,123,100 B2 | 2/2012 | Holsten et al. | |
| 8,141,762 B2 * | 3/2012 | Bedi | A61B 17/0644 227/176.1 |
| 8,210,411 B2 | 7/2012 | Yates et al. | |
| 8,220,688 B2 | 7/2012 | Laurent et al. | |
| 8,308,040 B2 | 11/2012 | Huang et al. | |
| 8,393,514 B2 | 3/2013 | Shelton, IV et al. | |
| 8,499,992 B2 | 8/2013 | Whitman et al. | |
| 8,540,133 B2 * | 9/2013 | Bedi | A61B 17/07207 227/19 |
| 8,561,870 B2 | 10/2013 | Baxter, III et al. | |
| 8,608,045 B2 | 12/2013 | Smith et al. | |
| 8,733,613 B2 | 5/2014 | Huitema et al. | |
| 8,864,007 B2 | 10/2014 | Widenhouse et al. | |
| 8,876,857 B2 | 11/2014 | Burbank | |
| 9,050,083 B2 | 6/2015 | Yates et al. | |
| 9,072,535 B2 | 7/2015 | Shelton, IV et al. | |
| 9,101,358 B2 | 8/2015 | Kerr et al. | |
| 9,131,940 B2 | 9/2015 | Huitema et al. | |
| 9,345,481 B2 * | 5/2016 | Hall | A61B 17/07207 |
| 9,386,988 B2 | 7/2016 | Baxter, III et al. | |
| 9,629,631 B2 | 4/2017 | Nicholas et al. | |
| 9,770,245 B2 | 9/2017 | Swayze et al. | |
| 9,788,835 B2 | 10/2017 | Morgan et al. | |
| 9,839,420 B2 | 12/2017 | Shelton, IV et al. | |
| 9,844,369 B2 | 12/2017 | Huitema et al. | |
| 9,924,944 B2 | 3/2018 | Shelton, IV et al. | |
| 9,987,008 B2 | 6/2018 | Scirica et al. | |
| 10,080,552 B2 | 9/2018 | Nicholas et al. | |
| 10,085,749 B2 * | 10/2018 | Cappola | A61B 17/07207 |
| 10,105,142 B2 * | 10/2018 | Baxter, III | A61B 17/105 |
| 10,123,798 B2 | 11/2018 | Baxter, III et al. | |
| 10,130,363 B2 | 11/2018 | Huitema et al. | |
| 10,166,023 B2 * | 1/2019 | Vendely | A61B 17/07207 |
| 10,213,203 B2 | 2/2019 | Swayze et al. | |
| 10,299,792 B2 | 5/2019 | Huitema et al. | |
| 10,349,939 B2 * | 7/2019 | Shelton, IV | A61B 17/105 |
| 10,357,252 B2 | 7/2019 | Harris et al. | |
| 10,517,593 B2 | 12/2019 | Gupta et al. | |
| 10,537,324 B2 | 1/2020 | Shelton, IV et al. | |
| 10,542,981 B2 | 1/2020 | Miller et al. | |
| 10,568,624 B2 | 2/2020 | Shelton, IV et al. | |
| 10,588,623 B2 | 3/2020 | Schmid et al. | |
| 10,765,427 B2 | 9/2020 | Shelton, IV et al. | |
| 10,898,183 B2 | 1/2021 | Shelton, IV et al. | |
| 10,898,191 B2 | 1/2021 | Huitema et al. | |
| 10,945,727 B2 | 3/2021 | Shelton, IV et al. | |
| 10,952,724 B2 | 3/2021 | Shelton, IV et al. | |
| 11,000,278 B2 | 5/2021 | Shelton, IV et al. | |
| 11,045,191 B2 | 6/2021 | Shelton, IV et al. | |
| 11,058,426 B2 | 7/2021 | Nalagatla et al. | |
| D933,220 S | 10/2021 | Tate et al. | |
| 11,147,552 B2 | 10/2021 | Burbank et al. | |
| 11,207,065 B2 | 12/2021 | Harris et al. | |
| 11,229,433 B2 | 1/2022 | Schings et al. | |
| 11,234,698 B2 * | 2/2022 | Shelton, IV | A61B 17/07207 |
| 11,234,700 B2 | 2/2022 | Ragosta et al. | |
| 11,291,445 B2 | 4/2022 | Shelton, IV et al. | |
| 11,298,129 B2 | 4/2022 | Bakos et al. | |
| 11,337,693 B2 | 5/2022 | Hess et al. | |
| 11,364,029 B2 | 6/2022 | Burbank et al. | |
| 11,382,627 B2 | 7/2022 | Huitema et al. | |
| D967,421 S | 10/2022 | Shelton, IV et al. | |
| 11,490,890 B2 | 11/2022 | Harris et al. | |
| 11,517,315 B2 | 12/2022 | Huitema et al. | |
| D974,560 S | 1/2023 | Shelton, IV et al. | |
| 11,540,826 B2 | 1/2023 | Nalagatla et al. | |
| 11,571,213 B2 | 2/2023 | Huitema et al. | |
| 11,589,865 B2 | 2/2023 | Shelton, IV et al. | |
| 11,701,114 B2 * | 7/2023 | Shelton, IV | A61B 17/07292 227/176.1 |
| 11,737,752 B2 | 8/2023 | Schings et al. | |
| 11,766,257 B2 | 9/2023 | Shelton, IV et al. | |
| 11,826,047 B2 | 11/2023 | Huang et al. | |
| 11,849,944 B2 * | 12/2023 | Shelton, IV | A61B 17/07207 |
| 11,931,031 B2 | 3/2024 | Shelton, IV et al. | |
| 11,974,741 B2 | 5/2024 | Moubarak et al. | |
| 12,133,647 B2 | 11/2024 | Nalagatla et al. | |
| 2007/0175955 A1 | 8/2007 | Shelton, IV et al. | |
| 2014/0001231 A1 | 1/2014 | Shelton, IV et al. | |
| 2014/0263552 A1 | 9/2014 | Hall et al. | |
| 2015/0134077 A1 | 5/2015 | Shelton, IV et al. | |
| 2017/0319205 A1 | 11/2017 | Beardsley | |
| 2018/0132849 A1 | 5/2018 | Miller et al. | |
| 2018/0168615 A1 | 6/2018 | Shelton, IV et al. | |
| 2019/0105047 A1 | 4/2019 | Nalagatla et al. | |
| 2021/0186498 A1 * | 6/2021 | Boudreaux | A61B 17/07207 |
| 2021/0186500 A1 * | 6/2021 | Shelton, IV | A61B 17/07207 |
| 2022/0031320 A1 | 2/2022 | Hall et al. | |
| 2022/0047265 A1 | 2/2022 | Miller et al. | |
| 2022/0304679 A1 * | 9/2022 | Bakos | B33Y 80/00 |
| 2022/0346858 A1 | 11/2022 | Aronhalt et al. | |
| 2023/0119119 A1 | 4/2023 | Moubarak | |

FOREIGN PATENT DOCUMENTS

| | | | |
|---|---|---|---|
| CN | 105997173 A | 10/2016 | |
| CN | 106036848 A | 10/2016 | |
| CN | 108542454 A | 9/2018 | |
| CN | 111195142 A | 5/2020 | |

OTHER PUBLICATIONS

U.S. Food and Drug Administration 510(k) Premarket Notification, https://www.accessdata.fda.gov/scripts/cdrh/cfdocs/cfpmn/pmn.cfrn?ID=K182476, last update: Jan. 8, 2024, 1 page.

* cited by examiner

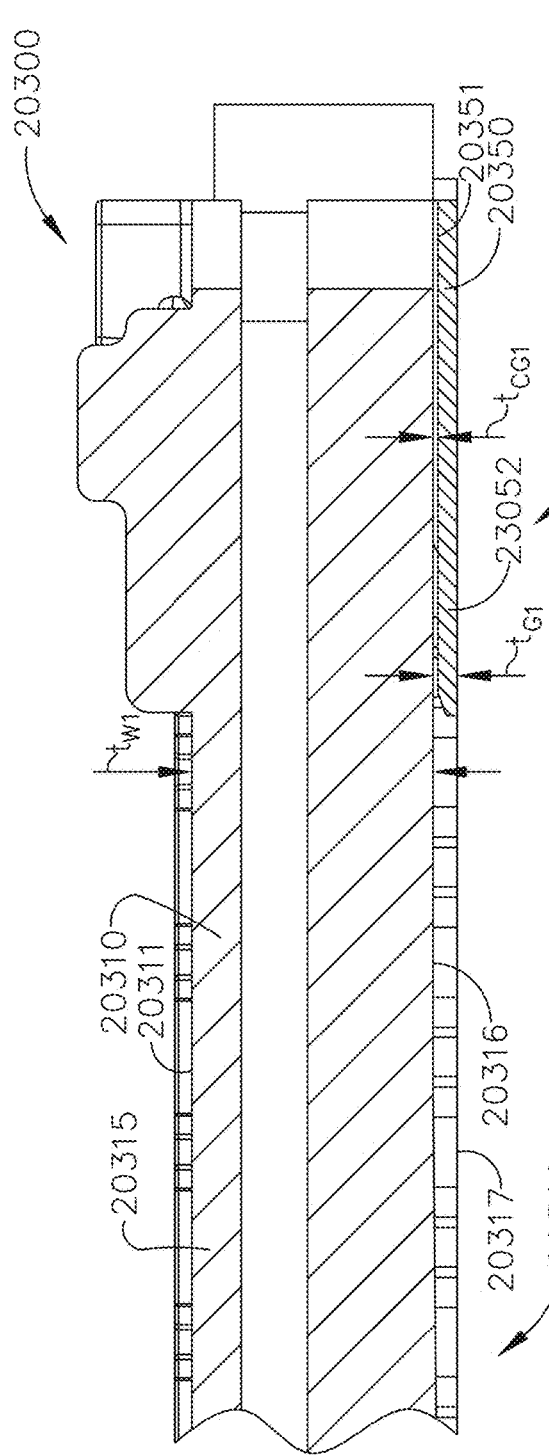
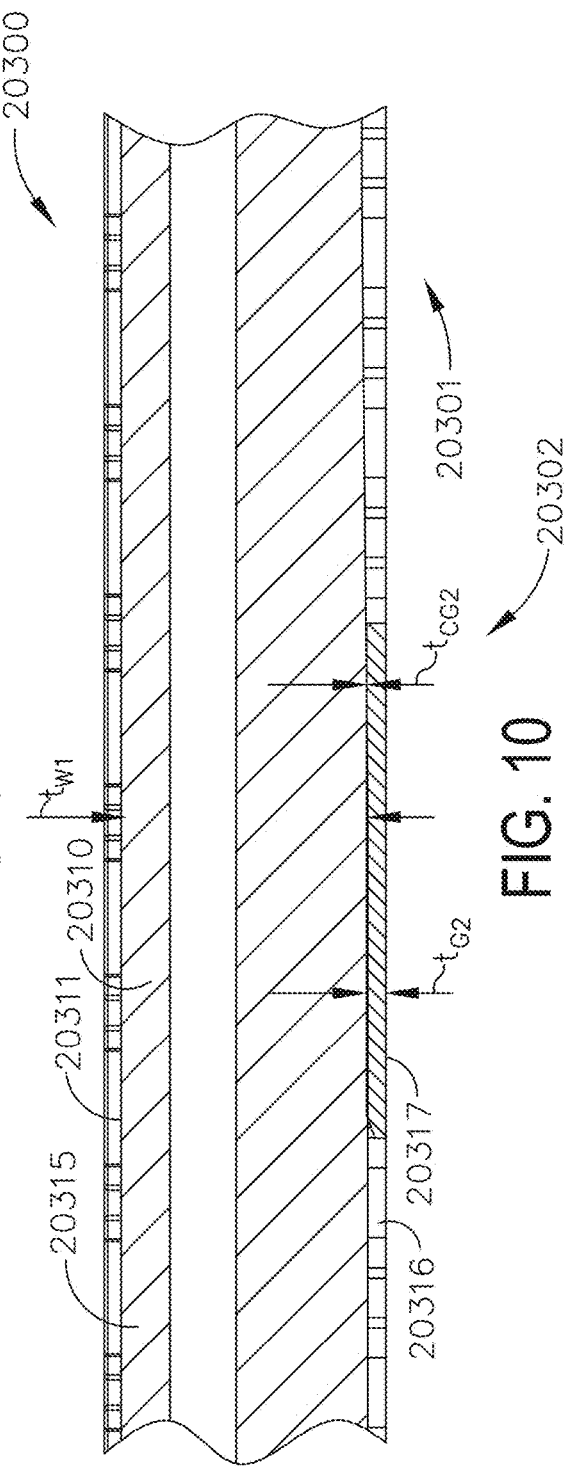

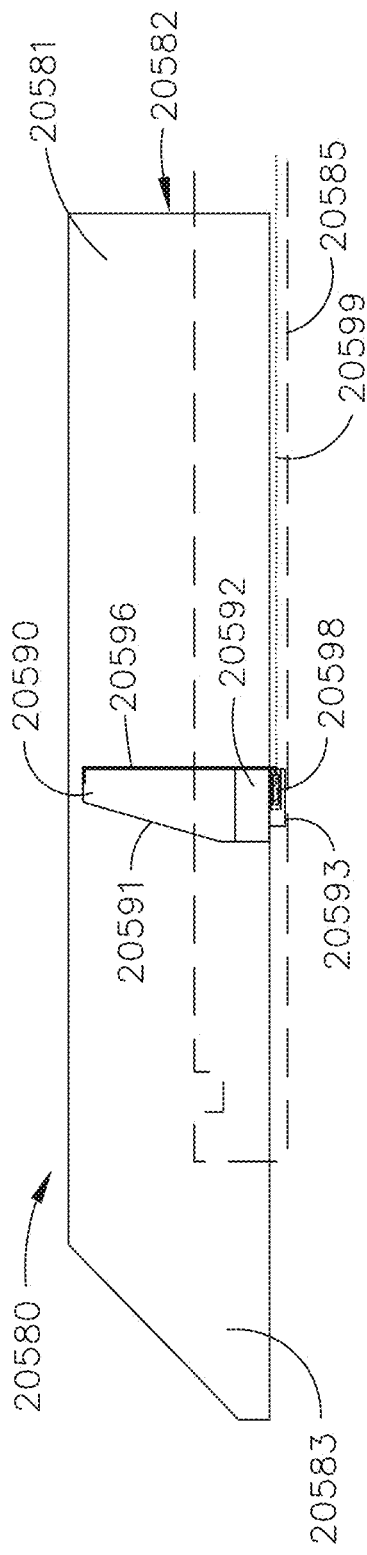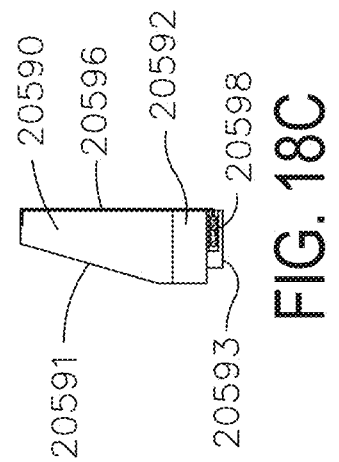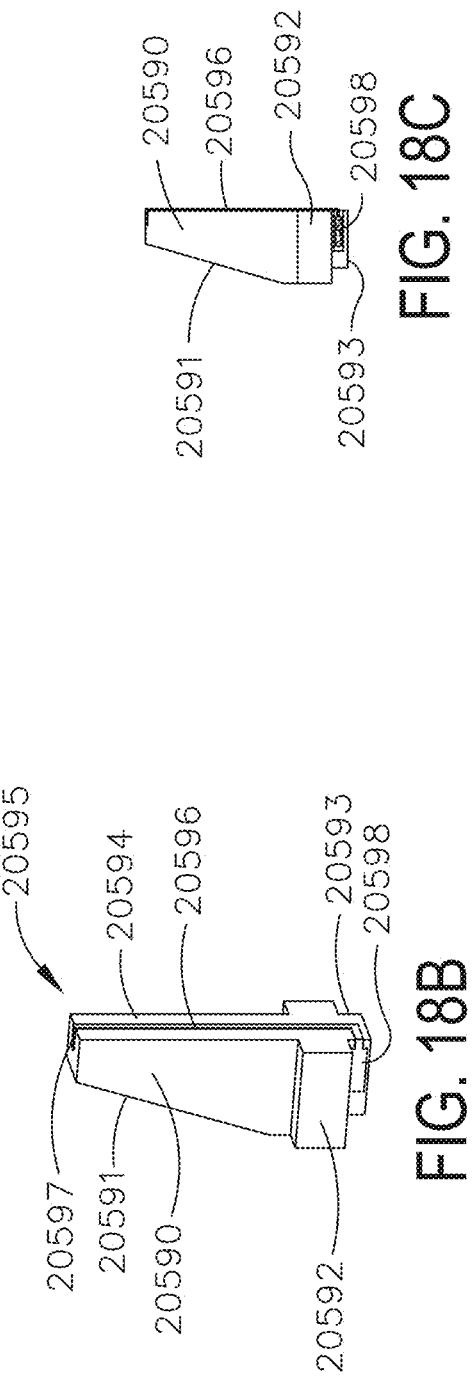

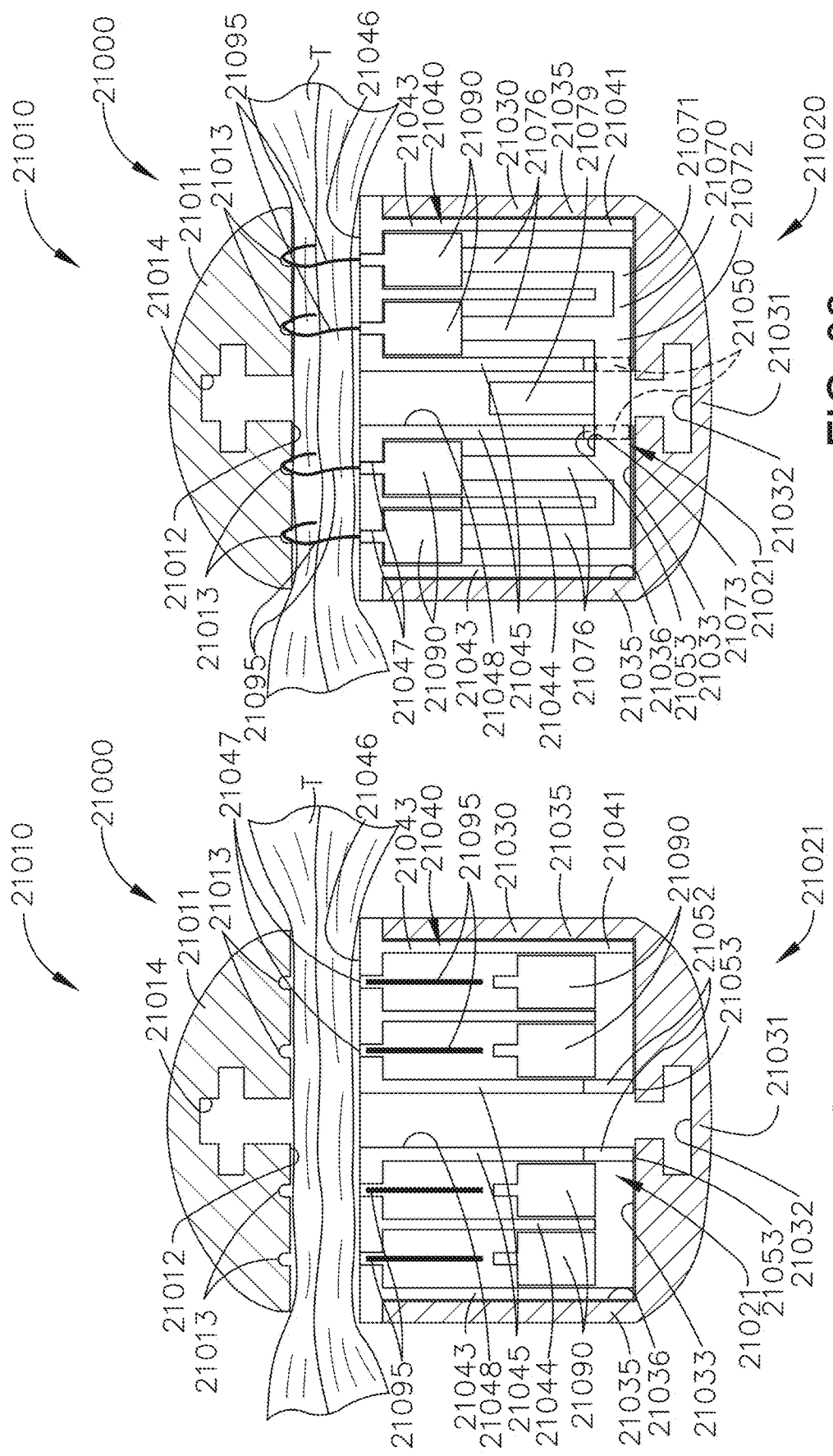

INTEGRAL CARTRIDGE STIFFENING FEATURES TO REDUCE CARTRIDGE DEFLECTION

BACKGROUND

The present invention relates to surgical instruments and, in various arrangements, to surgical stapling and cutting instruments and staple cartridges for use therewith that are designed to staple and cut tissue.

SUMMARY

A surgical stapling assembly comprising a first jaw, a second jaw, and a staple cartridge assembly positioned in the first jaw is disclosed. The staple cartridge assembly comprises a plurality of staples, a plurality of staple drivers, and a cartridge body. The cartridge body comprises a deck surface configured to support patient tissue, a longitudinal slot defined in the cartridge body and configured to receive at least a portion of a knife therethrough during a firing stroke, and a plurality of staple cavities defined in the deck surface, wherein the plurality of staples are removably stored within the plurality of staple cavities. The cartridge body further comprises a longitudinal wall extending vertically below the deck surface and longitudinally adjacent to the longitudinal slot, wherein the longitudinal wall comprises a first zone comprising a first wall height within the firing stroke and a second zone comprising a second wall height within the firing stroke greater than the first wall height. The surgical stapling assembly further comprises a sled movable longitudinally through the cartridge body, wherein the sled comprises a support base and a ramped wedge extending upward from the support base, wherein the ramped wedge is configured to lift the plurality of staple drivers to eject the plurality of staples from the plurality of staple cavities during the firing stroke, and wherein the sled is sized and configured resist deflection of the cartridge body during the firing stroke within the second zone.

A surgical stapling assembly comprising a first jaw, a second jaw, and a staple cartridge assembly positioned in the first jaw is disclosed. The staple cartridge assembly comprises a plurality of staples and a cartridge body. The cartridge body comprises a deck surface configured to support patient tissue, a longitudinal slot defined in the cartridge body and configured to receive at least a portion of a knife therethrough during a firing stroke, and a plurality of staple cavities defined in the deck surface, wherein the plurality of staples are removably stored within the plurality of staple cavities. The staple cartridge assembly further comprises a sled movable longitudinally through the cartridge body to eject the plurality of staples from the plurality of staple cavities during the firing stroke and a longitudinally-translatable support positioned within the longitudinal slot and configured to transfer clamping pressure from the second jaw to the first jaw.

LISTING OF THE FIGURES

Various features of the embodiments described herein, together with advantages thereof, may be understood in accordance with the following description taken in conjunction with the accompanying drawings as follows.

Figure 4:
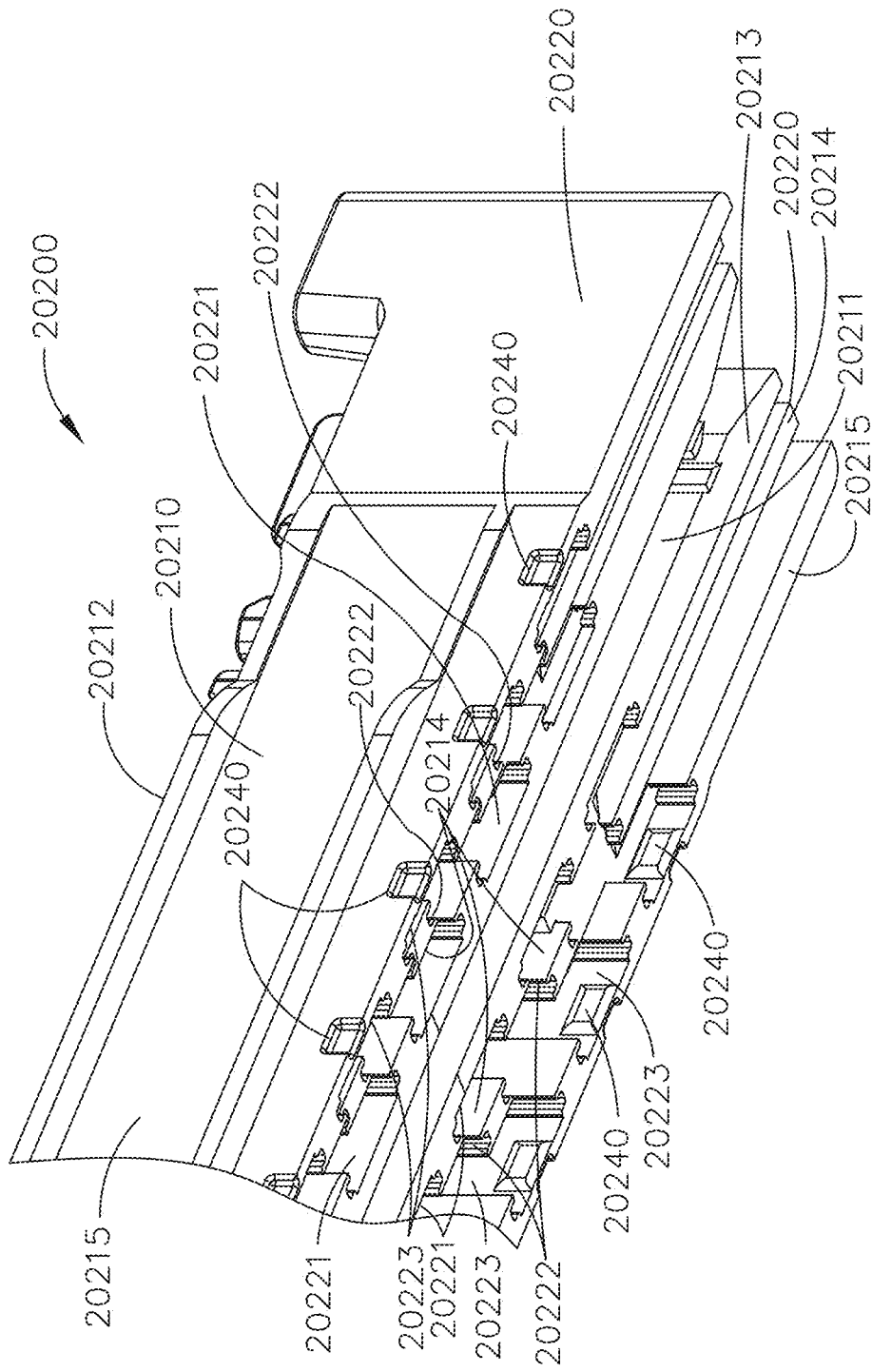
Figure 5:
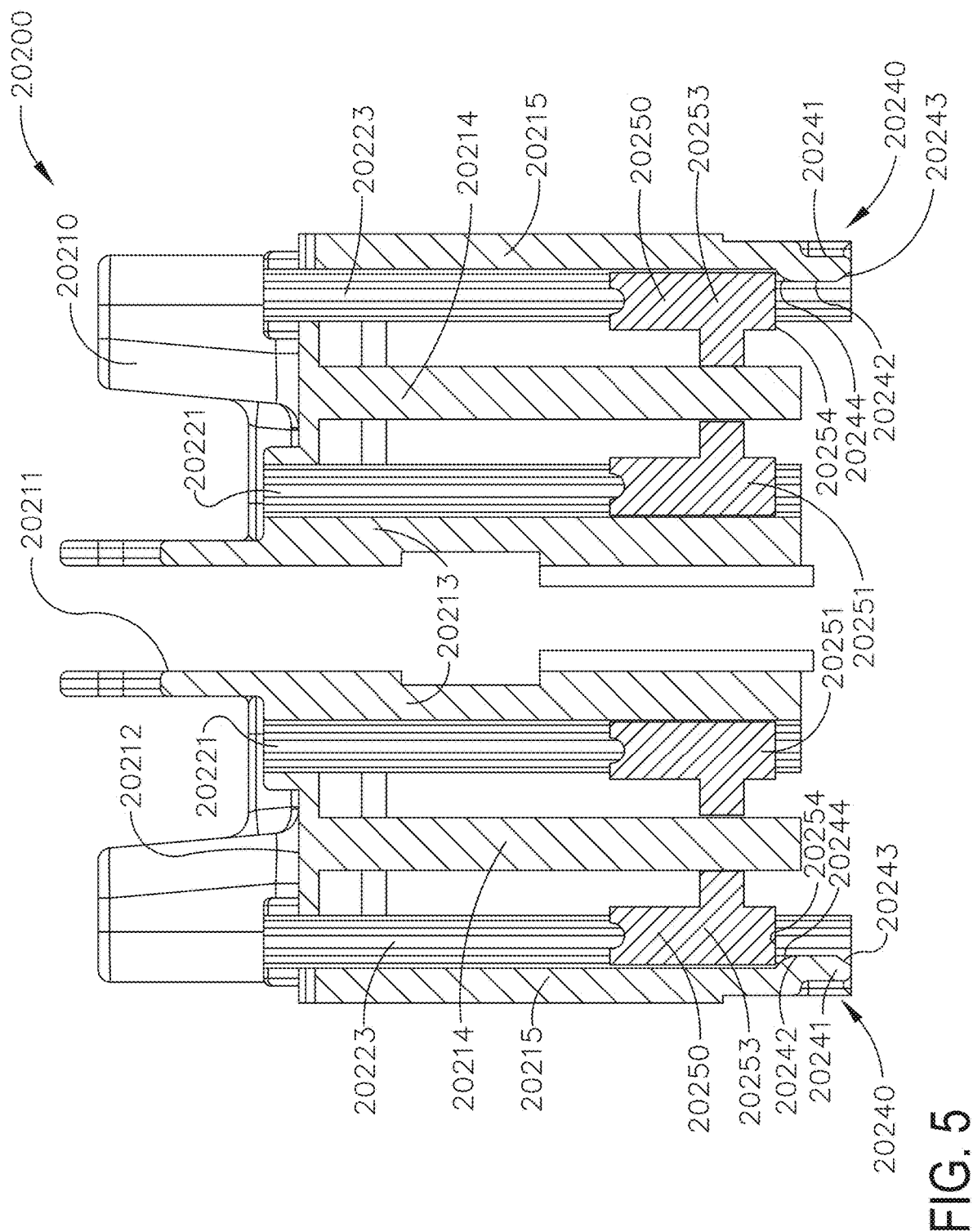
Figure 6:
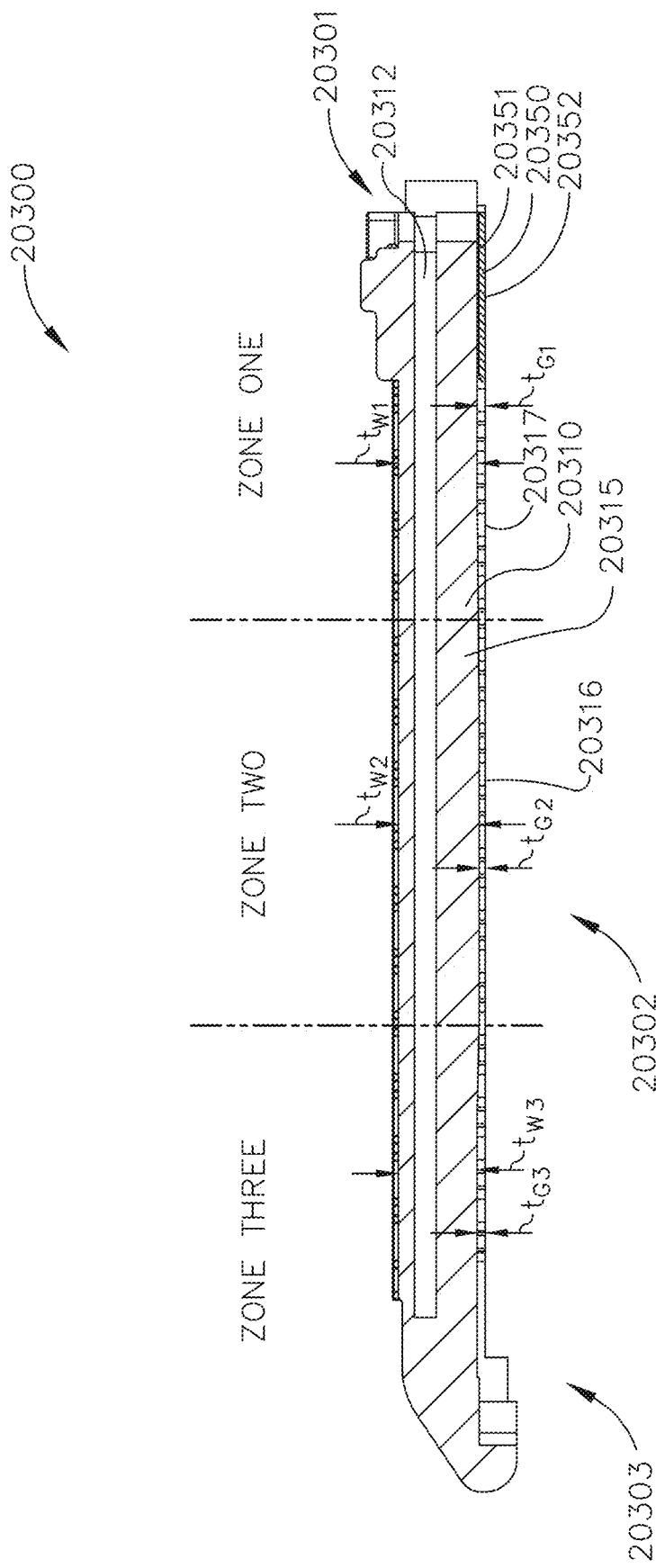
Figure 7:
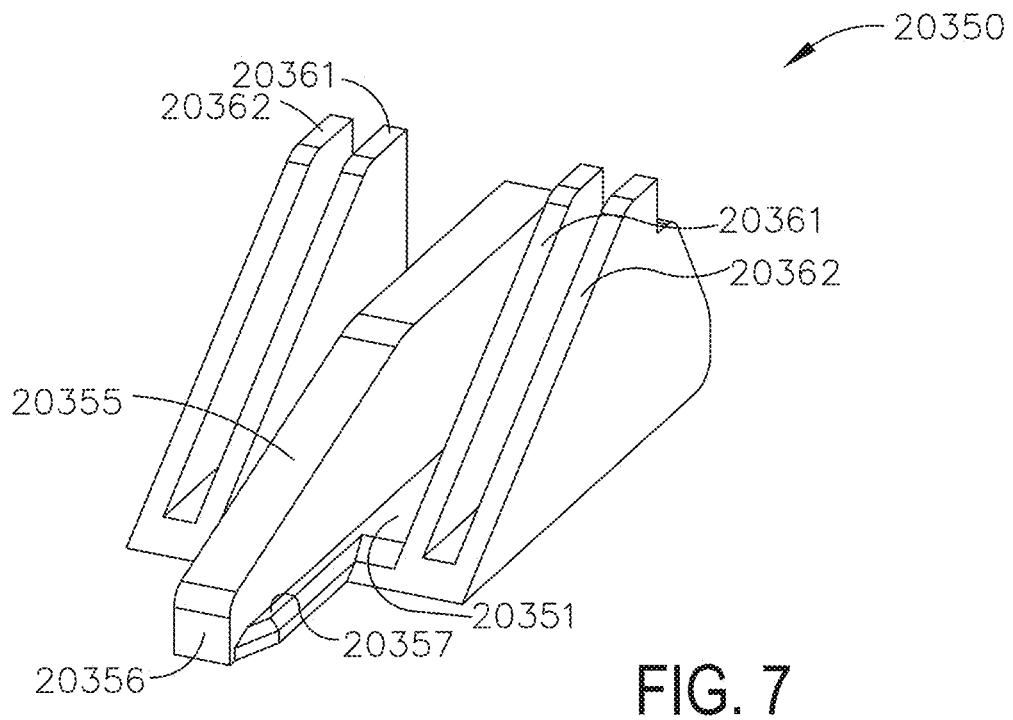
Figure 8:
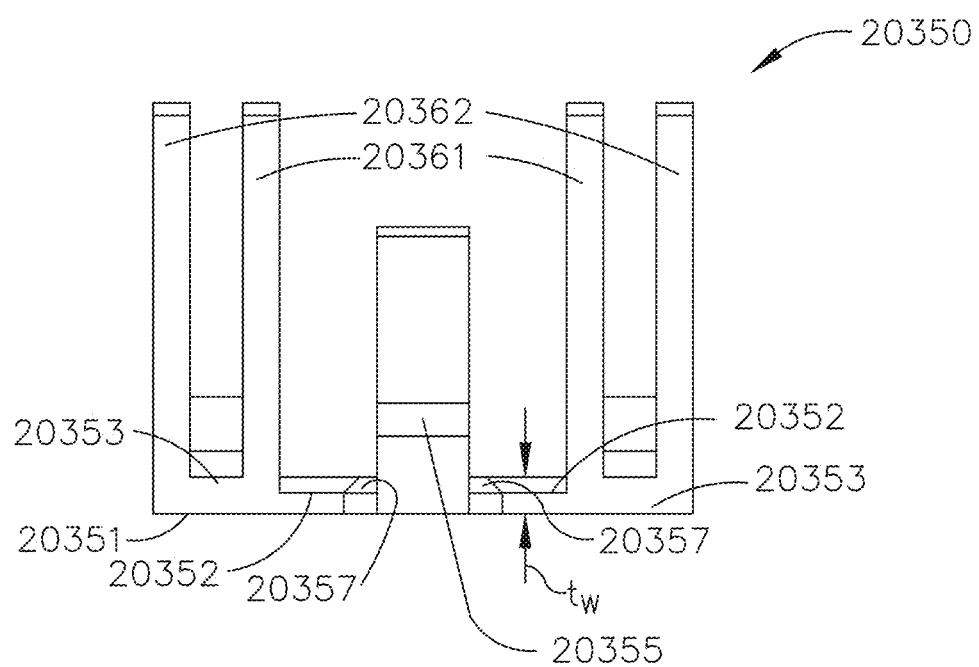
Figure 11:
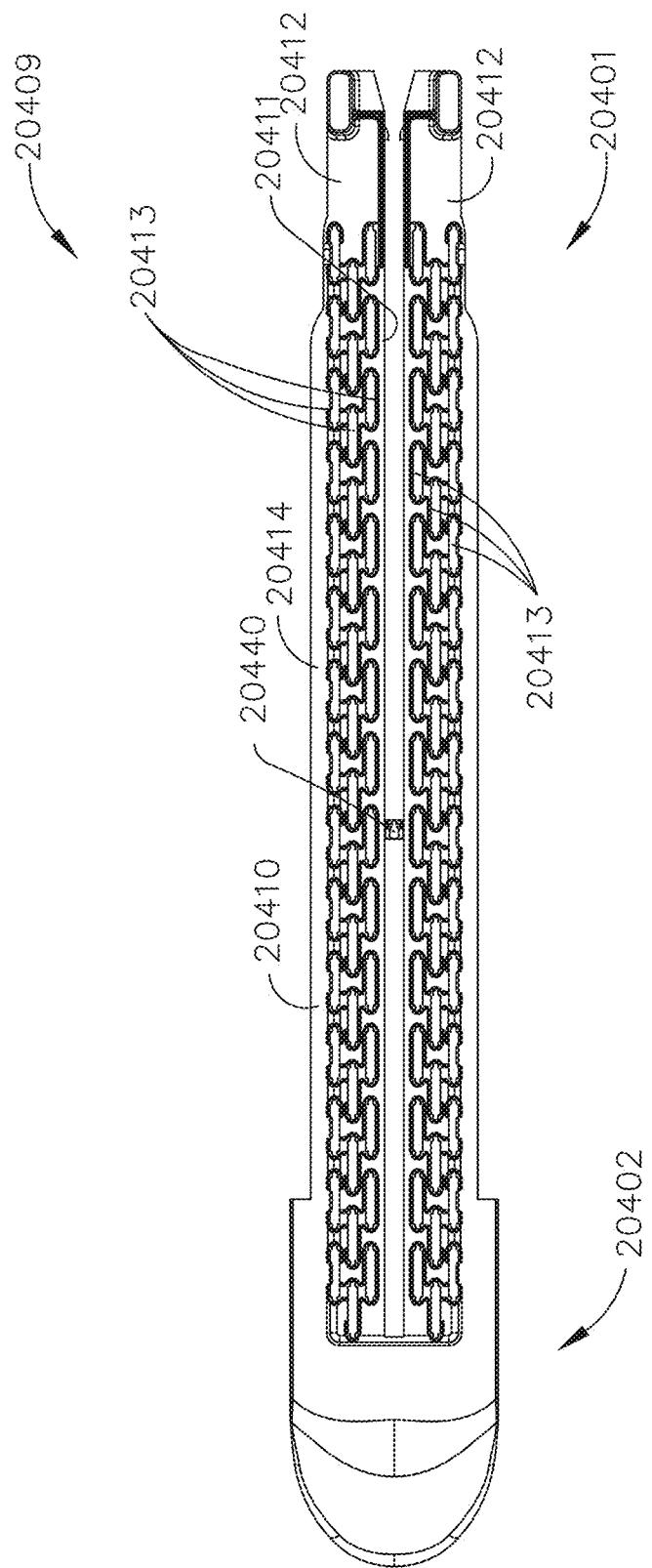
Figure 12:
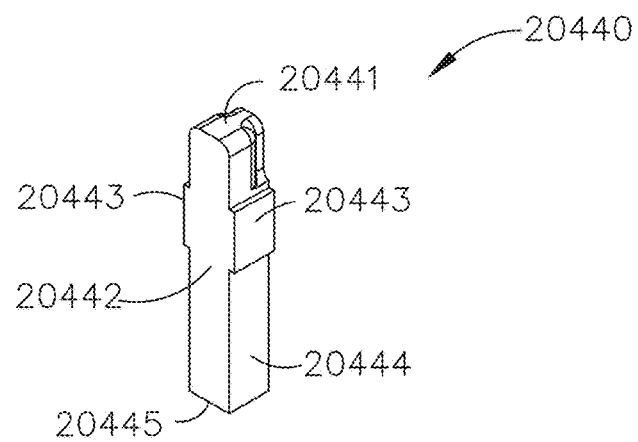
Figure 13:
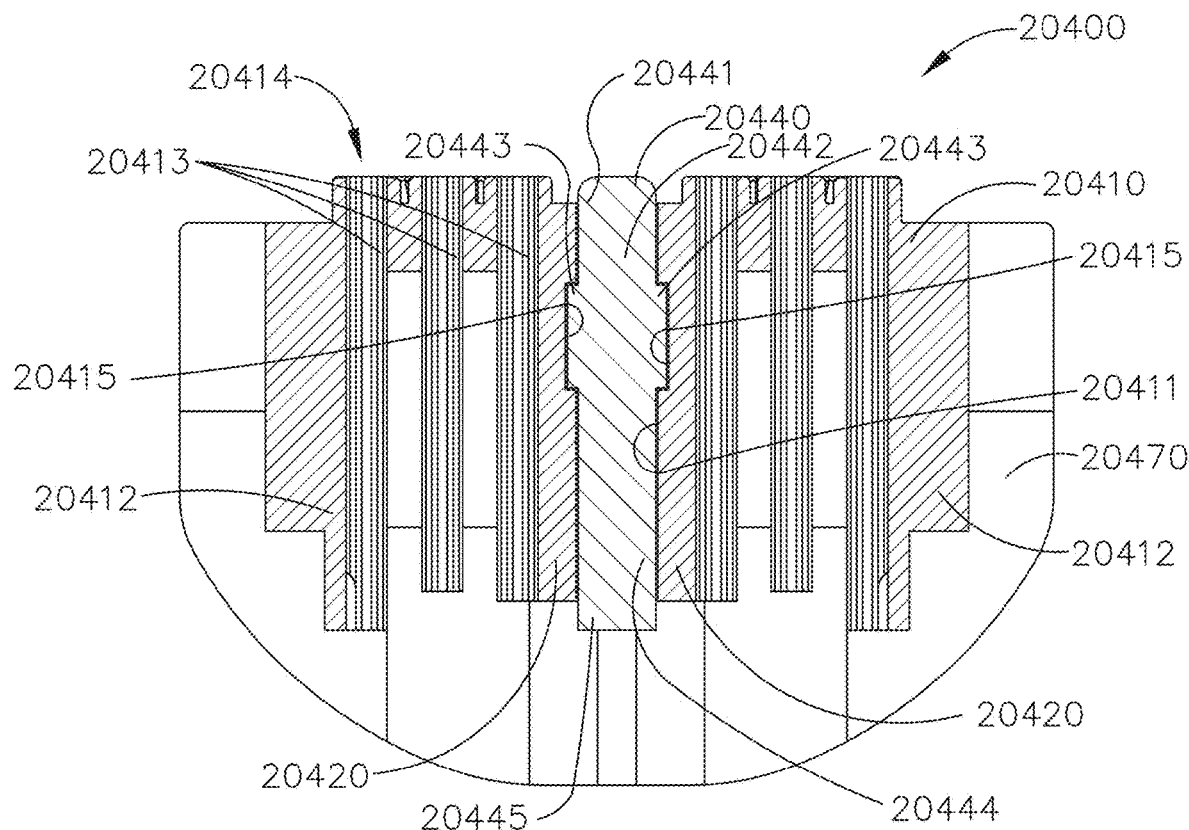
Figure 14:
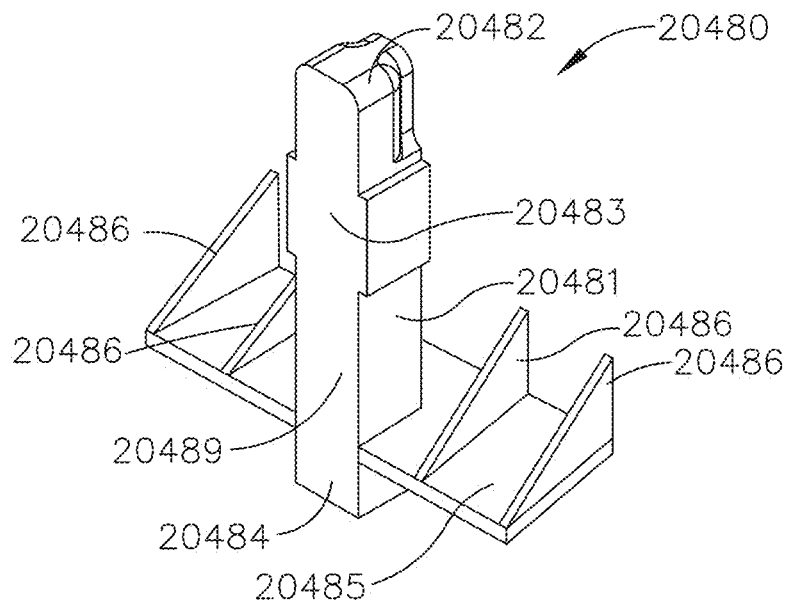
Figure 16:
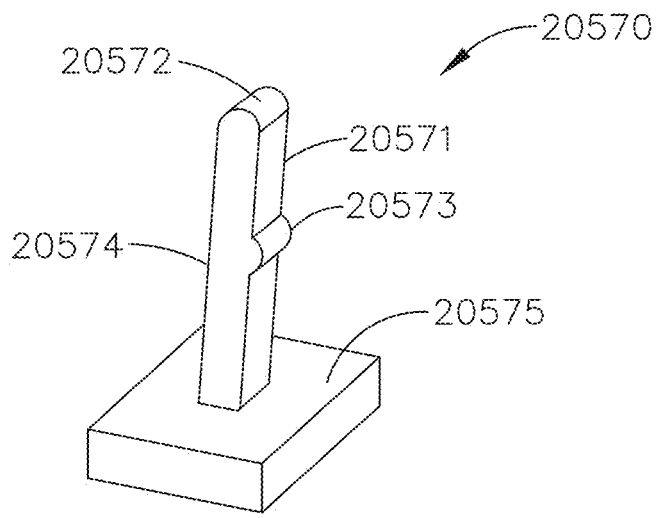
Figure 15:
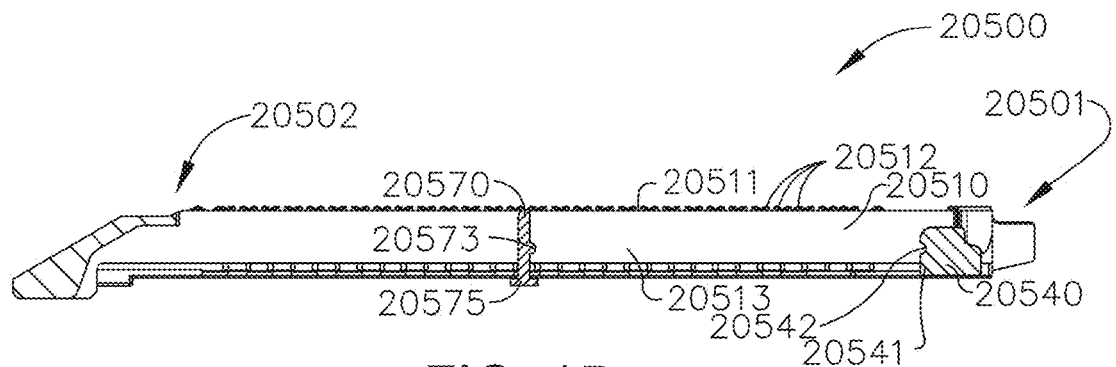
Figure 17:
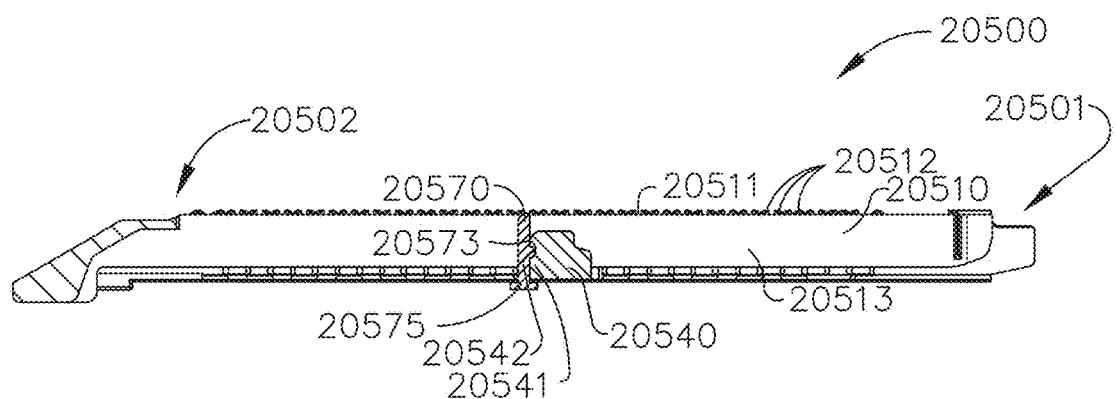
Figure 18:
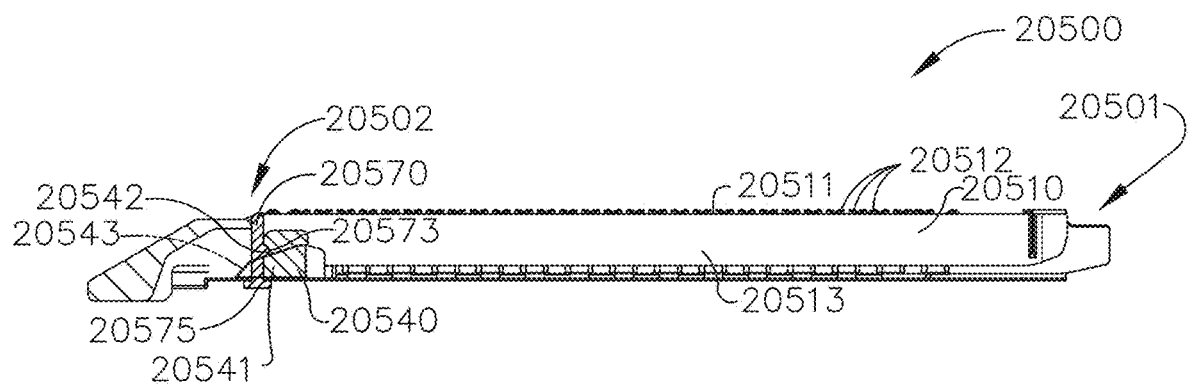
Figure 19:
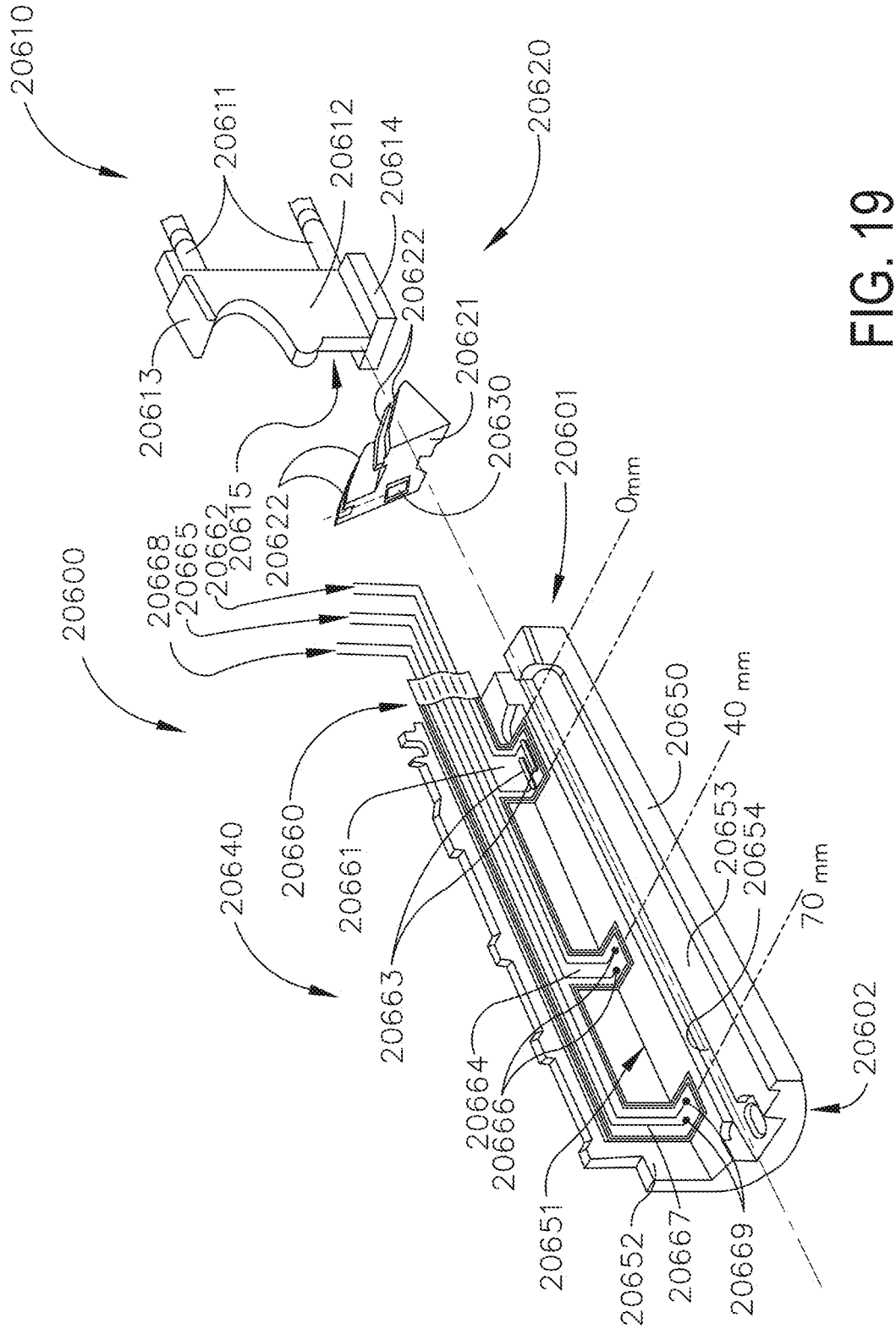
Figure 20:
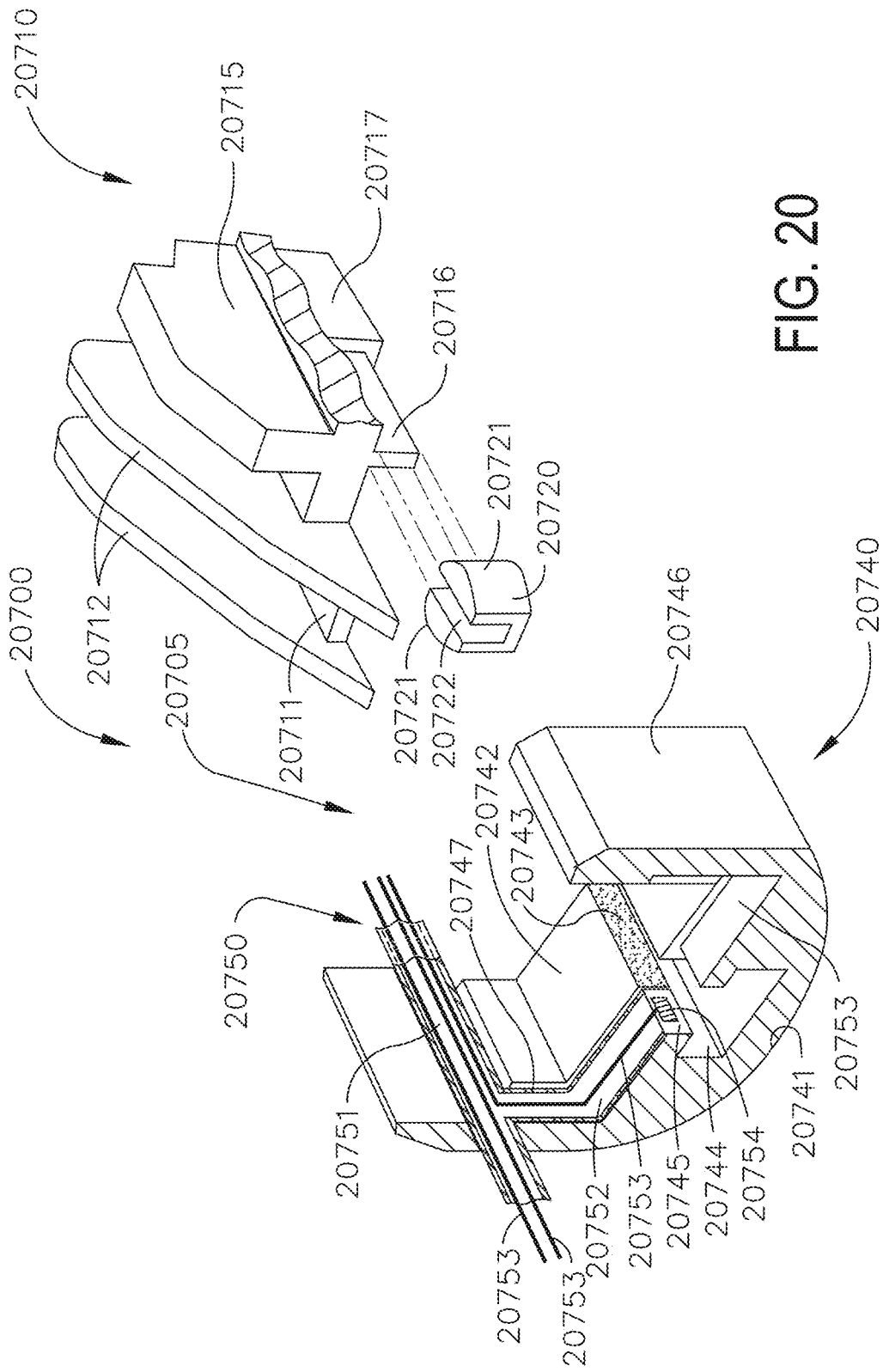
Figure 21:
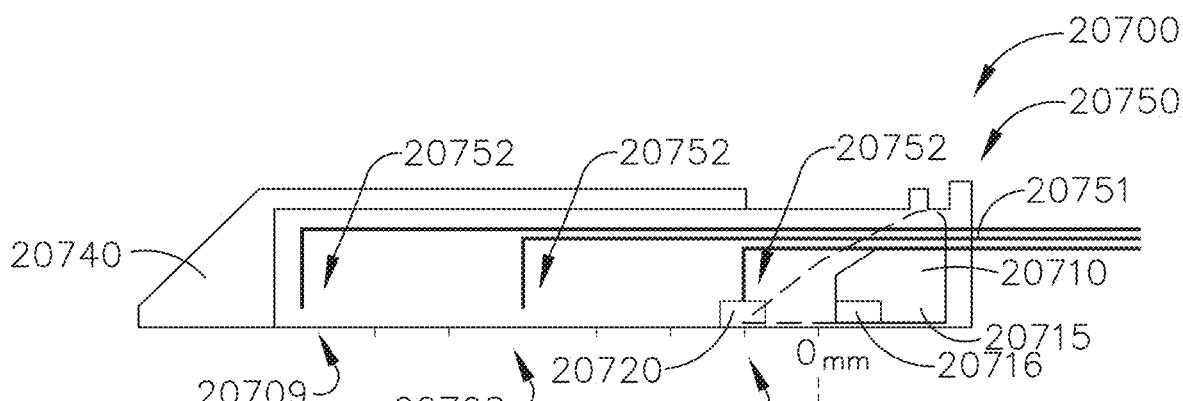
Figure 22:
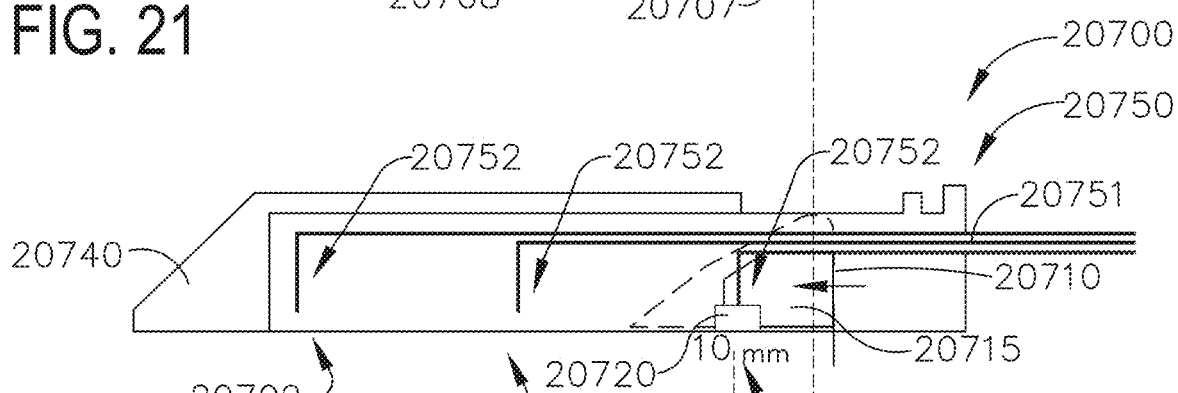
Figure 23:
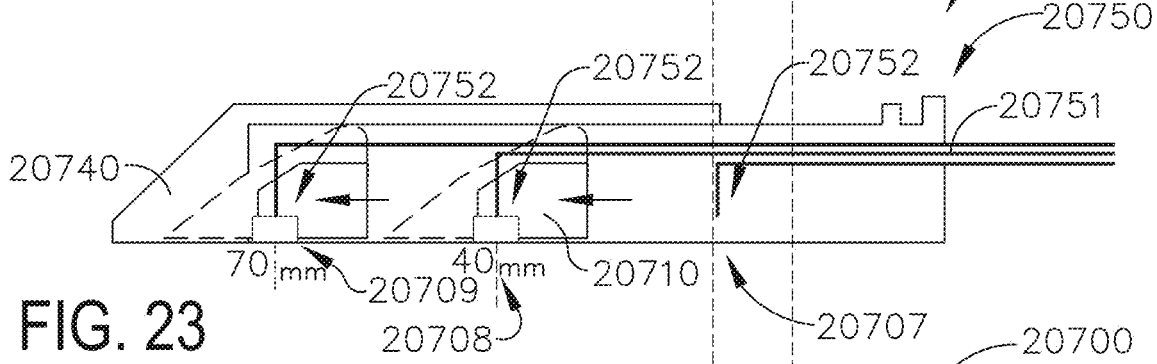
Figure 24:
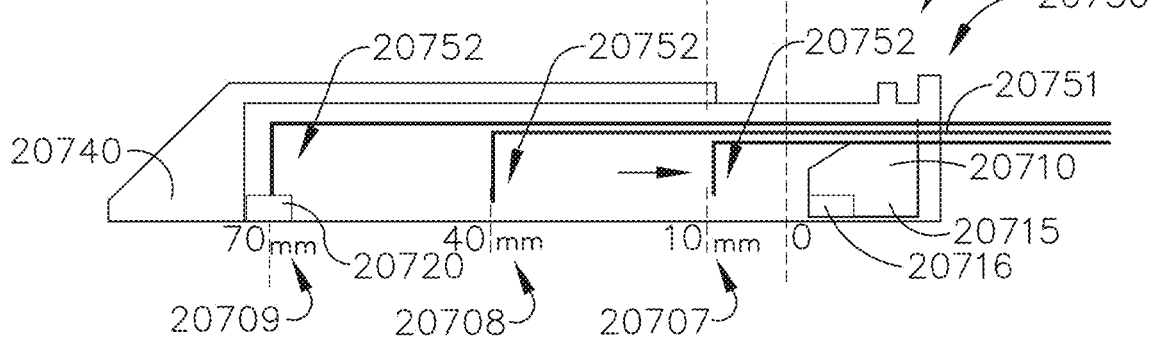
Figure 25:
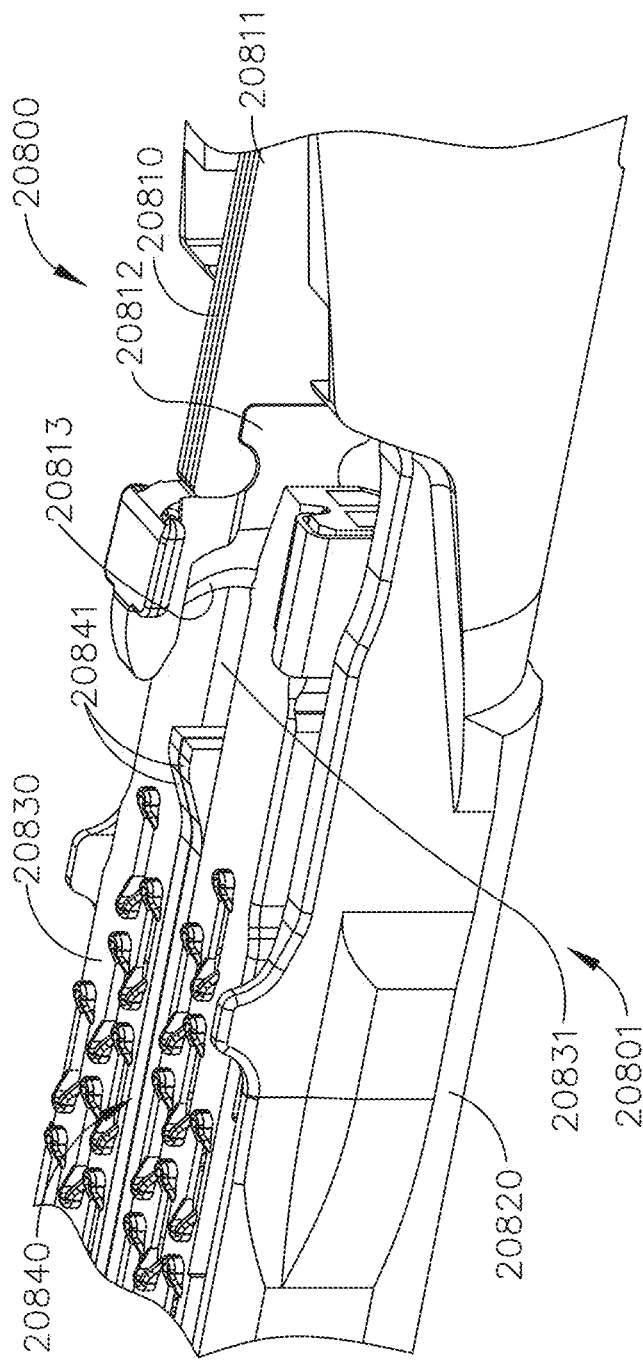
Figure 26:
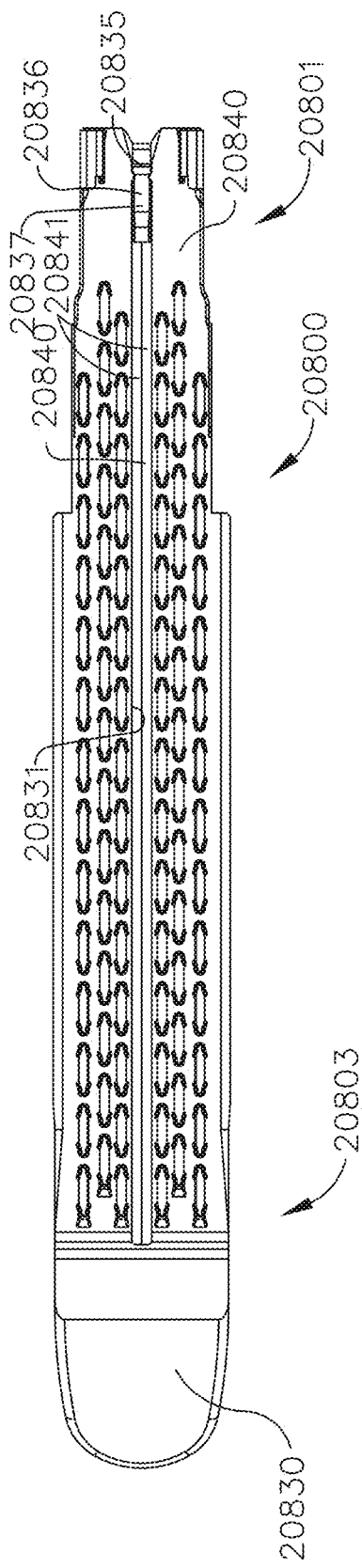
Figure 27:
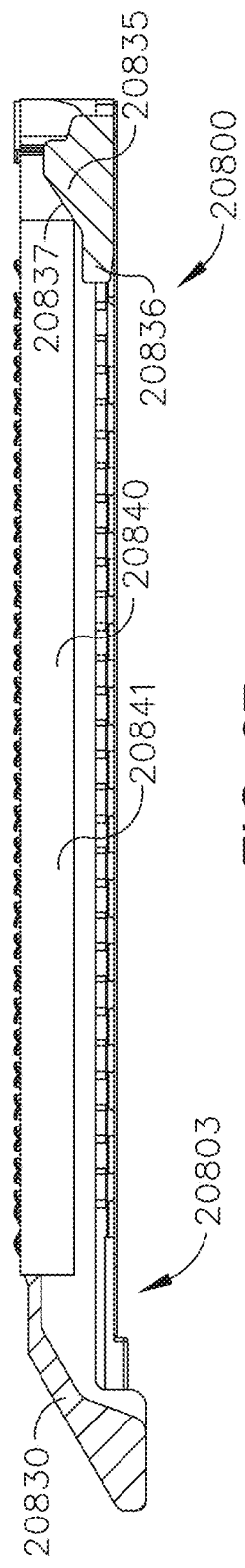
Figure 28:
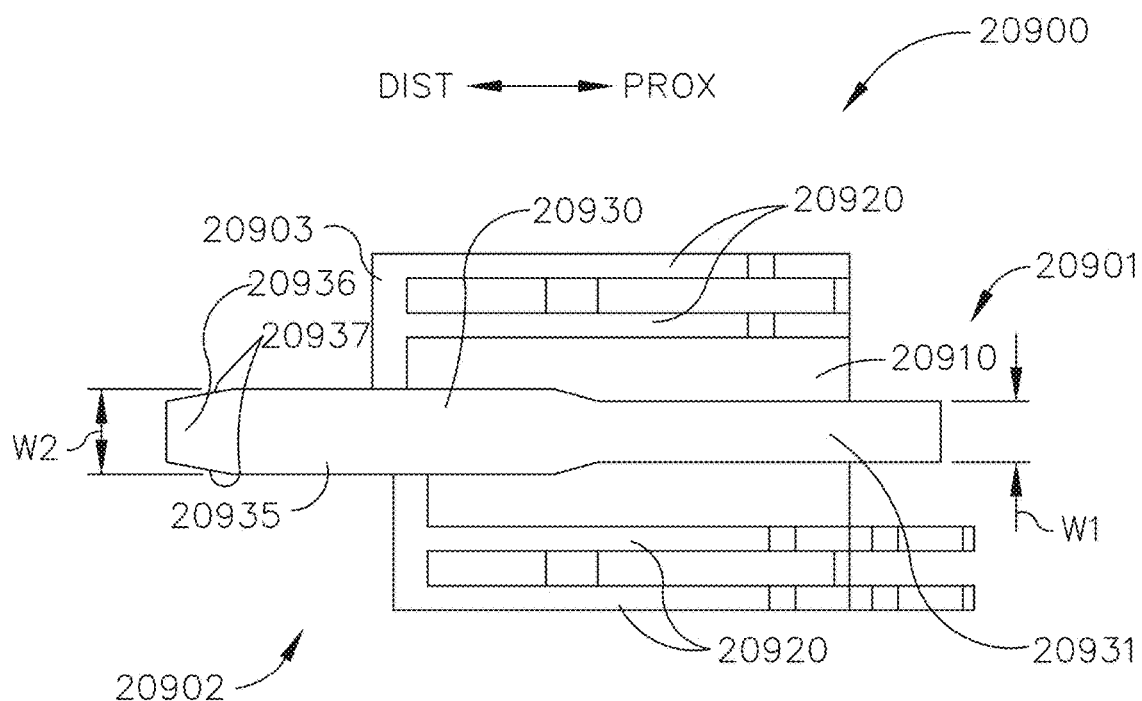
Figure 28A:
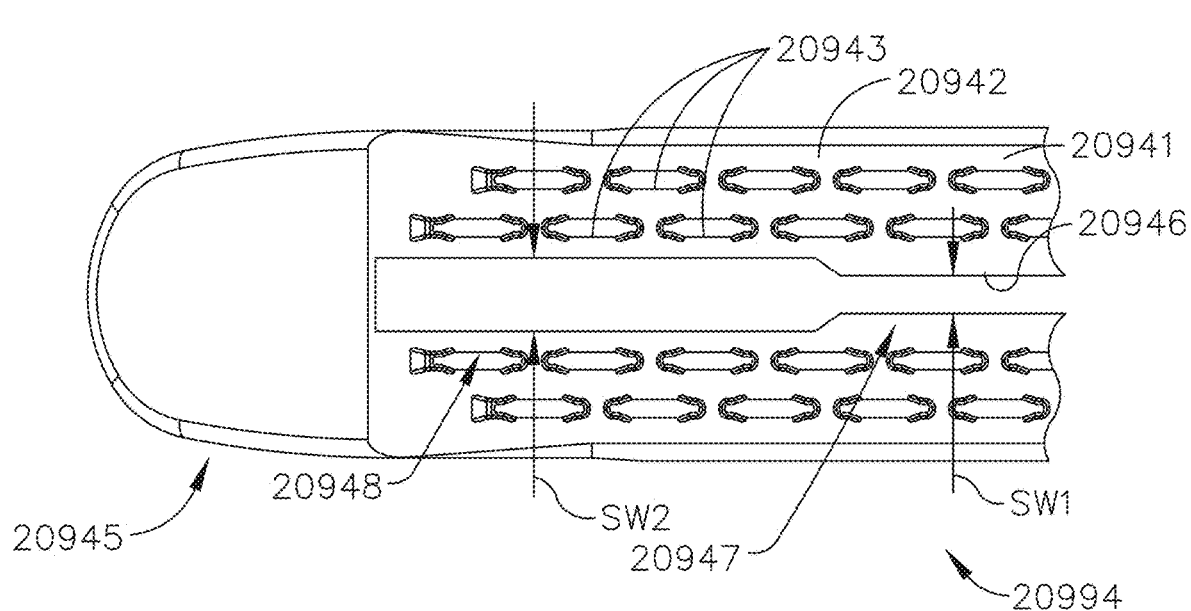
Figure 29:
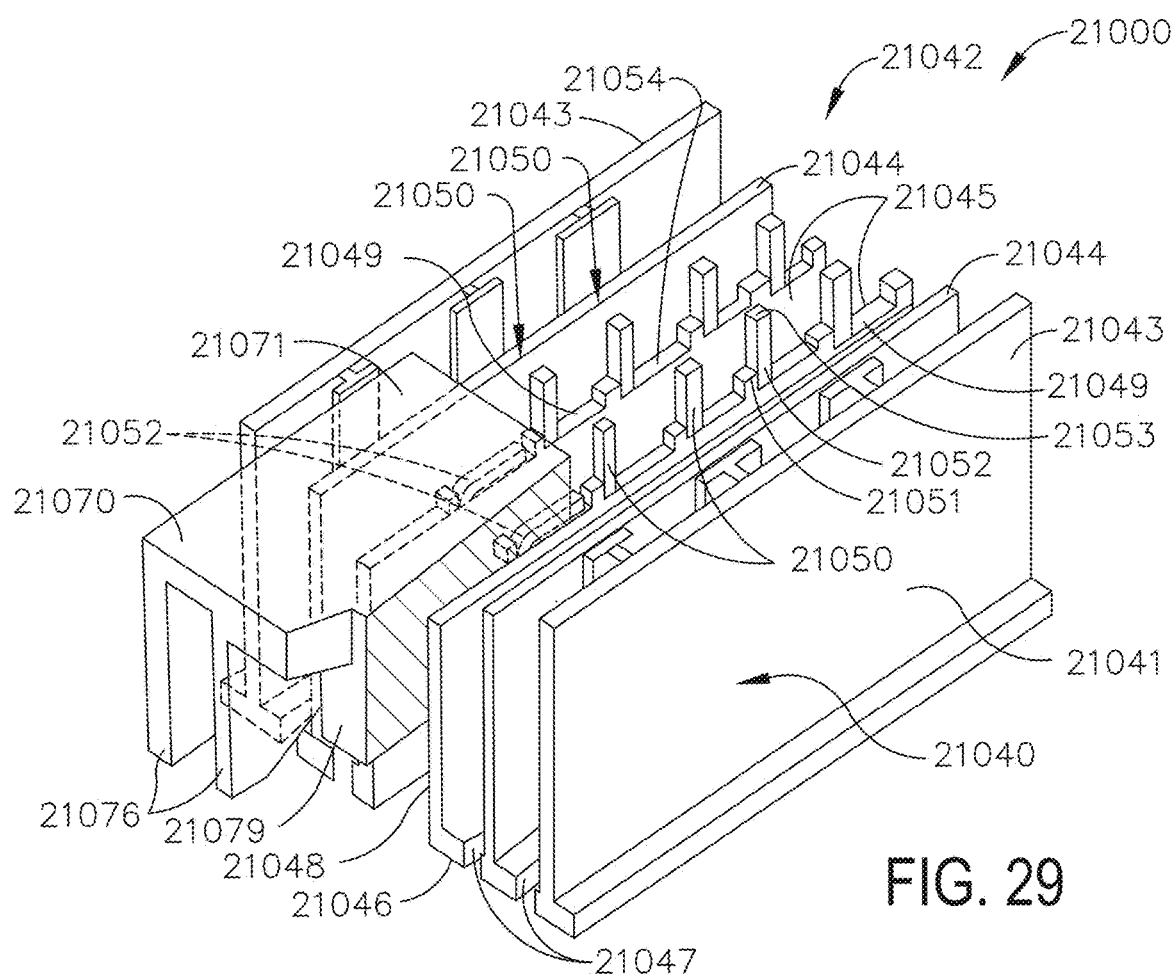
Figure 30:
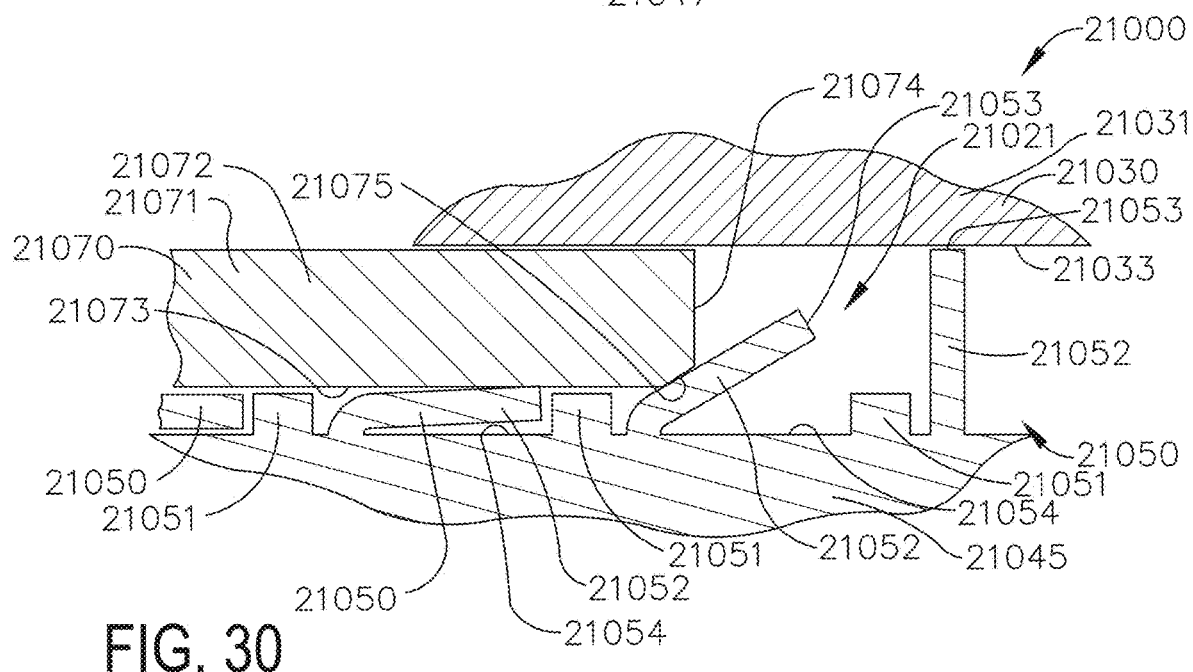

FIG. 4 is a partial perspective view of a staple cartridge for use with a surgical stapling end effector, wherein the staple cartridge comprises a plurality of outer staple cavities and a plurality of staple drivers configured to eject staples from the outer staple cavities, and wherein each outer staple cavity comprises a retention feature configured to hold one of the staple drivers in an unfired position;

FIG. 5 is a cross-sectional view of the staple cartridge of FIG. 4, wherein the staple drivers are illustrated in their unfired position;

FIG. 6 is a cross-sectional view of a staple cartridge assembly comprising a cartridge body and a sled, wherein the cartridge body comprises an inner cartridge wall comprising a varying height along the longitudinal length of the inner cartridge wall;

FIG. 7 is a perspective view of the sled of the staple cartridge assembly of FIG. 6;

FIG. 8 is a front view of the sled of FIG. 7;

FIG. 9 is a partial cross-sectional view of a proximal zone of the staple cartridge assembly of FIG. 6, where the sled is in a proximal, unfired position;

FIG. 10 is a partial cross-sectional view of an intermediate zone of the staple cartridge assembly of FIG. 6, where the sled is positioned within the intermediate zone;

FIG. 11 is a top view of a staple cartridge assembly comprising a cartridge body having a longitudinal slot and a pre-positioned cartridge support pillar positioned within the longitudinal slot;

FIG. 12 is a perspective view of the cartridge support pillar of FIG. 11;

FIG. 13 is a cross-sectional view of the staple cartridge assembly of FIG. 11;

FIG. 14 is a perspective view of a cartridge support pillar for use with a staple cartridge assembly, wherein the cartridge support pillar comprises staple deployment ramps configured to fire the distal-most staples of a staple cartridge assembly;

FIG. 15 is a cross-sectional view of a staple cartridge assembly comprising a cartridge body, a sled, and a pre-positioned cartridge support pillar within a longitudinal slot of the cartridge body, wherein the sled is in a proximal, unfired position;

FIG. 16 is a perspective view of the cartridge support pillar of FIG. 15;

FIG. 17 is a cross-sectional view of the staple cartridge assembly of FIG. 15, wherein the sled is engaged with the pre-positioned cartridge support pillar;

FIG. 18 is a cross-sectional view of the staple cartridge assembly of FIG. 15, wherein the sled and the pre-positioned cartridge support pillar are positioned in a distal, fired position;

FIG. 18A is a side view of a stapling system comprising a staple cartridge, a cartridge channel, and a movable cartridge support positioned within the staple cartridge, wherein the stapling system further comprises a sensing system configured to sense a parameter of the stapling system;

FIG. 18B is a perspective view of the movable cartridge support of FIG. 18A;

FIG. 18C is a side view of the movable cartridge support of FIG. 18A;

FIG. 19 is a partial perspective view of a surgical stapling system comprising a firing assembly, a sled, a cartridge channel, and a flex circuit configured to detect the position of the sled during a firing stroke;

FIG. 20 is a partial, cross-sectional, perspective view of a surgical stapling assembly comprising a sled, a cartridge channel, and a sled detection system configured to detect the position of the sled during a firing stroke;

FIG. 21 is a schematic view of the surgical stapling assembly of FIG. 20, wherein the sled is in a proximal, unfired position and a conductive post of the sled detection system is in a pre-positioned home position in a proximal zone of the surgical stapling assembly;

FIG. 22 is a schematic view of the surgical stapling assembly of FIG. 20, wherein the sled is engaged with the conductive post in the pre-positioned home position;

FIG. 23 is a schematic view of the surgical stapling assembly of FIG. 20, wherein the sled is engaged with the conductive post in a plurality of fired positions;

FIG. 24 is a schematic view of the surgical stapling assembly of FIG. 20, wherein the sled is retracted into the proximal, unfired position and the conductive post is left in a distal end of the cartridge channel;

FIG. 25 is a perspective view of a surgical stapling assembly comprising a firing driver, a cartridge channel, and a staple cartridge assembly, wherein the staple cartridge assembly comprises a deployable support positioned within a longitudinal slot of the staple cartridge assembly;

FIG. 26 is a top view of the staple cartridge assembly of FIG. 25;

FIG. 27 is a side view of the staple cartridge assembly of FIG. 25;

FIG. 28 is a top view of a sled for use with a surgical stapling assembly, wherein the sled comprises a central portion comprising a proximal end and a distal end, and wherein distal end is thicker than the proximal end;

FIG. 28A is a top view of a staple cartridge assembly for use with the sled of FIG. 28;

FIG. 29 is a partial perspective view of a surgical stapling assembly comprising a staple cartridge assembly, wherein the staple cartridge assembly comprises a cartridge body and a sled, and wherein the cartridge body comprises a plurality of support pillars configured to be hinged out of the way by the sled during a firing stroke;

FIG. 30 is a cross-sectional view of the surgical stapling assembly of FIG. 29, wherein the surgical stapling assembly further comprises a cartridge channel comprising an opposing support surface and a cavity through which the sled is configured to travel during the firing stroke;

FIG. 31 is a cross-sectional view of the surgical stapling assembly of FIG. 29, wherein a pair of opposing support pillars are in a fully-extended configuration; and FIG. 32 is a cross-sectional view of the surgical stapling assembly of FIG. 29, wherein the pair of opposing support pillars shown in FIG. 31 are in a fully-collapsed configuration.

Corresponding reference characters indicate corresponding parts throughout the several views.

DETAILED DESCRIPTION

Applicant of the present application owns the following U.S. Patent Applications that were filed on Oct. 13, 2023 and which are each herein incorporated by reference in their respective entireties:

U.S. patent application Ser. No. 18/379,759, titled METHOD OF OPERATING A SURGICAL STAPLING INSTRUMENT;

U.S. patent application Ser. No. 18/379,762, titled SURGICAL STAPLING SYSTEMS WITH ADAPTIVE STAPLE FIRING ALGORITHMS;

U.S. patent application Ser. No. 18/379,763, titled LEARNED TRIGGERS FOR ADAPTIVE CONTROL OF SURGICAL STAPLING SYSTEMS;

U.S. patent application Ser. No. 18/379,766, titled CONTROL CIRCUIT FOR ACTUATING MOTORIZED FUNCTION OF SURGICAL STAPLING INSTRUMENT UTILIZING INERTIAL DRIVE TRAIN PROPERTIES;

U.S. patent application Ser. No. 18/379,768, titled PROPORTIONATE BALANCING OF THE FUNCTION IMPACT MAGNITUDE OF BATTERY OUTPUT TO PEAK MOTOR CURRENT;

U.S. patent application Ser. No. 18/379,771, titled MOTOR OPTIMIZATION BY MINIMIZATION OF PARASITIC LOSSES AND TUNING MOTOR DRIVE CONFIGURATION;

U.S. patent application Ser. No. 18/379,771, titled APPARATUS AND METHOD TO REDUCE PARASITIC LOSSES OF THE ELECTRICAL SYSTEM OF A SURGICAL INSTRUMENT;

U.S. patent application Ser. No. 18/379,776, titled SURGICAL TOOL WITH RELAXED FLEX CIRCUIT ARTICULATION;

U.S. patent application Ser. No. 18/379,777, titled WIRING HARNESS FOR SMART STAPLER WITH MULTI AXIS ARTICULATION;

U.S. patent application Ser. No. 18/379,781, titled SURGICAL SYSTEM WITH WIRELESS ARRAY FOR POWER AND DATA TRANSFER; and U.S. patent application Ser. No. 18/379,784, titled SURGICAL STAPLE CARTRIDGE COMPRISING REPLACEABLE ELECTRONICS PACKAGE.

Applicant of the present application owns the following U.S. Patent Applications that were filed on-even date herewith Oct. 13, 2023 and which are each herein incorporated by reference in their respective entireties:

U.S. patent application Ser. No. 18/379,790, titled METHOD OF ASSEMBLING A STAPLE CARTRIDGE;

U.S. patent application Ser. No. 18/379,793, titled CONTROL SURFACES ON A STAPLE DRIVER OF A SURGICAL STAPLE CARTRIDGE;

U.S. patent application Ser. No. 18/379,801, titled STAPLE CARTRIDGE COMPRISING WALL STRUCTURES TO REDUCE CARTRIDGE DEFLECTION;

U.S. patent application Ser. No. 18/379,803, titled PANLESS STAPLE CARTRIDGE ASSEMBLY COMPRISING RETENTION FEATURES FOR HOLDING STAPLE DRIVERS AND SLED;

U.S. patent application Ser. No. 18/379,805, titled STAPLE CARTRIDGE COMPRISING A SLED HAVING A DRIVER LIFT CAM;

U.S. patent application Ser. No. 18/379,808, titled SURGICAL STAPLE CARTRIDGES WITH SLEDS CONFIGURED TO BE COUPLED TO A FIRING DRIVER OF A COMPATIBLE SURGICAL STAPLER;

U.S. patent application Ser. No. 18/379,810, titled STAPLE CARTRIDGE COMPRISING A COMPOSITE SLED;

U.S. patent application Ser. No. 18/379,811, titled SURGICAL INSTRUMENTS WITH JAW AND FIRING ACTUATOR LOCKOUT ARRANGEMENTS LOCATED PROXIMAL TO A JAW PIVOT LOCATION;

U.S. patent application Ser. No. 18/379,815, titled SURGICAL INSTRUMENTS WITH LATERALLY ENGAGEABLE LOCKING ARRANGEMENTS FOR LOCKING A FIRING ACTUATOR;

U.S. patent application Ser. No. 18/379,817, titled DUAL INDEPENDENT KEYED LOCKING MEMBERS ACTING ON THE SAME DRIVE MEMBER;

U.S. patent application Ser. No. 18/379,820, titled ADJUNCTS FOR USE WITH SURGICAL STAPLING INSTRUMENTS;

U.S. patent application Ser. No. 18/379,822, titled ADJUNCTS FOR USE WITH SURGICAL STAPLING INSTRUMENTS;

U.S. patent application Ser. No. 18/379,826, titled JAW CONTROL SURFACES ON A SURGICAL INSTRUMENT JAW;

U.S. patent application Ser. No. 18/379,827, titled ZONED ALGORITHM ADAPTIVE CHANGES BASED ON CORRELATION OF COOPERATIVE COMPRESSION CONTRIBUTIONS OF TISSUE;

U.S. patent application Ser. No. 18/379,831, titled STAPLE CARTRIDGES COMPRISING TRACE RETENTION FEATURES; and U.S. patent application Ser. No. 18/379,832, titled STAPLE CARTRIDGES COMPRISING STAPLE RETENTION FEATURES.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

Surgical stapling end effectors having jaws configured to clamp tissue therebetween can experience various loads within the surgical stapling end effector. Such loads can include bending loads, shear loads, and/or torsional loads, for example. These loads can be induced when the jaws are clamped onto patient tissue and/or during a staple firing stroke, for example. These loads can cause certain components of the surgical stapling end effectors to elastically deflect and/or twist, for example, from their original shape. Replaceable staple cartridges configured to be installed in a cartridge channel jaw of a surgical stapling end effector can be particularly vulnerable, or susceptible, to such loads and the resulting deflection and/or twisting. This vulnerability can be attributed to the material of the staple cartridge relative to the materials of the cartridge channel jaw and the opposing jaw such as, for example, an anvil jaw. The staple cartridge can include a cartridge body comprised of plastic while the cartridge channel jaw and the anvil jaw may be comprised of metal and, owing to differences in the elasticity, flexibility, and/or strength of such materials, the staple cartridge may be more likely to elastically deflect, and/or twist, from its original shape under certain loads. Moreover, this vulnerability can also be attributed to the nature of how the components of a surgical stapling end effector fit together. A surgical stapling end effector can include a longitudinally translatable cutting edge, or knife, that traverses a longitudinal slot defined in the staple cartridge to cut tissue clamped between the jaws. Depending on the configuration of the longitudinal slot, the longitudinal slot can reduce the strength of the staple cartridge and increase how much the staple cartridge, and/or portions of the staple cartridge, can twist or deflect from its original shape under load. A surgical stapling end effector can include a translatable sled comprising ramped wedges configured to eject staples from the staple cartridge during the staple firing stroke. The sled may comprise a base portion that requires space to translate through the stapling end effector. This space, often times located between the cartridge body and a cartridge pan attached to the cartridge body, for example, or between a cartridge body and the cartridge channel jaw where a cartridge pan is not present, can provide a void into which portions of the staple cartridge can deflect.

For at least the reasons discussed above, staple cartridges can be prone to collapsing. In accordance with the present disclosure, a staple cartridge may collapse when the two lateral sides of the staple cartridge-one on each side of the longitudinal slot-torque, deflect, and/or bend inwardly toward the longitudinal slot. Such deflection of the lateral sides can cause the staple cavities defined in the lateral sides to become unregistered with, or misaligned with respect to, the corresponding staple forming pockets defined in the anvil. Such deflection can also cause binding between the various components of the end effector such as, for example, the staple drivers and the staple cavities, the I-beam and the longitudinal slot of the staple cartridge, and the sled and the cartridge body, among others. Such binding can increase the force required to staple and cut the patient tissue and even prevent the staple firing stroke from being completed. Such deflection may also cause tissue to bunch up near the longitudinal slot which can increase the difficultly of cutting the tissue during the staple firing stroke.

Figure 1:
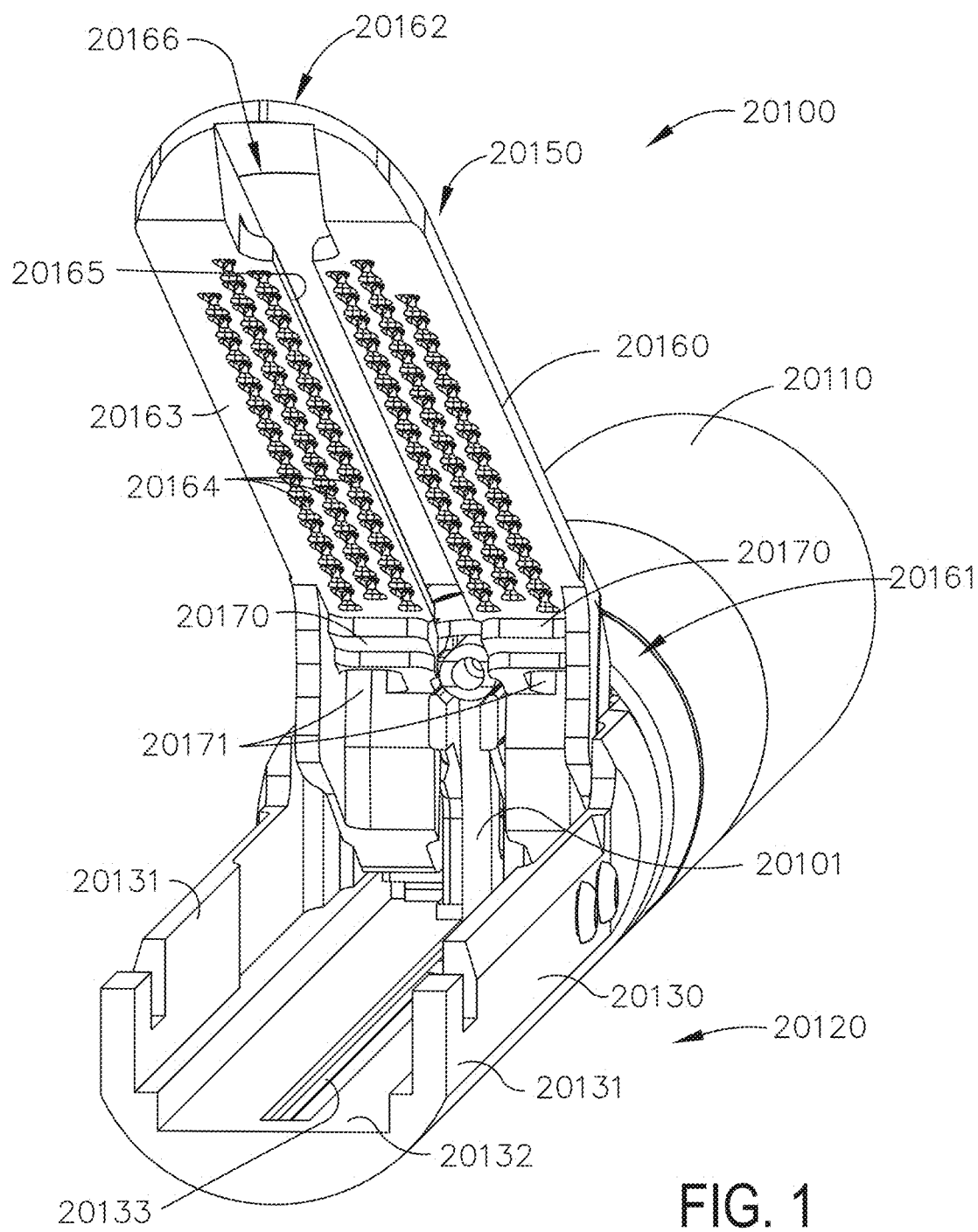
FIG. 1 is a perspective view of a surgical stapling end effector comprising a shaft, a first jaw, and a second jaw movable relative to the first jaw to clamp tissue between the first jaw and the second jaw.
Figure 2:
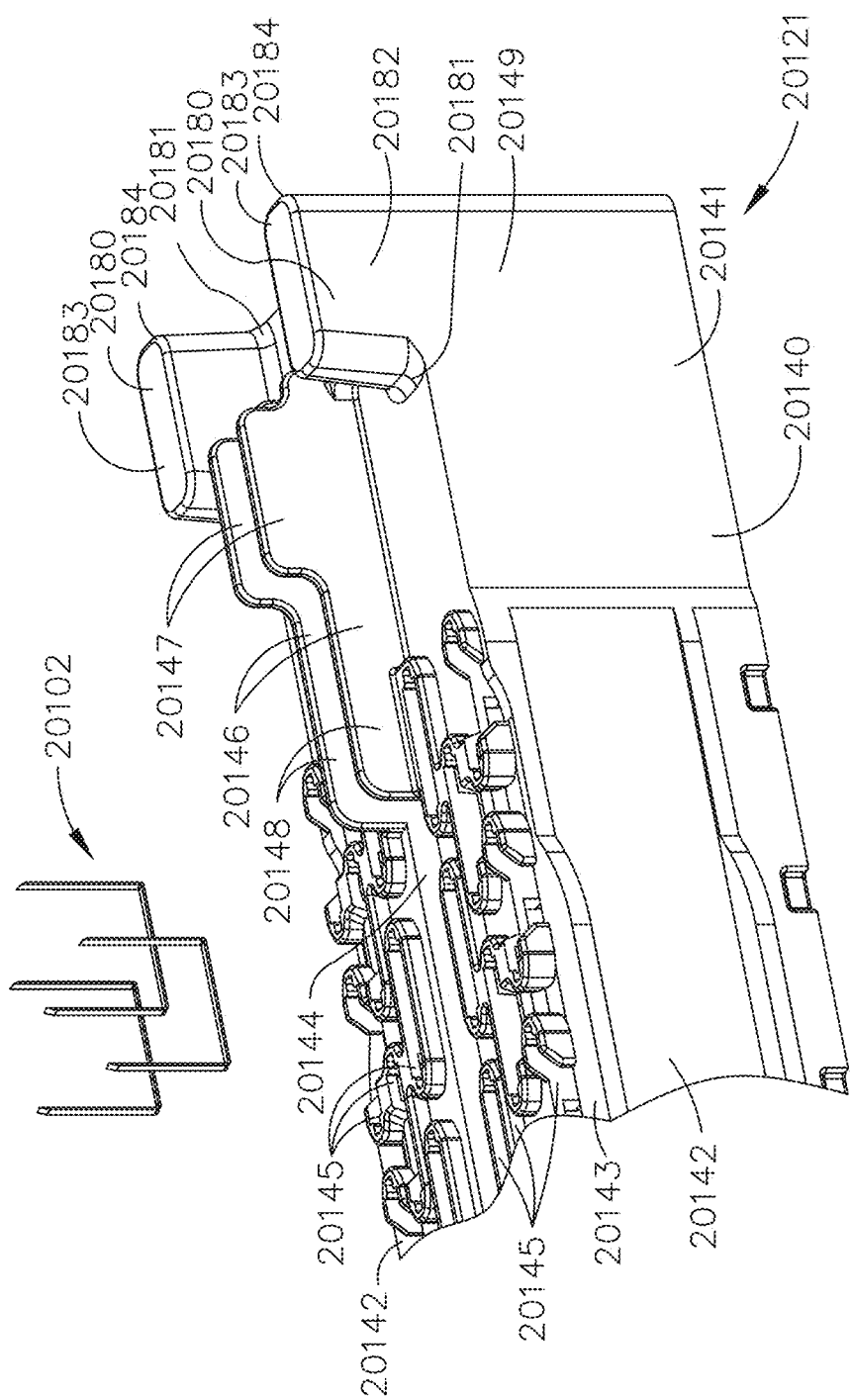
FIG. 2 is a partial perspective view of a proximal end of a staple cartridge of the surgical stapling end effector of FIG. 1, wherein the staple cartridge is configured to be installed into the first jaw.
Figure 3:
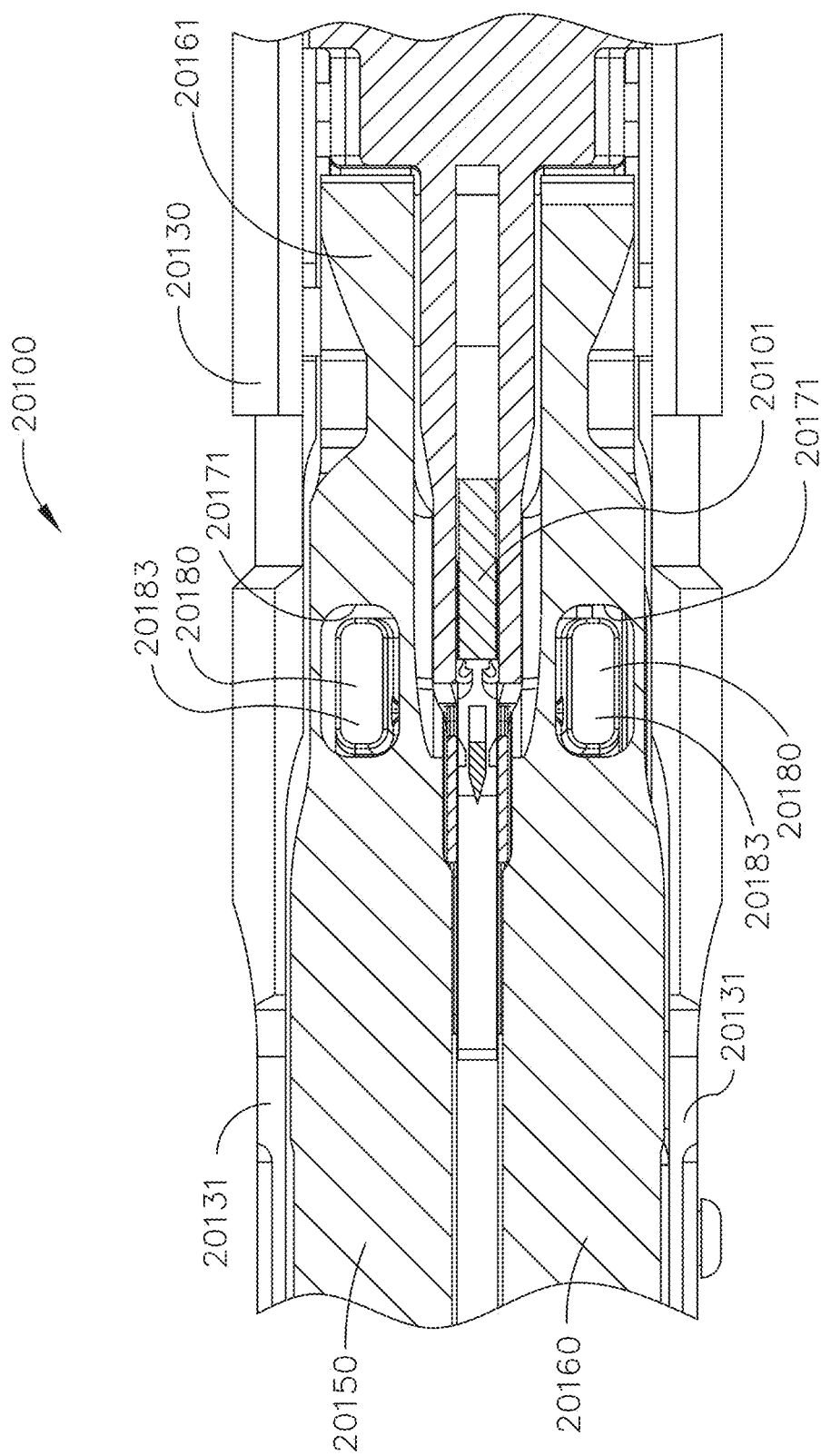
FIG. 3 is a partial cross-sectional view of the surgical stapling end effector of FIG. 1 where the staple cartridge is installed in the first jaw and the second jaw is positioned in a fully clamped position.

FIGS. 1-3 depict a surgical stapling end effector 20100 configured to clamp, cut, and staple patient tissue. As discussed in greater detail further below, the surgical stapling end effector 20100 is configured to inhibit the deflection of a staple cartridge. The surgical stapling end effector 20100 comprises a shaft assembly 20110, a first jaw 20120, and a second jaw 20130 pivotable relative to the first jaw 20120 to clamp tissue therebetween. The first jaw 20120 and the second jaw 20130 are supported within the shaft assembly 20110. The first jaw 20120 is non-pivotable; however, the first jaw 20120 can be pivotable instead of the second jaw 20130. In accordance with the present disclosure, the first jaw 20120 and the second jaw 20130 can both be pivotable relative to each other. Details of various surgical stapling assemblies, components, and systems can be seen in U.S. Patent Application Publication No. 2021/0059672, which is hereby incorporated by reference in its entirety herein.

The first jaw 20130 comprises a cartridge channel 20130 and a staple cartridge 20140. The staple cartridge 20140 is replaceable and can be removed and replaced with a new staple cartridge during a surgical procedure. The cartridge channel 20130 comprises a bottom portion 20132 and channel walls 20131 extending upwardly from the bottom portion 20132. The bottom portion 20132 comprises a slot 20133 defined therein configured to receive at least a portion of a distal head portion 20101 of a firing driver during a firing stroke (such as a camming pin of a distal I-beam head, for example). The firing driver, as discussed herein, can comprise any suitable component or combination of components. For example, the firing driver can comprise a motor, a rod, a firing shaft, any firing drive component, a distal I-beam head or E-beam head, a firing driver, a cutting edge, a cartridge sled, and/or staple drivers.

The second jaw 20150 is pivotable relative to the first jaw 20130 by way of a pin, for example. The second jaw 20150 comprises an anvil 20160 configured to form the staples 20102 ejected from the staple cartridge 20140. The anvil 20160 comprises a proximal end 20161, a distal end 20162, and a cartridge-facing anvil surface 20163. Tissue is configured to be clamped between the cartridge-facing anvil surface 20163 and the staple cartridge 20140 when the anvil 20160 is moved into a clamped position. Moreover, the anvil 20160 can be moved toward the staple cartridge 20140 during the firing stroke by the distal head portion 20101 which can include, for example, an I-beam. The anvil 20160 further comprises a plurality of staple forming pockets 20164 defined in the cartridge-facing anvil surface 20163 and a slot 20165 through which at least a portion of the distal head portion 20101 is configured to be received. The slot 20165 comprises an open proximal end an open distal end 20166; however, the distal end 20166 can be closed.

The staple cartridge 20140 comprises a cartridge body 20141 comprising two sides 20142 defined by a longitudinal slot 20144 defined in the cartridge body 20141. The longitudinal slot 20144 is configured to receive at least a portion of the distal head portion 20101 during a firing stroke. The longitudinal slot 20144 extends from a proximal end 20121 of the staple cartridge 20140 toward a distal end of the staple cartridge 20140. The longitudinal slot 20144 comprises an open end at the proximal end 20121 of the staple cartridge 20140 and a closed end at the distal end of the staple cartridge 20140. The cartridge body 20141 further comprises a deck surface 20143 and a plurality of staple cavities 20145 defined in the deck surface 20143. The staple cavities 20145 are arranged in a plurality of longitudinal rows. Each staple cavity 20145 is configured to store a staple 20102 therein. The staples 20102 are configured to be sequentially ejected from the staple cavities 20145 during the firing stroke as the distal head portion 20101 moves from a proximal, unfired position to a fired position that is distal to the proximal, unfired position.

Referring primarily to FIG. 2, each side 20142 of the cartridge body 20141 further comprises a knife guard 20146 extending upwardly from the deck at the proximal end 20121 of the cartridge body 20141 adjacent the longitudinal slot 20144. Each knife guard 20146 comprises a proximal portion 20147 and a distal portion 20146. The proximal portion 20147 comprises a first longitudinal length and a first vertical height. The distal portion 20148 comprises a second longitudinal length and second vertical height. The first longitudinal length is shorter than the second longitudinal length and the first vertical height is greater than the second vertical height; however, the knife guards can have any suitable height and/or width. Moreover, other embodiments are envisioned in which the cartridge body 20141 does not have knife guards.

Each side 20142 of the cartridge body 20141 further comprises a projection 20180 extending toward the second jaw 20160 from the deck surface 20143 at the proximal end 20121 of the staple cartridge 20140. Discussed in greater detail below, the projections 20180 are configured to be received within corresponding cavities 20171 of support structures 20170 of the anvil 20160 when the end effector 20100 is in a clamped configuration. The projections 20180 are integrally formed with the cartridge body 20141. In accordance with the present disclosure, the cartridge body 20141 can be formed with the projections 20180 during an injection molding process. The projections 20180 may comprise a material that is different than the cartridge body 20141 and are attached to the cartridge body 20141 after the cartridge body 20141 is formed during an injection molding process. The projections 20180 may comprise a material that is different than the cartridge body 20141 and are integrally formed with the cartridge body 20141 during an insert molding process, for example. The projections 20180 comprise an elongate shape, but can comprise any suitable shape. Each projection 20180 comprises an outer wall 20182 that is flush with an outer wall 20149 of a cartridge body side 20142 of the cartridge body 20141. Each projection 20180 further comprises a filleted transition surface 20181 extending from the deck surface 20143 and a filleted transition surface 20184 extending from a top surface 20183 of the projection 20180. In accordance with the present disclosure, the filleted transition surfaces 20184 can aid in aligning, or guiding, the projections 20180 into the cavities 20171 defined in the anvil 20160 when the end effector 20100 is placed in a clamped configuration.

Referring to FIG. 1, the support structures 20170 of the anvil 20160 extend downwardly toward the deck surface 20143 of the cartridge body 20141 at the proximal end 20161 of the anvil 20160. Each cavity 20171 defined in each support structure 20170 is configured to receive one of the projections 20180 as the second jaw 20150 is moved into a clamped position (FIG. 3). The projections 20180 are circumferentially surrounded by the support structures 20170 when the projections 20180 are positioned within the cavities 20171. The projections 20180 are sized and configured such that they are closely received within the cavities 20171. When the staple cartridge 20140 experiences clamping and/or firing loads, for example, one or both of the projections 20810 can come into contact with the sidewalls of the cavities 20171 which resist and/or stop the deflection of the staple cartridge 20410, as a result, such a configuration can help prevent longitudinal, lateral, and vertical deflection of the staple cartridge 20140 when the staple cartridge 20140 experiences clamping and/or firing loads, for example.

In accordance with the present disclosure, the cartridge body 20141 can be more susceptible to deflection, for example, nearer the proximal end 20121 of the cartridge body 20141 owing to the longitudinal slot 20144 separating the sides of the cartridge body 20141. Thus, positioning the projections 20180 near the proximal end of the surgical stapling end effector 20100 can help reduce the deflection of the cartridge body 20141 near the proximal end 20121. The top surfaces 20183 of the projections 20810 can help reduce vertical deflection of the cartridge body 20141 by abutting against a corresponding surface of the support structure 20170. Each cavity 20171 and its surrounding cavity walls can be configured to help reduce lateral and/or longitudinal deflection of the cartridge body 20141.

The projections 20180 can be press-fit into the cavities 20171 when the second jaw 20150 is moved into a fully-clamped position. The projections 20180 may come into contact with the walls of the cavities 20171 when the second jaw 20150 is closed. The walls of the cavities 20171 may provide immediate deflection support to the cartridge body 20141 once the second jaw 20150 is closed. The projections 20180 may not contact cavity walls of the cavities 20171 when the second jaw 20150 is moved into a fully-clamped position; however, the projections 20180 can come into contact with cavity walls of the cavities 20171 when the cartridge body 20141 deflects causing the projections 20180 to engage the cavity walls of the cavities 20171 which supports the cartridge body 20141. The projections 20180 may comprise ramped or angled front walls configured to provide a lead in surface to accommodate the pivoting motion of the second jaw 20150 into the fully clamped position. The cavities 20171 may comprise a ramped front cavity wall corresponding to a ramped front wall of the projections 20180.

FIGS. 4 and 5 depict a staple cartridge 20200 configured to be installed in a cartridge channel of a surgical stapling end effector. The staple cartridge 20200 comprises a cartridge body 20210 and a plurality of staple drivers 20250 configured to eject staples from the staple cartridge 20200, as discussed further below. The cartridge body 20210 comprises a longitudinal slot 20211 defined by walls 20213, two sides 20220 defined by the longitudinal slot 20211, and a deck surface 20212. Each side 20220 comprises a plurality of staple cavities arranged in longitudinal rows. Each staple cavity is configured to removably store a staple therein. The staple cavities comprise inner staple cavities 20221, intermediate staple cavities 20222, and outer staple cavities 20223. The inner staple cavities 20221 are adjacent the longitudinal slot 20211. The intermediate staple cavities 20222 are positioned between the outer staple cavities 20223 and the inner staple cavities 20221. The outer staple cavities 20223 are positioned adjacent an outer cartridge wall 20215 of the cartridge body 20210. The cartridge body 20210 further comprises intermediate cartridge walls 20214 that extend longitudinally adjacent the intermediate staple cavities 20222.

Each staple driver 20250 is configured to eject three staples from the staple cavities when the staple driver 20250 is lifted vertically toward the deck surface 20212 from an unfired position (FIG. 5)—one staple from an inner staple cavity 20221, one staple from an intermediate staple cavity 20222, and one staple from an outer staple cavity 20223. Other embodiments are envisioned, however, in which a staple driver is configured to eject less than three staples or more than three staples. To help prevent the staple drivers 20250 from falling out of the bottom of the cartridge body 20210, the cartridge body 20210 further comprises retention features 20240 defined in the outer cartridge walls 20215. The retention features 20240 extend into each outer staple cavity 20223 and prevent the staple drivers 20250 from falling out of the bottom of the cartridge body 20210 from their unfired position (FIG. 5). Each staple driver 20250 comprises an inner support column 20251 positioned within an inner staple cavity 20221, an intermediate support column position within an intermediate staple cavity 20222, and an outer support column 20253 positioned within an outer staple cavity 20223. The outer support column 20253 comprises a bottom surface 20254 configured to rest on a retention feature 20140, as discussed in greater detail below.

Each retention feature 20240 comprises an inwardly facing shelf 20241. The shelf 20241 comprises a bottom lead-in edge 20243, a vertical surface 20242 extending from the lead-in edge 20243, and a shelf ledge surface 20244 extending from the vertical surface 20242. The shelf ledge surface 20244 is configured to prevent a corresponding staple driver 20250 from falling out of the bottom of the cartridge body 20210 from its unfired position (FIG. 5). The bottom surface 20254 can be configured to rest on the shelf ledge surface 20244 when the staple driver 20250 is in its unfired position.

The bottom lead-in edge 20243 is configured to permit insertion of the staple driver 20250 into the bottom of the cartridge body 20210 and into the staple cavities 20221, 20222, 20223. The retention feature 20240 can be configured to deflect at least enough to allow for the staple driver 20250 to be positioned above the shelf ledge surface 20244 at which point the retention feature 20240 and outer cartridge wall 20215 can elastically assume its original shape and, thus, hold the staple driver 20250 in its unfired position. Each retention feature 20240 may comprise an asymmetric, or non-uniform, profile with a holding ledge at the top of the retention feature 20240 and a bottom lead-in edge at the bottom of the retention feature 20240.

In accordance with the present disclosure, the retention features 20240 can allow for the staple cartridge 20200 to be reloaded and/or re-assembled, for example, where the staple drivers 20250 inadvertently fall out of the bottom of the staple cartridge 20200, for example. The retention features 20140 can be formed using thermoplastic staking, or heat staking, for example. The staple drivers 20250 can be inserted into the staple cavities through the bottom of the cartridge body 20211 after forming the retention features 20140 with thermoplastic staking. Each of the retention features 20240 can be configured to be received within a corresponding retention cavity defined in the outer support column 20253 of a staple driver 20250 which releasably holds the staple driver 20250 in its unfired position. The staple drivers 20250 can be snap-fit into engagement with the retention features 20140 so as to hold the staple drivers 20250 in their unfired positions.

The bottom of the cartridge body 20210 comprises the bottom of the bottom of the staple cartridge 20200. The staple cartridge 20200 does not have a cartridge pan or retainer that is attached to the cartridge body 20210 that at least partially extends around the bottom of the cartridge body 20210 to prevent the staple drivers 20250 from falling out of the bottom of the cartridge body 20210. Without such a pan, the overall height of the staple cartridge 20200 can be shorter thereby saving room in the end effector. That said, the staple cartridge 20200 could comprise a cartridge pan in addition to or in lieu of the retention features 20140.

With regard to staple cartridges not having a pan attached to the cartridge body, further to the above, a space or gap may be present between the cartridge body and the jaw channel that receives the staple cartridge. This space allows a sled, for example, to move distally between the staple cartridge and the jaw channel during a firing stroke where a base portion of the sled, for example, passes underneath the cartridge body. The jaw channel may comprise a supporting surface for the sled. If a pan is attached to the cartridge body, a similar space or gap may be present between the cartridge body and the pan that permits a sled to move therebetween. The pan may comprise a supporting surface for the sled. In either event, the space or gap between the cartridge body and the supporting surface may permit the cartridge body to deflect under load, as discussed further below.

Tuning the fit between the sled, the cartridge body, and the supporting surface can help reduce the deflection of the staple cartridge, at least in certain areas, and can reduce the force needed to perform the staple firing stroke. The fit of the base portion within the space, or gap, can be tuned in specific areas, or zones, of the staple cartridge to help prioritize either the reduction of cartridge deflection under load (tighter fit of the base portion of the sled in the space) or lower firing forces (looser fit of the base portion of the sled in the space). In one or more areas, or zones, of the staple cartridge, it may be more advantageous to prioritize the reduction of cartridge deflection under load. In one or more other zones of the staple cartridge, it may be more advantageous to prioritize lower firing forces.

In accordance with the present disclosure, the vertical gap distance of the space defined between the sled and the support surface can be dimensioned such that the sled supports the staple cartridge and reduces the vertical and/or lateral deflection of the cartridge body under load. Further, in accordance with the present disclosure, there may be little, to no, clearance between the base portion of the sled, the cartridge body, and the support surface so that the base portion of the sled closely or tightly fits between the cartridge body and the support surface. The vertical gap distance of the space can be dimensioned so as to provide one or more other portions of the staple cartridge where the sled is less tightly fit between the cartridge body and the opposing support surface thereby reducing interference between components and reducing required to perform the staple firing stroke.

FIGS. 6-10 depict a staple cartridge assembly 20300 comprising a cartridge body 20310 including a deck surface 20311 and an inner cartridge wall 20315 adjacent a central longitudinal slot 20312 of the staple cartridge assembly 20300. The staple cartridge assembly 20300 comprises a proximal zone 20301, an intermediate zone 20302, and a distal zone 20303. In the proximal zone 20301, the inner cartridge wall 20315 does not extend all the way down to a support surface 20317 and, as a result, a gap is defined between the inner cartridge wall 20315 and the support surface 20317. Further to the above, the support surface 20317 can, for instance, be defined on a pan attached to the cartridge body 20310—where the staple cartridge assembly 20300 has a pan—or on the jaw channel of the stapling instrument. The inner cartridge wall 20315 comprises an overall height, i.e., first vertical wall height tW1, and a first vertical gap height tG1 is defined between the inner cartridge wall 20315 and the support surface 20317. The first vertical wall thickness tW1 is defined as the distance between the deck surface 20311 and a bottom 20316 of the inner cartridge wall 20315. The first vertical gap height tG1 is defined as the distance between the bottom 20316 of the inner cartridge wall 20315 and the support surface 20317.

The staple cartridge assembly 20300 further comprises a sled 20350 actuatable by a firing actuator, for example, distally through a firing stroke to eject staples from the staple cartridge assembly 20300. The sled 20350 comprises a base portion, or support base, 20351, inner ramped wedges 20361, and outer ramped wedges 20362. The ramped wedges 20361, 20362 extend upwardly from the base portion 20351. The ramped wedges 20361, 20362 are positioned within corresponding longitudinal cavities, or slots, of the cartridge body 20310 and are configured to sequentially lift staple drivers relative to the cartridge body as the sled 20350 is moved distally during the staple firing stroke. The sled 20350 further comprises a central nose 20355 comprising a distal end 20356 that moves within the central longitudinal slot 20312. The base portion 20351 comprises inner webs 20352 between the central nose 20355 and the inner ramped wedges 20361 and, also, outer webs 20353 between the inner ramped wedges 20361 and the outer ramped wedges 20362. The inner webs 20352 and the outer webs 20353 have different vertical thicknesses; however, the webs 20352 and 20353 can have the same vertical thickness. In either event, as discussed in greater detail below, a portion of the sled 20350 travels within the gap defined between the inner cartridge wall 20315 and the support surface 20317.

As can be seen in FIG. 9, further to the above, the inner web 20352 travels within the gap defined between the inner cartridge wall 20315 and the support surface 20317. The inner web 20352 is sized and configured such that there is a first clearance gap tCG1 between the top of the inner web 20352 and the bottom 20316 of the inner cartridge wall 20315. The first clearance gap tCG1 provides space for the inner web 20352 to pass underneath the cartridge body 20310 in the proximal zone 20301 so as to reduce contact, or frictional forces, between the sled 20350, cartridge body 20310, and/or support surface 20317. This reduction in frictional force can reduce the force required to perform the staple firing stroke in the proximal zone 20301. Such an arrangement can help ease the load on a motor of the staple firing system at the beginning of a firing stroke where an initially high firing force may be undesirable.

In the intermediate zone 20302, the inner cartridge wall 20315 comprises a second vertical wall height tW2 and a second vertical gap height tG2. The second vertical wall height tW2 is defined as the distance between the deck surface 20311 and a bottom 20316 of the inner cartridge wall 20315. The second vertical gap height tG2 is defined as the distance between the bottom 20316 of the inner cartridge wall 20315 and the support surface 20317. The second vertical wall height tW2 is greater than the first vertical wall height tW1. Thus, the second vertical gap height tG2 is less than the first vertical gap height tG1.

As can be seen in FIG. 10, the inner web 20352 travels within the second vertical gap height tG2 such that there is a second clearance gap tCG2 between the top of the inner web 20352 and the bottom 20316 of the inner cartridge wall 20315. The second clearance height tCG2 provides a small gap between the inner web 20352 and the bottom 20316 of the inner cartridge wall 20315 as the sled passes through the intermediate zone 20302. During the staple firing stroke, however, the cartridge body 20310 may deflect downwardly such that the second clearance gap tCG2 is eliminated and the inner cartridge wall 20315 is in contact with the sled 20350. The inner web 20352 of the sled 20350 can be in contact with the inner cartridge wall 20315 as the sled 20350 is advanced distally. The second clearance height tCG2 may not be present prior to the firing stroke and during the firing stroke. In any event, as the inner web 20352 passes underneath the cartridge body 20310 in the intermediate zone 20302, the inner web 20352 can provide support to the inner cartridge wall 20315 and, thus, the cartridge body 20310.

Although the contact between the inner web 20352 of the sled 20350 and the inner cartridge wall 20315 increases the force needed to push the sled 20350 through the firing stroke, the reduction of cartridge body deflection is prioritized over required firing forces in the intermediate zone 20302, for example. The second clearance gap tCG2 can be less than the first clearance gap tCG1 but not zero. The second clearance gap tCG2 may be zero or at least substantially zero relative to possible manufacturing tolerances. The second vertical gap height tG2 (the space through which the inner web 20352 travels) can be less than the vertical height of the inner web 20352. In such an instance, the inner web 20352 would positively deflect the inner cartridge wall 20315 vertically away from the opposing support surface 20317.

In the distal zone 20303, the inner cartridge wall 20315 comprises a third vertical wall height tW3 providing a third vertical gap height tG3. The third vertical wall height tW3 is defined as the distance between the deck surface 20311 and a bottom 20316 of the inner cartridge wall 20315. The third vertical gap height tG3 is defined as the distance between the bottom 20316 of the inner cartridge wall 20315 and the support surface 20317. The second vertical wall height tW2 is greater than the first vertical wall height tW1 and the third vertical wall height tW1. Thus, the second vertical gap height tG2 is less than the first vertical gap height tG1 and the third vertical gap height tG3. The inner web 20352 moves within the third vertical gap height tG2 such that there is a third clearance gap similar to, or the same as, the first clearance gap tCG1 between the top of the inner web 20352 and the bottom 20316 of the inner cartridge wall 20315. The cartridge body 20310 may be less susceptible to deflection, and thus may need less support, near its distal end given that the two sides of the cartridge body are connected at the nose, or distal end, of the cartridge body.

Further to the above, each zone 20301, 20302, 20303 may have a different vertical wall height and a different vertical gap height than the other. The magnitude of the vertical wall height may gradually increase from a proximal end of the staple cartridge assembly 20300 to a distal end of the staple cartridge assembly 20300. Alternatively, the magnitude of the vertical wall height may gradually decrease from a proximal end of the staple cartridge assembly 20300 to a distal end of the staple cartridge assembly 20300. Further, the magnitude of the vertical gap height may gradually increase from a proximal end of the staple cartridge assembly 20300 to a distal end of the staple cartridge assembly 20300. Alternatively, the magnitude of the vertical gap height may gradually decrease from a proximal end of the staple cartridge assembly 20300 to a distal end of the staple cartridge assembly 20300. In any event, the magnitude of the vertical wall height and/or the vertical gap height can be specifically tuned for specific zones of the cartridge body 20310 to provide a desired balance between the deflection support that the sled 20350 can provide during the firing stroke and the firing force needed to complete the firing stroke.

As described above, the sled 20350 can interact, or at least potentially interact, with an inner cartridge wall 20315 of the cartridge body 20310. As also described above, the cartridge body 20310 comprises two inner cartridge walls 20315—one on each side of the longitudinal slot 20312 defined in the cartridge body 20310. As depicted in FIGS. 6-10, the sled 20350 can be configured to engage both of the inner cartridge walls 20315 as described above. The sled 20350 comprises two inner support webs 20352 which can each support an inner cartridge wall 20315 and support the cartridge body 20310 equally, or at least substantially equally, on both sides of the cartridge body 20310. Moreover, as discussed above, the cartridge body 20310 comprises longitudinal cartridge walls in addition to the inner cartridge walls 20315. The sled 20350 can comprise one or more additional support webs that can engage and support the longitudinal cartridge walls of the cartridge body 20310.

As discussed above, the inner cartridge walls 20315 can deflect when a compressive load, for example, is applied to the deck of the cartridge body 20310. As can be seen in FIGS. 7 and 8, the sled 20350 further comprises horizontal ledges 20357 extending laterally, or outwardly, from the distal end 20356 of the central nose portion 20355 that can engage and support the inner cartridge walls 20315 and inhibit the cartridge body 20310 from deflecting, or at least deflecting further. The horizontal ledges 20357 are configured to support the inner cartridge walls 20315 in at least two ways. More specifically, the horizontal ledges 20357 extend laterally under the inner cartridge walls 20315 and can support the cartridge body 20310 from deflecting downwardly and, also, extend between the inner cartridge walls 20315 and can support the inner cartridge walls 20315 from deflecting inwardly. The horizontal ledges 20357 comprise distal lead-in surfaces configured to pry the inner cartridge walls 20315 open and/or lift the inner cartridge walls 20315 upwardly. The distal lead-in surfaces can help reduce binding, or jamming, between the sled 20350 and the cartridge body 20310, especially in instances of higher clamping loads between the end effector jaws. The horizontal ledges 20357 are configured to support the inner cartridge walls 20315 at a location that is distal to, or ahead of, the ramped wedges 20361, 20362 engaging the staple drivers during the firing stroke. As a result, the horizontal ledges 20357 can help support the inner cartridge walls 20315 and reduce cartridge body 20310 deflection distally, or ahead, of a firing driver, such as an I-beam and/or tissue cutting knife, for example, moving between the inner cartridge walls 20315 during the firing stroke.

Further to the above, an I-beam may be movable from a proximal unfired position to a distal fired position during a firing stroke to push the sled 20350 distally. The I-beam comprises a first cam that engages a first jaw of the end effector and a second cam that engages a second jaw of the end effector. The first cam and the second cam may each comprise a flange extending laterally from a central portion of the I-beam, for example. As the I-beam is moved distally during the firing stroke, the I-beam can pull the first jaw and the second jaw toward one another to compress the patient tissue positioned therebetween. The location of the I-beam can represent the location at which the staple cartridge may be most prone to collapsing.

FIGS. 11-13 depict a surgical stapling assembly 20400 configured to help reduce cartridge deflection during a firing stroke. The surgical stapling assembly 20400 comprises an anvil jaw, a channel jaw 20470, a staple cartridge 20409 positioned within the channel jaw 20470, and a cartridge support pillar 20440 slideably positioned within the staple cartridge 20409. The staple cartridge 20409 comprises a proximal end 20401 and a distal end 20402. The staple cartridge 20409 comprises a cartridge body 20410 comprising two sides 20412 defined by a longitudinal slot 20411 extending therebetween that is configured to receive at least a portion of a firing driver, such as a sled, cutting edge, I-beam, and/or firing shaft, for example, during a firing stroke. Each side 20412 comprises a plurality of staple cavities 20413 defined in a deck surface 20414 of the cartridge body 20410 that are each configured to removably store a staple therein. As can be seen in FIG. 12, the cartridge support pillar 20440 comprises an upper portion 20441, an intermediate portion 20442, and a lower portion 20444. The cartridge support pillar 20440 is closely received within the longitudinal slot 20411 and is configured to slide within the longitudinal slot 20411 during firing stroke. The cartridge support pillar 20440 is configured to counter, prevent, and/or resist cartridge deflection in the cartridge body 20410 when the cartridge body 20410 is subjected to a compressive, or clamping, load. As discussed in greater detail below, the cartridge support pillar 20440 is configured to transfer or transmit loads that would otherwise cause the deflection of the cartridge body 20410.

The intermediate portion 20442 of the cartridge support pillar 20440 comprises laterally extending ledges, or wings, 20443 providing a greater width of the intermediate portion 20442 relative to the upper portion 20441 and the lower portion 20444. The wings 20433 are received within corresponding lateral slots 20415 defined in inner cartridge walls 20420 of the longitudinal slot 20411. The wings 20433 are sized and configured such that the wings 20433 are in contact with, or engaged with, the inner cartridge walls 20420 prior to the cartridge body 20410 being subjected to a compressive, or clamping, load. The wings 20433 can be sized and configured such that the wings 20433 are not in contact with the inner cartridge walls 20420 prior to the cartridge body 20410 being subjected to a compressive, or clamping, load; however, the inner cartridge walls 20420 can deflect into contact with the wings 20433 when the cartridge body 20410 is subjected to a compressive load. The engagement between the wings 20443 and the side walls of the lateral slots 20415 can help support the inner cartridge walls 20420 and reduce the vertical and/or lateral deflection thereof, as well as of the cartridge body 20410 overall. The cartridge support pillar 20440 can reduce or prevent collapsing within the staple cartridge 20409 when the jaws of the surgical stapling assembly 20400 are closed and/or during the staple firing stroke. In at least one respect, the cartridge support pillar 20440 provides a buffer structure within the longitudinal slot 20411 to prevent the sides 20412 from buckling the longitudinal slot 20411 inwardly. Moreover, as discussed in greater detail below, the cartridge support pillar 20440 can redirect clamping load into the channel jaw 20470 through the ledges 20443 without the clamping load flowing through the deck 20414.

In use, further to the above, patient tissue can be clamped against the deck 20414 of the cartridge body 20410 when the surgical stapling assembly 20400 is moved into a clamped configuration. Also, in use, patient tissue can be further compressed against the cartridge body 20410 during the staple firing stroke. A compressive load may flow through the cartridge body 20410 into the jaw 20470 and, as described above, the compressive load can distort the cartridge body 20410. Referring to FIG. 13, the cartridge support pillar 20440 transmits a portion of the compressive load directly into the jaw 20470 without the load passing through the cartridge body 20410, or at least without passing through the deck 20414 of the cartridge body 20410. The cartridge support pillar 20440 comprises a bottom surface 20445 configured to be supported by the channel jaw 20470—either directly or through a cartridge pan attached to the cartridge body 20410 which is in contact with the channel jaw 20470. The upper portion 20441 of the cartridge support pillar 20440 can be flush with top surface of the deck 20414 while the upper portion 20441 may extend above the deck 20414 so as to intercept clamping forces so that the clamping forces can be redirected through the cartridge support pillar 20440 into the channel jaw 20470.

Referring now to FIG. 11, the cartridge support pillar 20440 is positioned near an intermediate zone of the staple cartridge 20409, i.e., at a location between the proximal end of the staple cartridge 20409 and a distal end of the staple cartridge 20409. The cartridge support pillar 20440 may be pre-positioned in the position illustrated in FIG. 11 so as to absorb clamping forces at this position ahead of a staple firing stroke. As the jaws of the end effector are clamped together to initially clamp tissue and/or as an I-beam starts to apply final clamping forces during the beginning of a firing stroke, for example, clamping loads are experienced throughout the longitudinal length of the staple cartridge 20409. Pre-positioning the cartridge support pillar 20440 in the intermediate zone, for instance, helps reduce cartridge deflection ahead of the firing stroke at the position of the cartridge support pillar 20440. The cartridge support pillar 20440 may be pre-positioned at the beginning of the staple firing stroke, or closer to the proximal end of the staple cartridge 20409, instead of near the intermediate zone of the staple cartridge 20409. Alternatively, the cartridge support pillar 20440 may be pre-positioned toward the end of the staple firing stroke, or closer to the distal end of the staple cartridge 20409. As described in greater detail below, the cartridge support pillar 20440 may be configured to be moved distally by the firing driver when the firing driver comes into contact with the support pillar 20440.

When the firing driver reaches the cartridge support pillar 20440, referring to FIG. 11, the firing driver pushes the cartridge support pillar 20440 toward the distal end 20402 during the rest of the staple firing stroke. As the cartridge support pillar 20440 is pushed distally by the firing driver, the cartridge support pillar 20440 dynamically helps reduce cartridge deflection as the support pillar 20440 moves distally through the rest of the firing stroke. Stated another way, it should be appreciated that the highest loads, or at least some of the highest loads, experienced in the surgical stapling assembly 20400 are located around the staples being fired, i.e., pushed upwardly toward and against the anvil jaw by the sled which is being pushed distally by, for example, an I-beam, and, when the sled and the support pillar 20440 are both pushed distally by the I-beam during the staple firing stroke, the support pillar 20440 is advantageously present at, or adjacent to, these high loads. As a result, the support pillar 20440 can provide effective support that moves in conjunction with the occurrence of these high loads.

In accordance with the present disclosure, a plurality of cartridge support pillars 20440 can be pre-positioned within the longitudinal slot 20411. A proximal cartridge support pillar, an intermediate cartridge support pillar, and a distal cartridge support pillar can be positioned in the longitudinal slot 20411 and can be evenly spaced throughout a staple firing stroke, for example. The firing driver can travel a first distance before the firing driver bumps into the proximal cartridge support pillar. The firing driver then travels a second distance before the proximal cartridge support pillar, and/or the firing driver, bumps into the intermediate cartridge support pillar. The firing driver then travels a third distance before the intermediate cartridge support pillar bumps into the distal cartridge support pillar. A final distance is traveled where the firing driver pushes all of the support pillars into a final position at the completion of the firing stroke. In accordance with the present disclosure, the first distance, the second distance, the third distance, and the final distance can be the same. Alternatively, the first distance, the second distance, the third distance, and the final distance can be different. Further, a first one of the first distance, the second distance, the third distance, and the final distance can be equal to a second one of the first distance, the second distance, the third distance, and the final distance but different from a third one of the first distance, the second distance, the third distance, and the final distance, for example.

In accordance with the present disclosure, the number and/or size of the cartridge support pillars 20440 pre-positioned within the staple cartridge 20409 can be selected based on the length of the staple cartridge, the thickness of tissue to be cut and stapled, and/or the size of the staples in the staple cartridge. For example, where higher clamping pressures are expected with thicker tissue, additional cartridge support pillars 20440 can be utilized. The staple cartridge 20409 can come with a plurality of cartridge support pillars 20440 and a user can insert the desired number of cartridge support pillars 20440 in the longitudinal slot 20411 and/or remove unwanted cartridge support pillars 20440. The user can also select the desired position of each cartridge support pillar 20440. The longitudinal slot 20411 may comprise pre-defined alignment detents defined in the cartridge body 20410 to align and/or releasably retain the cartridge support pillars 20440 in position.

In accordance with the present disclosure, the cartridge support pillar 20440 can be configured to carry and deliver a hemostatic agent to tissue. The hemostatic agent may comprise oxygenated regenerated cellulose, for example. The cartridge support pillar 20440 can be coated in the hemostatic agent such that the hemostatic agent is distributed onto tissue upon rubbing against the tissue, for example. The cartridge support pillar 20440 may comprise a reservoir to carry the hemostatic agent. The sled and/or I-beam can be configured to puncture the reservoir upon bumping into the cartridge support pillar 20440 during the staple firing stroke. The cartridge support pillar 20440 can be press fit into the longitudinal slot 20411 and/or held with support detents extending inwardly from the walls of the longitudinal slot 20411, for example, so as to provide enough holding force to the cartridge support pillar 20440 to be punctured prior to being pushed distally. The hemostatic agent can be applied to the tissue near the cut line for the remainder of the firing stroke. In accordance with the present disclosure, only a proximal cartridge support pillar of the plurality of support pillars 20440 may comprise a hemostatic agent. More than one cartridge support pillar 20440 may comprise a hemostatic agent configured to be delivered to tissue during a firing stroke.

Further to the above, referring again to FIGS. 11-13, a firing driver, such as an I-beam, for example, can push a sled and one or more support pillars distally during a staple firing stroke. The sled comprises ramps that engage the staple drivers of a staple cartridge to eject the staples stored therein and may comprise a gap or slot can be defined between two of the sled ramps that are configured to receive, or at least partially receive, a support pillar therein. As a result, the I-beam can push the sled and the sled pushes the support pillar during a staple firing stroke. The support pillar may comprise one or more ramps which co-operate with the ramps of the sled to lift the staple drivers and staples of a staple cartridge during the staple firing stroke. FIG. 14 depicts a cartridge support pillar 20480 comprising a primary support pillar body 20481 and a sled portion 20485 extending from the primary support pillar body 20481. In accordance with the present disclosure, the support pillar 20480 can be pre-positioned in a staple cartridge at a location that is proximal to a distal-most row of staple drivers such that, when the primary support pillar body 20481 is engaged and pushed distally by a firing driver, the sled portion 20485 at least partially lifts the distal-most row of staple drivers to ensure that the distal-most staples supported by the distal-most row of staple drivers, for instance, are formed fully during the staple firing stroke. The primary support pillar body 20481 comprises an upper portion 20482, a wider intermediate portion 20483, and a lower portion 20484. The sled portion 20485 extends from the lower portion 20484. The sled portion 20485 comprises ramped wedges 20486 configured to engage staple drivers when the cartridge support pillar 20480 is advanced distally by the firing driver. Such a configuration can ensure that the distal-most staples of each longitudinal staple row are fully formed at the completion of the staple firing stroke.

Further to the above, the firing driver can be retracted proximally after the staple firing stroke. The sled and the support pillars may not be retracted proximally with the firing driver after the staple firing stroke. The support pillars may remain at the distal end of the staple cartridge after the firing stroke has been completed. In accordance with the present disclosure, the distal end, or nose, of the cartridge body may comprise a housing to store or stow one or more cartridge support pillars therein. In circumstances where the firing driver is retracted before the staple firing stroke has been completed, the sled and the support pillars can be left in place at an intermediate location in the staple firing stroke.

As discussed above, a sled of a staple cartridge can be configured to contact a support pillar and push the support pillar during a staple firing stroke. As discussed in greater detail further below, the sled can also be configured to extend under at least a portion of the support pillar and receive a compressive or clamping load from the support pillar. FIGS. 15-18 depict a staple cartridge assembly 20500 for use with a surgical stapling end effector such as, for example, those disclosed herein. The staple cartridge assembly 20500 comprises a cartridge body 20510, a sled 20540 configured to eject staples stored in the cartridge body 20510, and a cartridge support pillar 20570 configured to help reduce cartridge deflection. The cartridge body 20510 comprises a deck surface 20511 configured to support patient tissue thereon, a plurality of staple cavities 20512 defined in the deck surface 20511 that are configured to removably store a plurality of staples therein, and a longitudinal slot 20513 through which at least a central portion 20541 of the sled 20540 is configured to travel and through which at least a portion of a firing driver which pushes the sled 20540 distally is configured to travel. The firing driver is configured to push the sled 20540 from a proximal, unfired position (FIG. 15) to a distal, fired position (FIG. 18) to eject the staples from the staple cartridge assembly 20500. The firing driver may comprise the sled 20540, a firing shaft, a tissue cutting edge, and/or a distal I-beam head, for example. The staple cartridge assembly 20500 does not have a cartridge pan and the cartridge body 20510 is directly supported by the cartridge channel of a surgical stapling instrument when the staple cartridge assembly 20500 is installed in the cartridge channel. The staple cartridge assembly 20500 may comprise a cartridge pan attached to the cartridge body 20510 configured to abut the cartridge channel when the staple cartridge assembly 20500 is installed in the cartridge channel.

The cartridge support pillar 20570 is configured to help reduce deflection of the cartridge body 20510 at and/or around the location of the cartridge support pillar 20570 during the application of clamping loads to the cartridge body 20510. The cartridge support pillar 20570 can be pre-positioned along the firing stroke such as, for example, at the position shown in FIG. 15 such that the cartridge support pillar 20570 can support the cartridge body 20510 ahead of the firing driver and/or sled 20540 during the firing stroke. The cartridge support pillar 20570 comprises an upper pillar portion 20571 and a base portion 20575. The upper pillar portion 20571 comprises a top 20572, a protrusion 20573, and a bottom portion 20574. The base portion 20575 extends from the bottom portion 20574. The base portion 20575 is configured to be supported by a cartridge channel of a stapling instrument when the staple cartridge assembly 20500 is seated in the cartridge channel. The base portion 20575 can sit directly on top of a support surface of the cartridge channel opposite a bottom of the cartridge body 20510. Moreover, the base portion 20575 is positioned and configured to translate within the same space, or cavity, within which a base portion of the sled 20540 is configured to travel during the staple firing stroke.

The sled 20540 comprises a central portion 20541 comprising a notch that defines a shoulder 20542 configured to engage the protrusion 20573 when the sled 20540 contacts the cartridge support pillar 20570 during the staple firing stroke. The shoulder 20542 can extend under the protrusion 20573 such that the support pillar 20570 can sit on the shoulder 20542 of the sled 20540 when the support pillar 20570 is subjected to a compressive load. As a result, both the support pillar 20570 and the sled 20540 can both transmit the compressive load to a support structure positioned thereunder. In accordance with the present disclosure, where the staple cartridge assembly 20500 comprises a pan attached to the cartridge body 20510, the sled 20540 can slide on top of the pan and transmit the compressive load from the support pillar 20570 to the pan. In accordance with the present disclosure, where the staple cartridge does not comprise a pan attached to the cartridge body 20510, the sled 20540 can slide on top of a support surface defined on the cartridge channel and transmit the compressive load from the support pillar 20570 to the cartridge channel. The cartridge body 20510 may comprise one or more support shoulders upon which the sled 20540 slides that are configured to receive the compressive load from the sled 20540.

As can be seen in FIG. 18, further to the above, the cartridge support pillar 20570 is configured to be nested longitudinally within the sled 20540 when the sled 20540 engages the cartridge support pillar 20570. This nested longitudinal arrangement allows the cartridge support pillar 20570 to be positioned entirely proximal with respect to a distal end of the ramped wedges of the sled 20540. A ramped wedge 20543 is illustrated in phantom in FIG. 18 illustrating that the cartridge support pillar 20570 is proximal to a distal end of the ramped wedge 20543 once the sled 20540 and the support pillar 20570 have become fully nested. Such a configuration helps reduce the overall length of a firing assembly and can reduce the need for additional longitudinal space at the distal end, or nose, of the staple cartridge to accommodate the firing assembly at the end of the staple firing stroke while ensuring that all of the staples are fully fired by the sled.

FIGS. 18A-18C depict a surgical stapling system 20580 comprising a staple cartridge 20581 having a proximal end 20852 and a distal end 20853 and a cartridge channel 20585 within which the staple cartridge 20851 is positioned. Similar to other staple cartridges disclosed herein, the staple cartridge 20851 comprises a movable cartridge support 20590. The surgical stapling system 20580 further comprises a sensing system 20595 configured to detect a parameter of the surgical stapling system 20580 at the movable cartridge support 20590. Like the other movable cartridge supports disclosed herein, the movable cartridge support 20590 is pre-positioned within the staple cartridge 20581. The movable cartridge support 20590 is positioned within a longitudinal slot of the staple cartridge 20581 and is configured to be pushed distally by a firing driver, such as an I-beam, tissue cutting knife, and/or firing bar, for example, and/or a sled pushed distally by the firing driver, during a staple firing stroke. The movable cartridge support 20590 may be pre-positioned at a high load location such that the movable cartridge support 20590 is configured to reduce deflection of the staple cartridge 20581 within the high load location.

The movable cartridge support 20590 comprises an upper portion 20591 positioned within the central longitudinal slot of the staple cartridge 20851, a lateral-flange portion 20592, and a lower portion 20593. The lateral-flange portion 20592 is positioned within a longitudinal cavity defined between the bottom of the staple cartridge 20581 and an opposing support surface of the cartridge channel 20585. The lateral-flange portion 20592 is configured to fill this longitudinal cavity at the location of the movable cartridge support 20590 so as to help reduce vertical and lateral cartridge deflection by transferring the clamping load experienced by the staple cartridge 20581 to the cartridge channel 20585. The lateral-flange portion 20592 is sized and configured such that it is engaged with, or in close proximity to, the sidewalls of the longitudinal cavity. At least a portion of the lower portion 20593 is configured to slide within a longitudinal channel slot defined in the cartridge channel 20585. The longitudinal channel slot is aligned, or at least substantially aligned, with the central longitudinal slot defined in the staple cartridge 20851 such that the movable cartridge support 20590 extends through the longitudinal channel slot of the cartridge channel and the central longitudinal slot defined in the staple cartridge 20851.

In accordance with the present disclosure, the movable support 20590 can be utilized as a vehicle for a load-detection system that measures the clamping load at the movable support 20590. The sensing system 20595 comprises a sensor 20597, an electrical lead 20596, and an electrical contact 20598 connected to the sensor 20597 by the electrical lead 20596. The sensor 20597 comprises any suitable sensor such as, for example, a load cell and/or a strain gauge configured to detect a compressive clamping load, for instance, being transmitted through the movable support 20590. The sensing system 20595 further comprises a longitudinally-extending conductive trace 20599 positioned within the cartridge channel 20585. The conductive trace 20599 can be positioned on a sidewall of the longitudinal channel slot defined in the cartridge channel 20582 so that the electrical contact 20598 is electrically coupled with the conductive trace 20599 regardless of where the movable cartridge support 20590 is positioned along the staple firing stroke path. The conductive trace 20599 may comprise a supply trace and a return trace. A supply trace can be positioned on one side of the longitudinal channel slot and a return trace can be positioned on the opposite side of the longitudinal channel slot. Further, one trace can be positioned within the longitudinal channel slot and another trace can be positioned on or within a cartridge deck surface of the cartridge body, for example.

The sensing system 20595 is coupled to a control circuit, for example, configured to monitor the load detected by the sensing system 20595. In accordance with the present disclosure, the control circuit can be configured to control the operation of a surgical stapling instrument—and use data from the sensing system 20595 to control the operation of the surgical stapling instrument, as described in greater detail below. The control system can be configured to control an electric motor, or closure motor, actuatable to clamp the end effector jaws of the surgical stapling instrument and/or an electric motor, or firing motor, actuatable to move a firing driver through a staple firing stroke. The control circuit can be configured to monitor the position of the movable cartridge support 20590 in addition to monitoring the load detected by the sensing system 20595. The control circuit can also monitor a position of the sled and/or firing driver during the firing stroke. Such embodiments can allow a control circuit to determine a tissue pressure at a specific location within the firing stroke.

Further to the above, the control circuit can be configured to utilize the position of the sled, the position of the firing driver, the position of the movable cartridge support 20590, and/or the load detected by the sensing system 20595 to control the staple firing stroke. In accordance with the present disclosure, the control circuit can be configured to operate the firing motor at a predetermined, or preset, speed when the staple firing stroke is actuated. Based on data from the sensing system 20595, however, the control circuit is configured to operate the firing motor at a slower speed and/or at a faster speed than the predetermined speed. For example, after the jaws of the end effector have been clamped onto patient tissue—but prior to performing the staple firing stroke—the detected clamping load may exceed a predetermined threshold load and, in response, the control circuit is configured to automatically adjust the predetermined speed of the firing motor prior to the staple firing stroke. The excessive clamping load may indicate that the tissue captured between the jaws of the end effector is thick and/or dense and, as a result, the control circuit may operate the firing motor at a slower speed. The control circuit can adjust the predetermined speed to a lower predetermined speed when the detected clamping load exceeds the threshold. The control circuit can adjust the predetermined speed of the firing motor as a function of detected clamping load. The amount by which the control circuit adjusts speed of the firing motor can be proportional to the amount in which the detected clamping load exceeds the threshold. The control circuit may comprise a processor and a pulse width modulation circuit and/or a frequency modulation circuit, for example, that can be used to operate the firing motor at a slower speed. In addition to or in lieu of adjusting the speed of the firing motor, the control circuit can be configured to adjust the torque that can be delivered by the firing motor. The control circuit is also configured to adjust the speed and/or torque of the firing motor during the staple firing stroke based on data received from the sensing system 20595 during the staple firing stroke. In addition to or in lieu of limiting the speed of the firing motor when the detected clamping load is excessive, i.e., exceeds a predetermined value, the control circuit is also configured to increase the current to the firing motor or the current available to the firing motor.

Further to the above, the control circuit can be configured to dynamically adjust the speed and/or torque of the firing motor during different portions of the staple firing stroke. A staple firing stroke can have several portions-a first portion in which the movable cartridge support 20590 is stationary while a firing driver is moved toward the cartridge support 20590 by the firing motor, and a second portion in which the cartridge support 20590 is being moved distally by the firing driver. The control circuit can utilize a first set of parameters to operate the firing motor during the first portion of the staple firing stroke and a second set of parameters to operate the firing motor during the second portion of the staple firing stroke. The control circuit can be configured to evaluate the clamping load at the movable cartridge support 20590 prior to the staple firing stroke and/or when the staple firing stroke is initiated to establish the parameters used to operate the firing motor during the first portion of the staple firing stroke and then re-evaluate the clamping load at the movable cartridge support 20590 when the sled and/or firing driver are at and/or near the movable cartridge support 20590. At such point, new parameters are selected for the rest of the staple firing stroke. The new parameters used during the second portion of the staple firing stroke can be the same as the parameters used during the first portion of the staple firing stroke. The control circuit can be configured to automatically adjust motor parameters in anticipation of the additional resistance caused by having to push the movable cartridge support 20590 distally upon reaching the movable cartridge support 20590. These motor parameters can be selected based on not only the presence of the movable cartridge support 20590 but, also, based on the monitored clamping load at the movable cartridge support 20590.

In accordance with the present disclosure, a staple cartridge may comprise a plurality of pre-positioned cartridge supports, or pillars, where one or more of the supports are equipped with a sensing system such as the sensing systems disclosed herein. A control circuit can be configured to monitor a clamping load at each pre-positioned cartridge supports and can be configured to adjust a motor control program based on the monitored loads at a plurality of locations.

In accordance with the present disclosure, moving opposing jaws into a fully clamped position can complete a sensing circuit within the end effector such that the sensing circuit is only powered upon attaining a fully clamped position with the jaws.

In accordance with the present disclosure, the sensor 20597 can be disconnected from the conductive trace 20599 upon being moved out of its initial position by the sled and/or firing driver, for example. The clamping load can be monitored by a control circuit via the conductive trace 20599 and the sensor 20597 while the movable cartridge support 20590 remains in its home position; however, once the cartridge support 20590 is moved distally out of its home position by the firing driver, the sensing circuit including the conductive trace 20599 and sensor 20597 is open and the control circuit is no longer in communication with the sensor 20597. The control circuit is configured to detect the open sensing circuit and take appropriate action. The control circuit can be configured to utilize a different set of motor control parameters upon detecting that the sensor circuit is open. In accordance with the present disclosure, the sensor 20597 can be substituted with a resistor and the sensor circuit is in a closed state while the cartridge support is in its home, or unadvanced, position. When the cartridge support is advanced distally from its home position, the sensing circuit remains closed through the remainder of the staple firing stroke but the resistance of the sensing circuit changes depending on the position of cartridge support. The sensing circuit and cartridge support can act as a potentiometer varying the resistance of the sensing circuit as the firing stroke progresses.

In accordance with the present disclosure, a conductive trace may be mounted to a movable cartridge support, such as the movable cartridge support 20590, for example. The conductive trace can straddle the cartridge support. The conductive trace mounted to the movable cartridge support is configured to close a sensing circuit when the firing driver reaches the end of its staple firing stroke. The sensing circuit is in communication with a control circuit such that the control circuit is configured to determine that the firing driver, the sled, and/or the movable cartridge support 20590 has reached the end-of-stroke position. At such point, the control circuit is configured to stop and/or reverse the firing motor.

In accordance with the present disclosure, an electrical circuit can be utilized to determine the stroke position of a sled within an end effector. FIG. 19 depicts a surgical stapling assembly 20600 comprising a firing assembly 20610, a sled 20620 configured to be pushed through a firing stroke by the firing assembly 20610, and a cartridge channel jaw 20640. The sled 20620 is part of a replaceable staple cartridge seatable in the cartridge channel jaw 20640; however, other embodiments are envisioned in which the surgical stapling assembly 20600 comprises a loading unit that does not have readily replaceable components. The firing assembly 20610 comprises push rods 20611 and an I-beam head 20612 attached to distal ends of the push rods 20611. The push rods 20611 are translatable by any suitable means for moving the I-beam head 20612 longitudinally through the cartridge channel jaw 20640 such as, for example, by a motor. The I-beam head 20612 comprises a first pin 20613 configured to engage an anvil jaw of the surgical stapling assembly 20600 and a second pin 20614 configured to engage the cartridge channel jaw 20640. The pins 20613, 20614 are configured to travel within corresponding slots in the anvil jaw and cartridge channel jaw 20640 during a firing stroke to control the distance between a deck surface of a staple cartridge and a tissue compression surface of the anvil jaw. The I-beam head 20612 further comprises a distal end 20615 that is configured to abut and push the sled 20620 through the staple firing stroke. The sled 20620 is actuatable through the staple firing stroke by the I-beam head 20612 to eject staples from the staple cartridge. The sled 20620 comprises a base portion 20621 and ramped wedges 20622 extending from the base portion 20621. The ramped wedges 20622 are configured to engage staple drivers to eject staples from the staple cartridge during the firing stroke. The sled 20620 further comprises an electrically conductive trace 20630, discussed in greater detail below, that is in communication with a control circuit that can be used to track the position of the sled 20620.

Further to the above, the cartridge channel jaw 20640 comprises a cartridge channel 20650 configured to receive a replaceable staple cartridge in a channel cavity 20651 defined in the cartridge channel 20650. The channel cavity 20651 is defined by a bottom support surface 20653 and laterally-opposing channel walls 20652, one of which has been removed in FIG. 19 for to better illustrate various components positioned in the cartridge channel jaw 20640. The cartridge channel 20650 further comprises a longitudinal slot 20654 defined in the bottom support surface 20653 that is configured to receive at least a portion of the I-beam head 20612 therein during the firing stroke. The cartridge channel 20650 further comprises a longitudinal channel 20655 defined in a base portion 20656 of the cartridge channel 20650 that is configured to receive the second pin 20614 during the firing stroke.

The surgical stapling assembly 20600 further comprises a flex circuit 20660 positioned within the cartridge channel 20650. The flex circuit 20660 is attached to at least one of the channel walls 20652 of the cartridge channel 20650 via one or more adhesives, for example. That said, the flex circuit 20660 can be attached to the cartridge channel 20650 in any suitable manner. The flex circuit 20660 comprises a plurality of branches. For instance, the flex circuit 20660 comprises a proximal circuit branch 20661 positioned within a proximal zone of the firing stroke, an intermediate circuit branch 20664 positioned within an intermediate zone of the firing stroke, and a distal circuit branch 20667 positioned within a distal zone of the firing stroke. The circuit branches 20661, 20664, 20667 comprise flex circuit portions extending down onto the bottom support surface 20653 of the cartridge channel 20650.

The proximal circuit branch 20661 comprises electrical leads 20662 electrically connected to a control circuit of a surgical stapling system. Similarly, the intermediate circuit branch 20664 comprises electrical leads 20665 electrically connected to the control circuit and the distal circuit branch 20667 comprises electrical leads 20668 connected to the control circuit. The proximal circuit branch 20661 comprises electrical contacts 20663 electrically connected to the electrical leads 20662. Similarly, the intermediate circuit branch 20664 comprises electrical contacts 20666 electrically connected to the electrical leads 20665 and the distal circuit branch 20667 comprises electrical contacts 20669 electrically connected to the electrical leads 20668. The electrical contacts 20663, 20666, 20669 each comprise a discrete location for detecting the position of the sled 20620 as the sled 20620 is advanced distally during the staple firing stroke. When the sled 20620 is in its proximal-most unfired position, the trace 20630 on the sled 20620 electrically connects the contacts 20663 such that the proximal circuit branch 20661 is in a closed state indicating to the control circuit that the sled 20620 is in its proximal-most unfired position. When the sled 20620 is part of a replaceable staple cartridge, the closed state of the proximal circuit branch 20661 can also indicate to the control circuit that the replaceable staple cartridge is in an unfired state. Similarly, when the sled 20620 is in its distal-most fired position, the distal circuit branch 20667 is in a closed state indicating that the sled 20620 is in its distal-most fired position and that the staple cartridge has been fully fired. The control circuit can be configured to automatically operate the firing motor in reverse to retract the I-beam head 20612 by way of a motor upon detecting the closed state of the distal circuit branch 20667.

FIGS. 20-24 depict a surgical stapling assembly 20700 comprising a cartridge channel 20740 configured to receive a replaceable staple cartridge including a cartridge body and a sled 20710, and a sled detection system 20705 configured to detect the location of the sled 20710 within the cartridge channel 20740 during a staple firing stroke. The sled 20710 comprises a base portion 20711, ramped wedges 20712 extending from the base portion 20711 that are configured to eject staples from the staple cartridge body during the firing stroke, and a central portion 20715 configured to travel within a longitudinal slot defined in the cartridge body. The central portion 20715 comprises a lower distal rib 20716 comprising a first width, and a lower proximal rib 20717 comprising a second width which is greater than the first width. The cartridge channel 20740 comprises a bottom 20741 and channel sidewalls 20746 extending from the bottom 20741 that receive the replaceable staple cartridge. The bottom 20741 comprises a supporting surface 20742 configured to support the sled 20710 during the firing stroke. The bottom 20741 further comprises a longitudinal slot 20743 and a longitudinal channel 20744 defined therein. The longitudinal slot 20743 is configured to receive at least a portion of the lower distal rib 20716 and lower proximal rib 20717 of the sled 20710. The longitudinal slot 20743 is further configured to receive at least a portion of a firing driver during the firing stroke. The longitudinal channel 20744 can be configured to receive a cam, or pin, of an I-beam head, for example, during the firing stroke.

The sled detection system 20705 is configured to detect the position of the sled 20710 within the cartridge channel 20740 during the firing stroke. The sled detection system 20705 can be electrically coupled to a control circuit of a surgical stapling instrument. The sled detection system 20705 comprises a conductive post 20720 mounted to the sled 20710 that is positioned within the longitudinal slot 20743 and a flex circuit 20750 positioned within the cartridge channel 20740 configured to be engaged by the conductive post 20720 during the firing stroke. In accordance with the present disclosure, the sled 20710 and the conductive post 20720 may not be connected to one another at the outset of the staple firing stroke. As such, the sled 20710 can engage the conductive post 20720 at the outset of the staple firing stroke. The conductive post 20720 comprises a slot 20722 and conductive side walls 20721 and, during the initial distal motion of the sled 20710 during the staple firing stroke, the lower distal rib 20716 is configured to slide into the slot 20722 of the conductive post 20720. At such point, the lower proximal rib 20717 is configured to push the conductive post 20720 distally through the longitudinal slot 20743 during the firing stroke. The sled 20710 and the conductive post 20720 may not be connected to one another before the staple firing stroke.

The flex circuit 20750 is positioned within a circuit channel 20747 defined in the cartridge channel 20740. The circuit channel 20747 comprises a channel or slot sized and dimensioned such that the flex circuit 20750 is recessed with respect to, or flush with respect to, the inner surfaces of the cartridge channel 20740. As such, the flex circuit 20750 is not likely to interfere with installation of the replaceable staple cartridge into the cartridge channel 20740. The flex circuit 20750 comprises a plurality of branches 20752—each of which includes an electrical wire, or lead, 20753 and an electrical contact 20754. The branches 20752 of the flex circuit 20750 are arranged in pairs such that the contact 20754 of one branch 20752 is positioned on one side of the longitudinal slot 20743 and the contact 20754 of the other branch 20752 is positioned on the opposite side of the longitudinal slot 20743. As a result, each pair of branches 20752 comprises opposing electrical contacts 20754 that are contacted by the conductive post 20720 as the conductive post 20720 passes the electrical contacts 20754 during the staple firing stroke. As the conductive post 20720 passes a pair of opposing electrical contacts 20754, the conductive post 20720 closes an electrical circuit of the opposing electrical contacts 20754 and electrical leads 20753. As the conductive post 20720 moves past the pair of closed opposing contacts 20754, the electrical circuit opens. Progressive closing and opening of the electrical circuits of each pair of opposing secondary circuit branches 20752 during the firing stroke can indicate the position of the conductive post 20720. The position of the conductive post 20720 can be indicative of the position of the sled 20710 and/or the firing driver pushing the sled 20710 distally.

Further to the above, the conductive post 20720 can be slideably positioned within the cartridge channel 20740 and does not comprise part of the replaceable staple cartridge. FIG. 21 depicts the sled 20710 positioned in an unfired position prior to the sled 20710 engaging the conductive post 20720 in a first zone 20707. The conductive post 20720 is pre-positioned in the longitudinal slot 20743 in the first zone 20707 where the conductive post 20720 closes the circuit of the opposing branches 20752 in the first zone 20707 prior to the beginning of the staple firing stroke. As can be seen in FIG. 22, the conductive post 20720 is engaged by the sled 20710 after an initial portion of the firing stroke. From this position, the sled 20710 is advanced further distally during the firing stroke where the conductive post 27620 is pushed out of engagement with the opposing electrical contacts 20754 in the first zone 20707 thereby opening the circuit of the branches 20752 in the first zone 20707. The sled 20710 is then pushed further distally through the firing stroke toward the branches 20752 in a second zone 20708 (FIG. 23) where the conductive post 20720 closes the circuit of the opposing branches 20752 in the second zone 20708. The sled 20710 is advanced further distally during the staple firing stroke where the conductive post 27620 is pushed out of engagement with the opposing electrical contacts 20754 in the second zone 20708 thereby opening the circuit of the branches 20752 in the second zone 20708. The sled 20710 is then pushed further distally through the staple firing stroke toward the branches 20752 in a third zone 20709 where the conductive post 20720 closes the circuit of the opposing branches 20752 in the third zone 20709 (FIG. 23) completing the staple firing stroke.

After the staple firing stroke has been completed, further to the above, the sled 20710 is retracted proximally. Referring to FIG. 24, the conductive post 20720 remains in the third zone 20709 as the sled 20710 is retracted back to an unfired position. The conductive post 20720 can release from the lower distal rib 20716 as the sled 20710 is retracted. Additionally, the conductive post 20720 may not be released from the sled 20710 and may be retracted proximally with the sled 20710 into an unfired position. The conductive post 20720 may disconnect from the sled 20710, reseat, or drop off, at the first zone 20707 (into the position shown in FIG. 21) to prepare for another firing stroke of an unfired staple cartridge.

In accordance with the present disclosure, a replaceable staple cartridge may comprise a cartridge circuit including a memory device configured to store at least one datum related to whether or not the staple cartridge had been previously fired. The cartridge circuit is configured to write data onto the memory device which is accessible by the control circuit of a stapling instrument, for example, to determine the spent status of the staple cartridge once the staple cartridge has been installed in the stapling instrument. Where the control circuit receives data from the installed staple cartridge indicating that the staple cartridge has been previously fired, the control circuit can prevent the firing motor from being operated to perform a staple firing stroke. If the control circuit does not receive data from the installed staple cartridge indicating that the staple cartridge has been previously fired, the control circuit permits the firing motor to respond to an input to perform a staple firing stroke.

In accordance with the present disclosure, the conductive post 20720 can provide support within the cartridge channel 20740 so as to help reduce deflection of the cartridge channel 20740 under clamping loads during the firing stroke. The conductive post 20720 can act as a wedge so as to help prevent the longitudinal slot 20743 from collapsing in on itself when subjected to a compressive load when the end effector is clamped onto patient tissue and/or during the staple firing stroke.

FIGS. 25-27 depict a surgical stapling assembly 20800 comprising a firing driver, or member, 20810, a cartridge channel 20820, and a staple cartridge assembly 20830 comprising a deployable support 20840 configured to help reduce deflection of the staple cartridge assembly 20830 during a firing stroke. The firing driver 20810 comprises a firing bar 20811 actuatable by a motor, for example, and a distal I-beam head 20812 attached to the firing bar 20811. The distal I-beam head 20812 comprises a knife edge 20813 configured to cut patient tissue during the firing stroke. The distal I-beam head 20812 is configured to push a sled 20835 of the staple cartridge assembly 20830 during the firing stroke to eject staples from the staple cartridge assembly 20830 and control a tissue gap distance between the staple cartridge assembly 20830 and an anvil. The distal I-beam head 20812 comprises a first cam configured to engage the cartridge channel 20820 and a second cam configured to engage an anvil jaw of the surgical stapling assembly 20800 during the staple firing stroke.

The staple cartridge assembly 20830 comprises a longitudinal slot 20831 defined therein that is configured to receive at least a portion of the distal I-beam head 20812 during the staple firing stroke. The deployable support 20840 can be press-fit into the longitudinal slot 20831 and can be configured to be deployed from the staple cartridge assembly 20830 during the staple firing stroke along a cut-line, for example. The sled 20835 comprises a central portion 20836 configured to be pushed by the distal I-beam head 20812 through the firing stroke. The central portion 20836 comprises a ramp surface 20837 configured to lift the deployable support 20840 out of the longitudinal slot 20831 during the staple firing stroke as the sled 20835 is pushed from a proximal end 20801 of the staple cartridge assembly 20830 to a distal end 20803 of the staple cartridge assembly 20830. The ramp surface 20837 is configured to engage and lift the deployable support 20840 out of, or at least partially out of, the longitudinal slot 20831. The distal I-beam head 20812 may comprise a central ramp surface configured to deploy the deployable support 20840.

The deployable support 20840 fits tightly within the longitudinal slot 20831 such that the deployable support 20840 can reduce the deflection of the staple cartridge assembly 20830 under clamping loads by filling the longitudinal slot 20831. The deployable support 20840 comprises multiple strips 20841 of material; however, the deployable support 20840 can comprise any suitable configuration. The deployable support 20840 may comprise a single strip of material configured to be cut and deployed from the longitudinal slot 20831 during the staple firing stroke. The deployable support 20840 may comprise a rigidity sufficient to prevent, or at least inhibit, the staple cartridge from collapsing, as discussed herein. The deployable support 20840 may comprise a hemostatic agent. The deployable support 20840 may comprise one or more layers of an absorbable hemostat such as, for example, SURGICEL®. The deployable support 20840 may be comprised of oxidized regenerated cellulose, for example.

In accordance with the present disclosure, as described above, a sled of a staple cartridge assembly may comprise a central portion that moves within a central longitudinal slot of the staple cartridge assembly during a staple firing stroke that is configured to receive a tissue cutting knife, or a firing driver having a tissue cutting edge, during the staple firing stroke. FIG. 28 depicts a sled 20900 including a central portion configured to engage the sidewalls of the central longitudinal slot to prevent, or at least inhibit, a staple cartridge assembly from deflecting. The sled 20900 comprises a base portion 20910, ramped wedges 20920 extending from the base portion 20910 configured to eject staples from the staple cartridge assembly, and a central portion 20930 configured to be received within the central longitudinal slot. The sled 20900 comprises a proximal end 20901 and a distal end 20902. The central portion 20930 comprises a proximal portion 20931 and a distal portion 20935—each of which are configured to move through the central longitudinal slot. The proximal portion 20931 comprises a first width W1 and the distal portion 20935 comprises a second width W2 which is greater than the first width W1. The distal portion 20935 comprises a lead-in nose with wedge surfaces 20936 configured to help pry open a longitudinal slot of a staple cartridge assembly in the event that the staple cartridge assembly is collapsed, or deflected inwardly, for example, ahead of the sled 20900 as the sled 20900 moves distally. With the second width W2, the distal portion 20935 can provide support to the staple cartridge assembly by consuming the entire width of the central longitudinal slot during the staple firing stroke. The second width W2 may be greater than the width of the central longitudinal slot. The distal portion 20935 can be configured to spread the central longitudinal slot during the firing stroke as the distal portion 20935 is advanced through the staple cartridge assembly. Alternatively, the second width W2 may be substantially equal to width of the central longitudinal slot so as to provide sufficient support within the central longitudinal slot but not unnecessarily increase friction between the sled 20900 and the central longitudinal slot during the firing stroke.

Further to the above, the distal portion 20935 of the sled 20930 is configured to support the staple cartridge assembly ahead of, i.e., distally with respect to, the staples being deployed during the staple firing stroke. The distal portion 20935 extends distally with respect to a front edge 20903 of the base portion 20910 and distally with respect to ramped wedges 20920 such that the distal portion 20935 can engage the sidewalls of the central longitudinal slot ahead of the staples being deployed. The proximal portion 20931 may further comprise a proximal-most section having a width equal to W2. Such a configuration of the central portion 20930 can create a long length of lateral support within the central longitudinal slot while having a narrow portion positioned intermediate the proximal and distal wide portions of the central portion 20930. The intermediate narrow portion of the central portion 20930 is sufficiently narrow such that it is not in contact with the sidewalls of the central longitudinal slot during the staple firing stroke. Such an arrangement can minimize, or at least reduce, the frictional forces between the central portion 20930 and the sidewalls of the longitudinal slot.

Further to the above, each of the ramped wedges 20920 may further comprise a distal end having a lateral wedge configuration similar to the central portion 20930. Having distally-presenting lateral wedges at the distal end of each ramped wedge 20920 can reduce, or even reverse, the lateral deflection of a cartridge body. The longitudinal cavities defined in the cartridge body through which the ramped wedges 20920 travel during the staple firing stroke may permit lateral deflection within the cartridge body that can cause the walls of the cartridge body to laterally collapse toward each other. The distally-presented lateral wedges of each ramped wedge 20920 can pry open collapsed and/or partially collapsed adjacent cartridge walls. Moreover, a collection of distally-presented lateral wedges of a sled nose, sled ramps, and/or a distal I-beam head, for example, can collectively aid in reducing, or even reversing, lateral cartridge deflection.

In accordance with the present disclosure, the sled 20900 shown in FIG. 28 can be used with a staple cartridge 20940 shown in FIG. 28A comprising a cartridge body 20941. The cartridge body 20941 comprises a deck 20942, a plurality of staple cavities 20943 defined in the deck, and a longitudinal slot 20946 defined in the cartridge body 20941. The longitudinal slot 20946 is configured to receive at least a portion of a firing driver and the central portion 20930 of the sled 20900. The sled 20900 is actuatable distally through the staple cartridge 20940 from a proximal end 20944 to a distal end 20945. The longitudinal slot 20946 comprises a proximal high-load zone 20947 having a first lateral slot width SW1 between opposing slot walls and a distal low-load zone 20948 having a second lateral slot width SW2 between opposing slot walls.

The central portion 20930 is configured to translate through the longitudinal slot 20946 during a firing stroke. In accordance with the present disclosure, the slot widths SW1, SW2 can be sized so as to provide maximum lateral support within the proximal high-load zone 20447 and reduce frictional forces, or force-to-fire, within the distal low-load zone 20448. In other words, the slot width SW1 is equal to or less than the width W2 of the central portion 20930 such that the distal portion 20935 supports and/or pries open the longitudinal slot 20946 within the proximal high-load zone 20447 providing lateral support to the cartridge body 20941 and reducing deflection of the cartridge body 20941. The slot width SW2 is equal to or greater than the width W2 so as to reduce friction between the central portion 20930 and the longitudinal slot 20946 and, thus, the force required to push the sled 20900 through the longitudinal slot 20946.

Further to the above, the wider slot width SW2 of the longitudinal slot 20496 is positioned distally with respect to the narrower slot width SW1. As a result of this arrangement, the force-to-fire the staple cartridge 20940 drops at the end of the staple firing stroke. However, the longitudinal slot 20496 can have any suitable arrangement of wider slot widths SW2 and narrower slot widths SW1.

FIGS. 29-32 depict a surgical stapling assembly 21000 including features configured to reduce the deflection, or collapsing, of a staple cartridge under load. The surgical stapling assembly 21000 comprises an anvil jaw 21010, a cartridge channel jaw 21020, and a replaceable staple cartridge 21040 positionable in the cartridge channel jaw 21020. During a surgical procedure, tissue "T" can be clamped between the anvil jaw 21010 and the staple cartridge 21040. The anvil jaw 21010 comprises an anvil 21011 comprising a tissue-compression surface 21012, a plurality of staple forming pockets 21013 defined in the tissue-compression surface 21012, and a longitudinal slot 21014 configured to receive at least a portion of a firing driver therethrough during a staple firing stroke. An anvil-camming pin of a firing driver can be configured to be received within the longitudinal slot 21014 and is configured to positively position the anvil jaw 21010 relative to the cartridge channel jaw 21020 during the staple firing stroke.

The cartridge channel jaw 21020 comprises a cartridge channel 21030 configured to receive the staple cartridge 21040 therein. The cartridge channel 21030 comprises a bottom portion 21031 and channel sidewalls 21035 extending from the bottom portion 21031 to define a channel cavity 21036 within which the staple cartridge 21040 can be installed. The bottom portion 21031 comprises a longitudinal slot 21032 configured to receive at least a portion of the firing driver therethrough during the firing stroke. A channel-camming pin of the firing driver can be configured to be received within the longitudinal slot 21032 and is configured to positively position the cartridge channel jaw 21020 relative to the anvil jaw 21010 during the staple firing stroke. The bottom portion 21031 further comprises a bottom support surface 21033 opposite the cartridge body 21041, discussed in greater detail below.

The staple cartridge assembly 21040 comprises a cartridge body 21041, a sled 21070 movable through the cartridge body 21041 during the staple firing stroke by the firing driver, a plurality of staple drivers 21090 configured to be lifted by the sled 21070 during the firing stroke, and a plurality of staples 21095 supported by the staple drivers 21090. The cartridge body 21041 comprises a tissue-contacting deck surface 21046 having a plurality of staple cavities 21047 defined therein and a longitudinal slot 21048 configured to receive at least a portion of the firing driver during the firing stroke. The sled 21070 comprises a bottom web portion 21071 and a plurality of ramped wedges 21076 extending upwardly from the bottom web portion 21071 configured to sequentially lift the staple drivers 21090 from an unfired position (FIG. 31) to a fired position (FIG. 32) during the firing stroke to eject the staples 21095 from the cartridge body 21041 toward the anvil jaw 21010. The sled 21070 further comprises a central rib 21079 extending from a central web portion 21072 of the bottom web portion 21071 received within the longitudinal slot 21048. The firing driver can be configured to push the central rib 21079 to advance the sled 21070 distally during the staple firing stroke.

The sled 21070 is configured to be pushed distally from a proximal unfired position by the firing driver to eject the staples 21095. In order for the bottom web portion 21071 of the sled 21070 to translate through the cartridge channel jaw 21020 during the firing stroke, the cartridge channel jaw 21020 comprises a cavity, or space, 21021 defined between the cartridge body 21041 and the bottom support surface 21033 of the bottom portion 21031 of the cartridge channel 21030. The bottom web portion 21071 is configured to translate through the cavity 21021 during the firing stroke. Discussed in greater detail below, the staple cartridge assembly 21040 further comprises support features 21050 positioned within the cavity 21021 which are configured to support the cartridge body 21041 before the staple firing stroke. Discussed in greater detail below, the support features 21050 are configured to be pushed out of the way by the sled 21070 as the sled 21070 passes the support features 21050.

The cartridge body 21041 further comprises a plurality of cartridge walls 21042 extending vertically from the deck surface 21046. The plurality of cartridge walls 21042 define various cavities and spaces within the cartridge body 21041 itself such as, for example, the staple cavities 21047—the vertical spaces within which the staple drivers 21090 are lifted—and the longitudinal spaces within which the ramped wedges 21076 travel. The plurality of cartridge walls 21042 comprise outer walls 21043, intermediate walls 21044, and inner walls 21045. The outer walls 21043 are positioned adjacent to and supported by channel sidewalls 21035, the inner walls 21045 are positioned adjacent to and define the longitudinal slot 21048, and the intermediate walls 21044 are positioned between the outer walls 21043 and the inner walls 21045. As discussed above, the staple cartridge assembly 21040 comprises support features 21050. Specifically, the support features 21050 are positioned on a bottom surface 21049 of the inner walls 21045. The support features 21050 are configured to traverse the cavity 21021, or extend down toward the bottom support surface 21033 of the cartridge channel 21030, to provide vertical support to the inner walls 21045. The support features 21050 can help reduce inward and/or downward deflection of the inner walls 21045 of the cartridge body 21041 by extending down to the bottom support surface 21033. The bottom support surface 21033 can, as a result, counter vertical deflection of the inner walls 21045 by way of the support features 21050.

The support features 21050 comprise proximal support nubs 21051 and support pillars 21052 positioned adjacent and distal to the proximal support nubs 21051. In a fully-extended configuration, or non-hinged configuration, a bottom surface 21053 of the support pillar 21052 is vertically supported by the opposing bottom support surface 21033 of the cartridge channel 21030. Prior to the staple firing stroke, the support pillars 21052 are in the non-hinged configuration so as to provide support to the inner walls 20145. When the sled 21070 is moved through its staple firing stroke, the sled 21070 then hinges the support pillars 21052 out of the way upwardly into pillar cavities 21054. Referring to FIG. 30, the central web portion 21072 of the bottom web portion 21071 of the sled 21070 comprises a distal edge 21074 having a chamfered surface 21075. During the firing stroke, the distal edge 21074 is configured to engage and pivot, or hinge, the support pillars 21052 upwardly toward the pillar cavities 21054. The chamfered surface 21075 is configured to further encourage the rotation of the support pillars 21052 toward the pillar cavities 21054. Once the support pillars 21052 are fully collapsed into the pillar cavities 21054, the support pillars 21052 are held in the pillar cavities 21054 by a top surface 21073 of the central web portion 21072 as the sled 21070 passes thereby. Once the sled 21070 passes the support pillars 21052, the support pillars 21052 are configured to elastically reassume their fully-extended configuration to support the inner walls 21045 proximal of the firing stroke. The support pillars 21052 may not reassume their fully-extended configuration and, instead, may be plastically deformed after being engaged by the sled 21070. In any event, the support pillars 21052 can provide temporary or transient support to the cartridge body 21041.

As discussed above, the support features 21050 extend from the inner walls 21045 of the cartridge body 21041. In addition to or in lieu of the above, various embodiments are envisioned in which the support features 21050 are present on the intermediate walls 21044 and/or the outer walls 21043 of the cartridge body 21041. The support pillars 21052 may each have the same configuration; however, at least some of the support pillars 21052 may have different configurations. The support pillars 21052 may be more robust, such as being thicker, for example, at the proximal end of the cartridge body 21041 as compared to the distal end of the cartridge body 21041. The support pillars 21052 may be taller at the distal end of the cartridge body 21041 as compared to the proximal end of the cartridge body 21041. The top surface 21073 of the central web portion 21072 of the sled 21070 may comprise longitudinal slots defined therein within which the support pillars 21052 can slide as the sled 21070 passes thereby. Such an arrangement can reduce binding between the support pillars 21052 and the sled 21070. The sled 21070 can be configured to engage and break the support pillars 21052 as the sled 21070 passes each support pillar 21052. Some of the support pillars 21052 of the cartridge body 21041 may be frangible and can be configured to break when engaged by the sled while other support pillars 21052 may not be frangible and can be configured to elastically bend out of the way until the sled 21070 passes by the elastically deflected support pillars 21052.

Various aspects of the subject matter described herein are set out in the following examples.

Example 1—A surgical stapling assembly (20100) comprising a first jaw (20130), a second jaw (20120), and a staple cartridge assembly (20140, 20200, 20300, 20400, 20500, 20940, 21000) positioned in the first jaw. The staple cartridge assembly comprises a plurality of staples (20102), a plurality of staple drivers (20250), and a cartridge body (20141, 20210, 20310, 20410, 20510, 20941, 21041). The cartridge body comprises a deck surface (20143, 20212, 20311, 20414, 20511, 20941, 21046) configured to support patient tissue, a longitudinal slot (20144, 20211, 20312, 20411, 20513, 20946, 21048) defined in the cartridge body and configured to receive at least a portion of a knife (20813) therethrough during a firing stroke, a plurality of staple cavities (20145, 20221, 20413, 20943, 21047) defined in the deck surface, wherein the plurality of staples are removably stored within the plurality of staple cavities, and a longitudinal wall (20213, 20315) extending vertically below the deck surface and longitudinally adjacent the longitudinal slot, wherein the longitudinal wall comprises a first zone (20301) comprising a first wall height within the firing stroke and a second zone (20302) comprising a second wall height within the firing stroke greater than the first wall height. The staple cartridge assembly further comprises a sled (20350, 20835, 20900, 21070) movable longitudinally through the cartridge body, wherein the sled comprises a support base (20351, 20910, 21071) and a ramped wedge (20361, 20362, 20712, 20920, 21076) extending upward from the support base, wherein the ramped wedge is configured to lift the plurality of staple drivers to eject the plurality of staples from the plurality of staple cavities during the firing stroke, and wherein the sled is sized and configured resist deflection of the cartridge body during the firing stroke within the second zone.

Example 2—The surgical stapling assembly of Example 1, wherein a vertical gap distance is defined between a bottom surface of the longitudinal wall and a top surface (20351) of the support base of the sled, and wherein the vertical gap distance comprises a first vertical gap distance defined within the first zone and second vertical gap distance defined within the second zone, and wherein the first vertical gap distance is less than the second vertical gap distance.

Example 3—The surgical stapling assembly of Examples 1 or 2, wherein the longitudinal slot comprises laterally-opposing inner slot walls (20213) defining the longitudinal slot, wherein the sled comprises a distal wedge (20930) extending distally from the support base configured to engage the laterally-opposing inner slot walls during the firing stroke, wherein the distal wedge is distal to the ramped wedge, and wherein the distal wedge comprises a first portion (20935) comprising a first lateral wedge thickness and a second portion (20936) comprising a second lateral wedge thickness, wherein the second portion is proximal to the first portion, and wherein the first lateral wedge thickness and the second lateral wedge thickness are different.

Example 4—The surgical stapling assembly of Examples 1, 2, or 3, wherein the longitudinal slot comprises a first zone (20947) comprising a first lateral slot thickness and a second zone (20948) comprising a second lateral slot thickness, wherein the first lateral slot thickness is less than second lateral slot thickness.

Example 5—The surgical stapling assembly of Examples 1, 2, 3, or 4, wherein the staple cartridge assembly further comprises a support surface (20132, 20317, 21033) opposite a bottom of the cartridge body, wherein the sled traverses a longitudinally-extending pathway (21021) defined between the bottom of the cartridge body and the support surface, and wherein the staple cartridge assembly further comprises supports (21050) positioned between the support surface and the cartridge body within the longitudinally-extending pathway.

Example 6—The surgical stapling assembly of Example 5, wherein the sled is configured to move the supports from a supporting position to a collapsed position during the firing stroke.

Example 7—The surgical stapling assembly of Example 6, wherein the supports are biased into the supporting position, and wherein the supports are configured to reassume the supporting position from the collapsed position after the sled passes the supports.

Example 8—The surgical stapling assembly of Examples 1, 2, 3, 4, 5, 6, or 7, wherein the staple cartridge assembly further comprises a material (20840) positioned within the longitudinal slot configured to be lifted above the deck surface by the sled during the firing stroke.

Example 9—The surgical stapling assembly of Example 8, wherein the material is configured to laterally support the longitudinal slot during the firing stroke.

Example 10—The surgical stapling assembly of Examples 1, 2, 3, 4, 5, 6, 7, 8, or 9, wherein the anvil comprises apertures (20171) defined in a cartridge-facing surface of a proximal end of the anvil, wherein the cartridge body comprises projections (20180) configured to be received within the apertures upon moving the second jaw into a clamped position, and wherein each aperture defines an inner surface surrounding an entirety of the projection received within the aperture.

Example 11—The surgical stapling assembly of Examples 1, 2, 3, 4, 5, 6, 7, 8, 9, or 10, further comprising a longitudinally-translatable support (20440, 20480, 20570, 20590) positioned within the longitudinal slot and configured to transfer clamping pressure from the second jaw to the first jaw.

Example 12—The surgical stapling assembly of Example 11, wherein the longitudinally-translatable support is pre-positioned within a high-load zone of the firing stroke prior to the firing stroke.

Example 13—The surgical stapling assembly of Examples 11 or 12, wherein the longitudinally-translatable support is configured to be pushed distally by the sled.

Example 14—The surgical stapling assembly of Examples 11, 12, or 13, wherein the longitudinally-translatable support comprises a sensor (20597).

Example 15—The surgical stapling assembly of Examples 11, 12, 13, or 14, further comprising an electrical circuit (20595) within which the sensor is positioned, wherein the electrical circuit is configured to be closed upon moving the second jaw into a clamped position from an open position.

Example 16—A surgical stapling assembly comprising a first jaw, a second jaw; and a staple cartridge assembly positioned in the first jaw, wherein the staple cartridge assembly comprises a plurality of staples, a plurality of staple drivers, and a cartridge body comprising a deck surface configured to support patient tissue, a longitudinal slot defined in the cartridge body and configured to receive at least a portion of a knife therethrough during a firing stroke, a plurality of staple cavities defined in the deck surface, wherein the plurality of staples are removably stored within the plurality of staple cavities, and a longitudinal wall extending vertically below the deck surface and longitudinally adjacent the longitudinal slot, wherein the longitudinal wall comprises a first zone comprising a first wall height within the firing stroke and a second zone comprising a second wall height within the firing stroke greater than the first wall height. The staple cartridge assembly further comprises a sled movable longitudinally through the cartridge body, wherein the sled comprises a support base, and a ramped wedge extending upward from the support base, wherein the ramped wedge is configured to lift the plurality of staple drivers to eject the plurality of staples from the plurality of staple cavities during the firing stroke, and wherein the sled is sized and configured resist deflection of the cartridge body during the firing stroke within the second zone.

Example 17—The surgical stapling assembly of Example 16, wherein a vertical gap distance is defined between a bottom surface of the longitudinal wall and a top surface of the support base of the sled, and wherein the vertical gap distance comprises a first vertical gap distance defined within the first zone and second vertical gap distance defined within the second zone, and wherein the first vertical gap distance is less than the second vertical gap distance.

Example 18—The surgical stapling assembly of Examples 16 or 17, wherein the longitudinal slot comprises laterally-opposing inner slot walls defining the longitudinal slot, wherein the sled comprises a distal wedge extending distally from the support base configured to engage the laterally-opposing inner slot walls during the firing stroke, wherein the distal wedge is distal to the ramped wedge, and wherein the distal wedge comprises a first portion comprising a first lateral wedge thickness and a second portion comprising a second lateral wedge thickness, wherein the second portion is proximal to the first portion, and wherein the first lateral wedge thickness and the second lateral wedge thickness are different.

Example 19—The surgical stapling assembly of Examples 16, 17, or 18, wherein the longitudinal slot comprises a first zone comprising a first lateral slot thickness and a second zone comprising a second lateral slot thickness, wherein the first lateral slot thickness is less than second lateral slot thickness.

Example 20—The surgical stapling assembly of Examples 16, 17, 18, or 19, wherein the staple cartridge assembly further comprises a support surface opposite a bottom of the cartridge body, wherein the sled traverses a longitudinally-extending pathway defined between the bottom of the cartridge body and the support surface, and wherein the staple cartridge assembly further comprises supports positioned between the support surface and the cartridge body within the longitudinally-extending pathway.

Example 21—The surgical stapling assembly of Examples 16, 17, 18, 19, or 20, wherein the sled is configured to move the supports from a supporting position to a collapsed position during the firing stroke.

Example 22—The surgical stapling assembly of Examples 16, 17, 18, 19, 20, or 21, wherein the supports are biased into the supporting position, and wherein the supports are configured to reassume the supporting position from the collapsed position after the sled passes the supports.

Example 23—The surgical stapling assembly of Examples 16, 17, 18, 19, 20, 21, or 22, wherein the staple cartridge assembly further comprises a material positioned within the longitudinal slot configured to be lifted above the deck surface by the sled during the firing stroke.

Example 24—The surgical stapling assembly of Examples 16, 17, 18, 19, 20, 21, 22, or 23, wherein the material is configured to laterally support the longitudinal slot during the firing stroke.

Example 25—The surgical stapling assembly of Examples 16, 17, 18, 19, 20, 21, 22, 23, or 24, wherein the anvil comprises apertures defined in a cartridge-facing surface of a proximal end of the anvil, wherein the cartridge body comprises projections configured to be received within the apertures upon moving the second jaw into a clamped position, and wherein each aperture defines an inner surface surrounding an entirety of the projection received within the aperture.

Example 26—A surgical stapling assembly comprising a first jaw, a second jaw, and a staple cartridge assembly positioned in the first jaw, wherein the staple cartridge assembly comprises a plurality of staples and a cartridge body comprising a deck surface configured to support patient tissue, a longitudinal slot defined in the cartridge body and configured to receive at least a portion of a knife therethrough during a firing stroke, and a plurality of staple cavities defined in the deck surface, wherein the plurality of staples are removably stored within the plurality of staple cavities. The staple cartridge assembly further comprises a sled movable longitudinally through the cartridge body to eject the plurality of staples from the plurality of staple cavities during the firing stroke and a longitudinally-translatable support positioned within the longitudinal slot and configured to transfer clamping pressure from the second jaw to the first jaw.

Example 27—The surgical stapling assembly of Example 26, wherein the longitudinally-translatable support is pre-positioned within a high-load zone of the firing stroke prior to the firing stroke.

Example 28—The surgical stapling assembly of Examples 26 or 27, wherein the longitudinally-translatable support is configured to be pushed distally by the sled.

Example 29—The surgical stapling assembly of Examples 26, 27, or 28, wherein the longitudinally-translatable support comprises a sensor.

Example 30—The surgical stapling assembly of Examples 26, 27, 28, or 29, further comprising an electrical circuit within which the sensor is positioned, wherein the electrical circuit is configured to be closed upon moving the second jaw into a clamped position from an open position.

Example 31—A surgical staple cartridge comprising a plurality of staples and a cartridge body comprising a deck surface configured to support patient tissue, a longitudinal slot defined in the cartridge body and configured to receive at least a portion of a knife therethrough during a firing stroke, a plurality of staple cavities defined in the deck surface, wherein the plurality of staples are removably stored within the plurality of staple cavities, and a longitudinal wall extending vertically below the deck surface and longitudinally adjacent the longitudinal slot, wherein the longitudinal wall comprises a first longitudinal zone comprising a first wall height within the firing stroke and a second longitudinal zone comprising a second wall height greater than the first wall height. The surgical staple cartridge further comprises a sled movable longitudinally through the first longitudinal zone and the second longitudinal zone, wherein the sled comprises a bottom and a wedge extending upward from the bottom, wherein the wedge is configured to eject the plurality of staples from the plurality of staple cavities during the firing stroke, and wherein the sled is sized and configured resist deflection of the cartridge body during the firing stroke within the second longitudinal zone.

Example 32—The surgical staple cartridge of Example 31, wherein a vertical gap distance is defined between a bottom surface of the longitudinal wall and a top surface of the bottom of the sled, and wherein the vertical gap distance comprises a first vertical gap distance defined within the first longitudinal zone and second vertical gap distance defined within the second longitudinal zone, and wherein the first vertical gap distance is less than the second vertical gap distance.

Example 33—The surgical staple cartridge of Examples 31 or 32, wherein the longitudinal slot comprises laterally-opposing inner slot walls defining the longitudinal slot, wherein the sled comprises a distal wedge extending distally from the bottom configured to engage the laterally-opposing inner slot walls during the firing stroke, wherein the distal wedge is distal to the ramped wedge, and wherein the distal wedge comprises a first portion comprising a first lateral wedge thickness and a second portion comprising a second lateral wedge thickness, wherein the second portion is proximal to the first portion, and wherein the first lateral wedge thickness and the second lateral wedge thickness are different.

Example 34—The surgical staple cartridge of Examples 31, 32, or 33, wherein the longitudinal slot comprises a first slot zone comprising a first lateral slot thickness and a second slot zone comprising a second lateral slot thickness, wherein the first lateral slot thickness is less than second lateral slot thickness.

Example 35—The surgical staple cartridge of Examples 31, 32, 33, or 34, wherein the sled traverses a longitudinally-extending pathway defined beneath a plurality of cartridge walls of the cartridge body, and wherein the staple cartridge assembly further comprises supports extending downwardly from the cartridge walls and positioned within the longitudinally-extending pathway.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of U.S. Pat. No. 11,589,865, entitled METHODS FOR CONTROLLING A POWERED SURGICAL STAPLER THAT HAS SEPARATE ROTARY CLOSURE AND FIRING SYSTEMS, which issued on Feb. 28, 2023, U.S. Pat. No. 6,978,921, entitled SURGICAL STAPLING INSTRUMENT INCORPORATING AN E-BEAM FIRING MECHANISM, which issued on Dec. 27, 2005, U.S. Pat. No. 10,213,203, entitled STAPLE CARTRIDGE ASSEMBLY WITHOUT A BOTTOM COVER, which issued on Feb. 26, 2019, U.S. Pat. No. 10,945,727, entitled STAPLE CARTRIDGE WITH DEFORMABLE DRIVER RETENTION FEATURES, which issued on Mar. 16, 2021, U.S. Pat. No. 11,234,698, entitled STAPLING SYSTEM COMPRISING A CLAMP LOCKOUT AND A FIRING LOCKOUT, which issued on Feb. 1, 2022, U.S. Pat. No. 11,540,826, entitled SURGICAL STAPLER END EFFECTOR SLED HAVING CARTRIDGE WALL SUPPORT FEATURE, which issued on Jan. 3, 2023, U.S. Pat. No. 10,299,792, entitled FASTENER CARTRIDGE COMPRISING NON-UNIFORM FASTENERS, which issued on May 28, 2019, U.S. Pat. No. 8,540,133, entitled STAPLE CARTRIDGE, which issued on Sep. 24, 2013, U.S. Pat. No. 9,788,835, entitled DEVICES AND METHODS FOR FACILITATING EJECTION OF SURGICAL FASTENERS FROM CARTRIDGES, which issued on Oct. 17, 2017, U.S. Pat. No. 10,105,142, entitled SURGICAL STAPLER WITH PLURALITY OF CUTTING ELEMENTS, which issued on Oct. 23, 2018, U.S. Pat. No. 10,537,324, entitled STEPPED STAPLE CARTRIDGE WITH ASYMMETRICAL STAPLES, which issued on Jan. 21, 2020, U.S. Pat. No. 7,669,746, entitled STAPLE CARTRIDGES FOR FORMING STAPLES HAVING DIFFERING FORMED STAPLE HEIGHTS, which issued on Mar. 2, 2010, U.S. Pat. No. 8,123,100, entitled SURGICAL STAPLING INSTRUMENTS INCLUDING A CARTRIDGE HAVING MULTIPLE STAPLE SIZES, which issued on Feb. 28, 2012, U.S. Pat. No. 7,407,075, entitled STAPLE CARTRIDGE HAVING MULTIPLE STAPLE SIZES FOR A SURGICAL STAPLING INSTRUMENT, which issued on Aug. 5, 2008, U.S. Pat. No. 10,085,749, entitled SURGICAL APPARATUS WITH CONDUCTOR STRAIN RELIEF, which issued on Oct. 2, 2018, U.S. Pat. No. 10,765,427, entitled METHOD FOR ARTICULATING A SURGICAL INSTRUMENT, which issued on Sep. 8, 2020, U.S. Pat. No. 11,291,445, entitled SURGICAL STAPLE CARTRIDGES WITH INTEGRAL AUTHENTICATION KEYS, which issued on Apr. 5, 2022, U.S. Pat. No. 8,864,007, entitled IMPLANTABLE FASTENER CARTRIDGE HAVING A NON-UNIFORM ARRANGEMENT, which issued on Oct. 21, 2014, U.S. Pat. No. 11,490,890, entitled COMPRESSIBLE NON-FIBROUS ADJUNCTS, which issued on Nov. 8, 2022, U.S. Pat. No. 10,952,724, entitled THREE DIMENSIONAL ADJUNCTS, which issued on Mar. 23, 2021, U.S. Pat. No. 9,770,245, entitled LAYER ARRANGEMENTS FOR SURGICAL STAPLE CARTRIDGES, which issued on Sep. 26, 2017, U.S. Pat. No. 10,123,798, entitled TISSUE THICKNESS COMPENSATOR COMPRISING CONTROLLED RELEASE AND EXPANSION, which issued on Nov. 13, 2018, U.S. Pat. No. 10,166,023, entitled METHOD OF APPLYING A BUTTRESS TO A SURGICAL STAPLER END EFFECTOR, which issued on Jan. 1, 2019, U.S. Pat. No. 11,207,065, entitled METHOD FOR FABRICATING SURGICAL STAPLER ANVILS, which issued on Dec. 28, 2021, U.S. Pat. No. 8,141,762, entitled SURGICAL STAPLER COMPRISING A STAPLE POCKET, which issued on Mar. 27, 2012, U.S. Pat. No. 8,876,857, entitled END EFFECTOR WITH REDUNDANT CLOSING MECHANISMS, which issued on Nov. 4, 2014, U.S. Pat. No. 9,629,631, entitled COMPOSITE DRIVE BEAM FOR SURGICAL STAPLING, which issued on Apr. 25, 2017, U.S. Patent Application Publication No. 2022/0346858, entitled METHOD FOR OPERATING A SURGICAL INSTRUMENT INCLUDING SEGMENTED ELECTRODES, which published on Nov. 3, 2022, U.S. Patent Application Publication No. 2022/0304680, entitled DRIVERS FOR FASTENER CARTRIDGE ASSEMBLIES HAVING ROTARY DRIVE SCREWS, which published on Sep. 29, 2022, U.S. Patent Application Publication No. 2022/0304679, entitled METHOD OF USING A POWERED STAPLING DEVICE, which published on Sep. 29, 2022, U.S. Patent Publication No. 2019/0298350, entitled METHODS FOR CONTROLLING A POWERED SURGICAL STAPLER THAT HAS SEPARATE ROTARY CLOSURE AND FIRING SYSTEMS, which published on Oct. 3, 2019, U.S. Patent Application Publication No. 2017/0367695, entitled STAPLE CARTRIDGE COMPRISING WIRE STAPLES AND STAMPED STAPLES, which published on Dec. 28, 2017, U.S. Patent Application Publication No. 2015/0134077, entitled SEALING MATERIALS FOR USE IN SURGICAL STAPLING, which published on May 14, 2015, U.S. Patent Application Publication No. 2018/0168615, entitled METHOD OF DEFORMING STAPLES FROM TWO DIFFERENT TYPES OF STAPLE CARTRIDGES WITH THE SAME SURGICAL STAPLING INSTRUMENT, which published on Jun. 21, 2018, U.S. Patent Application Publication No. 2018/0132849, entitled STAPLE FORMING POCKET CONFIGURATIONS FOR CIRCULAR SURGICAL STAPLER ANVIL, which published on May 17, 2018, U.S. Patent Application Publication No. 2018/0168613, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS, which published on Jun. 21, 2018, U.S. Patent Application Publication No. 2017/0319205, entitled POWERED END EFFECTOR ASSEMBLY WITH PIVOTABLE CHANNEL, which published on Nov. 9, 2017, U.S. Patent Application Publication No. 2014/0001231, entitled FIRING SYSTEM LOCKOUT ARRANGEMENTS FOR SURGICAL INSTRUMENTS, which published on Jan. 2, 2014, U.S. Patent Application Publication No. 2016/0095596, entitled APPARATUS FOR ENDOSCOPIC PROCEDURES, which published on Apr. 7, 2016, U.S. Patent Application Publication No. 2015/0297199, entitled ADAPTER ASSEMBLY WITH GIMBAL FOR INTERCONNECTING ELECTROMECHANICAL SURGICAL DEVICES AND SURGICAL LOADING UNITS, AND SURGICAL SYSTEMS THEREOF, which published on Oct. 22, 2015, U.S. Patent Application Publication No. 2022/0031351, entitled SURGICAL INSTRUMENTS WITH DIFFERENT ARTICULATION JOINT ARRANGEMENTS FOR ACCOMMODATING FLEXIBLE ACTUATORS, which published on Feb. 3, 2022, U.S. Patent Application Publication No. 2022/0031320, entitled SURGICAL INSTRUMENTS WITH FLEXIBLE FIRING MEMBER ACTUATOR CONSTRAINT ARRANGEMENTS, which published on Feb. 3, 2022, U.S. Patent Application Publication No. 2023/0119119, entitled CABLE-DRIVEN ACTUATION SYSTEM FOR ROBOTIC SURGICAL TOOL ATTACHMENT, which published on Apr. 20, 2023, International Patent Publication No. WO2018/071497, entitled STAPLER CARTRIDGE WITH AN INTEGRAL KNIFE, which published on Apr. 18, 2018, International Patent Publication No. WO2018/049211, entitled WRIST ARCHITECTURE, which published on Mar. 15, 2018, U.S. Pat. No. 11,298,129, entitled METHOD FOR PROVIDING AN AUTHENTICATION LOCKOUT IN A SURGICAL STAPLER WITH A REPLACEABLE CARTRIDGE, which issued on Apr. 12, 22022/0022, U.S. Pat. No. 10,898,183, entitled ROBOTIC SURGICAL INSTRUMENT WITH CLOSED LOOP FEEDBACK TECHNIQUES FOR ADVANCEMENT OF CLOSURE MEMBER DURING FIRING, which issued on Jan. 26, 2021, U.S. Pat. No. 5,485,947, entitled LINEAR STAPLING MECHANISM WITH CUTTING MEANS, which issued on Jan. 23, 1996, International Patent Publication No. WO2018/049206, entitled STAPLER RELOAD DETECTION AND IDENTIFICATION, which published on Mar. 15, 2018, U.S. Patent Application Publication No. 2016/0249920, entitled SURGICAL FASTENER APPLYING APPARATUS, which published on Sep. 1, 2016, U.S. Design Pat. No. D974,560, entitled STAPLE CARTRIDGE, which issued on Jan. 3, 2023, U.S. Design Pat. No. D967,421, entitled STAPLE CARTRIDGE, which issued on Oct. 18, 2022, U.S. Design Pat. No. D933,220, entitled BUTTRESS ASSEMBLY FOR A SURGICAL STAPLER, which issued on Oct. 12, 2021, U.S. Pat. No. 9,839,420, entitled TISSUE THICKNESS COMPENSATOR COMPRISING AT LEAST ONE MEDICAMENT, which issued on Dec. 12, 2017, U.S. Pat. No. 10,588,623, entitled ADHESIVE FILM LAMINATE, which issued on Mar. 17, 2020, U.S. Pat. No. 8,499,992, entitled DEVICE AND METHOD FOR CONTROLLING COMPRESSION OF TISSUE, which issued on Aug. 6, 2013, U.S. Patent Application Publication No. 2022/0378427, entitled STAPLING INSTRUMENT COMPRISING JAW MOUNTS, which published on Dec. 1, 2022, U.S. Pat. No. 10,349,939, entitled METHOD OF APPLYING A BUTTRESS TO A SURGICAL STAPLER, which issued on Jul. 16, 2019, U.S. Pat. No. 9,386,988, entitled RETAINER ASSEMBLY INCLUDING A TISSUE THICKNESS COMPENSATOR, which issued on Jul. 12, 2016, U.S. Pat. No. 9,072,535, entitled SURGICAL STAPLING INSTRUMENTS WITH ROTATABLE STAPLE DEPLOYMENT ARRANGEMENTS, which issued on Jul. 7, 2015, and U.S. Pat. No. 9,844,369, entitled, SURGICAL END EFFECTORS WITH FIRING ELEMENT MONITORING ARRANGEMENTS, which issued on Dec. 19, 2017 are incorporated by reference herein.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

It is worthy to note that any reference numbers included in the appended claims are used to reference exemplary embodiments/elements described in the present disclosure. Accordingly, any such reference numbers are not meant to limit the scope of the subject matter recited in the appended claims.

While this invention has been described as having exemplary designs, the present invention may be further modified within the spirit and scope of the disclosure. This application is therefore intended to cover any variations, uses, or adaptations of the invention using its general principles.

It is worthy to note that any reference numbers included in the appended claims are used to reference exemplary embodiments/elements described in the present disclosure. Accordingly, any such reference numbers are not meant to limit the scope of the subject matter recited in the appended claims.

What is claimed is:

1. A surgical stapling assembly, comprising:
   a first jaw;
   a second jaw; and
   a staple cartridge assembly positioned in the first jaw, wherein the staple cartridge assembly comprises:
     a plurality of staples;
     a plurality of staple drivers;
     a cartridge body, comprising:
       a deck surface configured to support patient tissue;
       a longitudinal slot defined in the cartridge body and configured to receive at least a portion of a knife therethrough during a firing stroke;
       a plurality of staple cavities defined in the deck surface, wherein the plurality of staples are removably stored within the plurality of staple cavities; and
       a longitudinal wall extending vertically below the deck surface and longitudinally adjacent the longitudinal slot, wherein the longitudinal wall comprises a first zone comprising a first wall height within the firing stroke and a second zone comprising a second wall height within the firing stroke greater than the first wall height; and
     a sled movable longitudinally through the cartridge body, wherein the sled comprises:
       a support base; and
       a ramped wedge extending upward from the support base, wherein the ramped wedge is configured to lift the plurality of staple drivers to eject the plurality of staples from the plurality of staple cavities during the firing stroke, and wherein the sled is sized and configured resist deflection of the cartridge body during the firing stroke within the second zone.

2. The surgical stapling assembly of claim 1, wherein a vertical gap distance is defined between a bottom surface of the longitudinal wall and a top surface of the support base of the sled, and wherein the vertical gap distance comprises a first vertical gap distance defined within the first zone and second vertical gap distance defined within the second zone, and wherein the first vertical gap distance is less than the second vertical gap distance.

3. The surgical stapling assembly of claim 1, wherein the longitudinal slot comprises laterally-opposing inner slot walls defining the longitudinal slot, wherein the sled comprises a distal wedge extending distally from the support base configured to engage the laterally-opposing inner slot walls during the firing stroke, wherein the distal wedge is distal to the ramped wedge, and wherein the distal wedge comprises:
   a first portion comprising a first lateral wedge thickness; and
   a second portion comprising a second lateral wedge thickness, wherein the second portion is proximal to the first portion, and wherein the first lateral wedge thickness and the second lateral wedge thickness are different.

4. The surgical stapling assembly of claim 1, wherein the longitudinal slot comprises:
   a first zone comprising a first lateral slot thickness; and
   a second zone comprising a second lateral slot thickness, wherein the first lateral slot thickness is less than second lateral slot thickness.

5. The surgical stapling assembly of claim 1, wherein the staple cartridge assembly further comprises a support surface opposite a bottom of the cartridge body, wherein the sled traverses a longitudinally-extending pathway defined between the bottom of the cartridge body and the support surface, and wherein the staple cartridge assembly further comprises supports positioned between the support surface and the cartridge body within the longitudinally-extending pathway.

6. The surgical stapling assembly of claim 5, wherein the sled is configured to move the supports from a supporting position to a collapsed position during the firing stroke.

7. The surgical stapling assembly of claim 6, wherein the supports are biased into the supporting position, and wherein the supports are configured to reassume the supporting position from the collapsed position after the sled passes the supports.

8. The surgical stapling assembly of claim 1, wherein the staple cartridge assembly further comprises a material positioned within the longitudinal slot configured to be lifted above the deck surface by the sled during the firing stroke.

9. The surgical stapling assembly of claim 8, wherein the material is configured to laterally support the longitudinal slot during the firing stroke.

10. The surgical stapling assembly of claim 1, wherein the second jaw comprises apertures defined in a cartridge-facing surface of a proximal end of the second jaw, wherein the cartridge body comprises projections configured to be received within the apertures upon moving the second jaw into a clamped position, and wherein each aperture defines an inner surface surrounding an entirety of the projection received within the aperture.

11. A surgical staple cartridge, comprising:
- a plurality of staples;
- a cartridge body, comprising:
  - a deck surface configured to support patient tissue;
  - a longitudinal slot defined in the cartridge body and configured to receive at least a portion of a knife therethrough during a firing stroke;
  - a plurality of staple cavities defined in the deck surface, wherein the plurality of staples are removably stored within the plurality of staple cavities; and
  - a longitudinal wall extending vertically below the deck surface and longitudinally adjacent the longitudinal slot, wherein the longitudinal wall comprises a first longitudinal zone comprising a first wall height within the firing stroke and a second longitudinal zone comprising a second wall height greater than the first wall height; and
- a sled movable longitudinally through the first longitudinal zone and the second longitudinal zone, wherein the sled comprises:
  - a bottom; and
  - a wedge extending upward from the bottom, wherein the wedge is configured to eject the plurality of staples from the plurality of staple cavities during the firing stroke, and wherein the sled is sized and configured resist deflection of the cartridge body during the firing stroke within the second longitudinal zone.

12. The surgical staple cartridge of claim 11, wherein a vertical gap distance is defined between a bottom surface of the longitudinal wall and a top surface of the bottom of the sled, and wherein the vertical gap distance comprises a first vertical gap distance defined within the first longitudinal zone and second vertical gap distance defined within the second longitudinal zone, and wherein the first vertical gap distance is less than the second vertical gap distance.

13. The surgical staple cartridge of claim 11, wherein the longitudinal slot comprises laterally-opposing inner slot walls defining the longitudinal slot, wherein the sled comprises a distal wedge extending distally from the bottom configured to engage the laterally-opposing inner slot walls during the firing stroke, wherein the distal wedge is distal to the wedge, and wherein the distal wedge comprises:
- a first portion comprising a first lateral wedge thickness; and
- a second portion comprising a second lateral wedge thickness, wherein the second portion is proximal to the first portion, and wherein the first lateral wedge thickness and the second lateral wedge thickness are different.

14. The surgical staple cartridge of claim 11, wherein the longitudinal slot comprises:
- a first slot zone comprising a first lateral slot thickness; and
- a second slot zone comprising a second lateral slot thickness, wherein the first lateral slot thickness is less than second lateral slot thickness.

15. The surgical staple cartridge of claim 11, wherein the sled traverses a longitudinally-extending pathway defined beneath a plurality of cartridge walls of the cartridge body, and wherein the surgical staple cartridge further comprises supports extending downwardly from the cartridge walls and positioned within the longitudinally-extending pathway.

* * * * *